US012162922B2

(12) United States Patent
Zhao et al.

(10) Patent No.: US 12,162,922 B2
(45) Date of Patent: Dec. 10, 2024

(54) ENHANCED ANTIGEN PRESENTING ABILITY OF RNA CAR T CELLS BY CO-INTRODUCTION OF COSTIMULATORY MOLECULES

(71) Applicants: Novartis AG, Basel (CH); The Trustees of the University of Pennsylvania, Philadelphia, PA (US)

(72) Inventors: Yangbing Zhao, Lumberton, NJ (US); Devon J. Shedlock, Philadelphia, PA (US); Carl H. June, Merion Station, PA (US); Xiaojun Liu, Swarthmore, PA (US)

(73) Assignees: Novartis AG, Basel (CH); The Trustees of the University of Pennsylvania, Philadelphia, PA (US)

( * ) Notice: Subject to any disclaimer, the term of this patent is extended or adjusted under 35 U.S.C. 154(b) by 354 days.

(21) Appl. No.: 17/238,059

(22) Filed: Apr. 22, 2021

(65) Prior Publication Data

US 2021/0317183 A1 Oct. 14, 2021

Related U.S. Application Data

(62) Division of application No. 15/113,044, filed as application No. PCT/US2015/012284 on Jan. 21, 2015, now Pat. No. 11,028,143.

(60) Provisional application No. 61/929,813, filed on Jan. 21, 2014.

(51) Int. Cl.

| | |
|---|---|
| ***C07K 14/705*** | (2006.01) |
| ***A61K 38/00*** | (2006.01) |
| ***A61K 39/00*** | (2006.01) |
| ***A61K 39/02*** | (2006.01) |
| ***A61K 39/12*** | (2006.01) |
| ***A61K 39/39*** | (2006.01) |
| ***A61K 39/395*** | (2006.01) |
| ***C07K 14/54*** | (2006.01) |
| ***C07K 14/55*** | (2006.01) |
| ***C07K 14/725*** | (2006.01) |
| ***C07K 16/28*** | (2006.01) |
| ***C12N 5/0783*** | (2010.01) |
| ***C12N 7/00*** | (2006.01) |
| ***C12N 15/86*** | (2006.01) |
| ***G01N 33/50*** | (2006.01) |

(52) U.S. Cl.

CPC .... *C07K 14/70517* (2013.01); *A61K 39/0011* (2013.01); *A61K 39/02* (2013.01); *A61K 39/12* (2013.01); *A61K 39/39* (2013.01); *A61K 39/3955* (2013.01); *C07K 14/54* (2013.01); *C07K 14/5418* (2013.01); *C07K 14/5443* (2013.01); *C07K 14/55* (2013.01); *C07K 14/7051* (2013.01); *C07K 14/70521* (2013.01); *C07K 14/70532* (2013.01); *C07K 14/70575* (2013.01); *C07K 14/70596* (2013.01); *C07K 16/28* (2013.01); *C12N 5/0638* (2013.01); *C12N 7/00* (2013.01); *C12N 15/86* (2013.01); *G01N 33/505* (2013.01); *A61K 38/00* (2013.01); *A61K 2039/5158* (2013.01); *C07K 2317/53* (2013.01); *C07K 2317/622* (2013.01); *C07K 2319/30* (2013.01); *C12N 2501/51* (2013.01); *C12N 2501/515* (2013.01); *C12N 2510/00* (2013.01); *C12N 2760/16034* (2013.01)

(58) Field of Classification Search

None

See application file for complete search history.

(56) References Cited

U.S. PATENT DOCUMENTS

| | | | |
|---|---|---|---|
| 5,359,046 | A | 10/1994 | Capon et al. |
| 5,686,281 | A | 11/1997 | Roberts |
| 5,712,149 | A | 1/1998 | Roberts |
| 5,874,240 | A | 2/1999 | Ni et al. |
| 5,906,936 | A | 5/1999 | Eshhar et al. |
| 6,103,521 | A | 8/2000 | Capon et al. |
| 6,319,494 | B1 | 11/2001 | Capon et al. |
| 6,355,779 | B1 | 3/2002 | Goodwin et al. |
| 6,410,319 | B1 | 6/2002 | Raubitschek et al. |
| 6,569,997 | B1 | 5/2003 | Kwon |
| 7,049,136 | B2 | 5/2006 | Seed et al. |
| 7,052,906 | B1 | 5/2006 | Lawson et al. |
| 7,070,995 | B2 | 7/2006 | Jensen |
| 7,265,209 | B2 | 9/2007 | Jensen |
| 7,319,143 | B2 | 1/2008 | Gross et al. |
| 7,320,787 | B2 | 1/2008 | Seed et al. |
| 7,446,190 | B2 | 11/2008 | Sadelain et al. |
| 7,446,191 | B2 | 11/2008 | Jensen |

(Continued)

FOREIGN PATENT DOCUMENTS

| | | |
|---|---|---|
| EP | 0574512 A1 | 12/1993 |
| EP | 0871495 A1 | 10/1998 |

(Continued)

OTHER PUBLICATIONS

Zhao et al. (Cancer Research Nov. 15, 2010,70(22): 9053-9061) (Year: 2010).*

(Continued)

*Primary Examiner* — Peter J Reddig
(74) *Attorney, Agent, or Firm* — K&L GATES LLP

(57) ABSTRACT

The invention provides T cells comprising nucleic acid sequence encoding a chimeric antigen receptor and a nucleic acid sequence encoding an enhancer of T cell priming, compositions including the T cells, and methods of using the T cells to treat diseases associated with the expression of disease-associated antigens.

22 Claims, 12 Drawing Sheets

Specification includes a Sequence Listing.

(56) References Cited

U.S. PATENT DOCUMENTS 7,514,537 B2 4/2009 Jensen
7,638,326 B2 12/2009 June et al.
7,741,465 B1 6/2010 Eshhar et al.
7,745,140 B2 6/2010 June et al.
7,754,482 B2 7/2010 Riley et al.
7,994,298 B2 8/2011 Zhang et al.
8,211,422 B2 7/2012 Eshhar et al.
8,252,914 B2 8/2012 Zhang et al.
8,389,282 B2 3/2013 Sadelain et al.
8,399,645 B2 3/2013 Campana et al.
8,465,743 B2 6/2013 Rosenberg et al.
8,637,307 B2 1/2014 June et al.
8,722,400 B2 5/2014 Riley et al.
8,906,682 B2 12/2014 June et al.
8,911,993 B2 12/2014 June et al.
8,916,381 B1 12/2014 June et al.
8,975,071 B1 3/2015 June et al.
9,101,584 B2 8/2015 June et al.
9,102,760 B2 8/2015 June et al.
9,102,761 B2 8/2015 June et al.
9,272,002 B2 3/2016 Powell, Jr. et al.
9,328,156 B2 5/2016 June et al.
9,365,641 B2 6/2016 June et al.
9,394,368 B2 7/2016 Brogdon et al.
9,402,865 B2 * 8/2016 Powell ................. C07K 14/705
9,422,351 B2 8/2016 Scholler et al.
9,446,105 B2 9/2016 Powell, Jr.
9,464,140 B2 10/2016 June et al.
9,481,728 B2 11/2016 June et al.
9,499,629 B2 11/2016 June et al.
9,518,123 B2 12/2016 June et al.
9,540,445 B2 1/2017 June et al.
9,572,836 B2 2/2017 June et al.
9,573,988 B2 2/2017 Brogdon et al.
9,598,489 B2 3/2017 Powell, Jr.
9,714,278 B2 7/2017 June et al.
9,745,368 B2 8/2017 Milone et al.
9,765,156 B2 9/2017 June et al.
9,777,061 B2 10/2017 Ebersbach et al.
9,815,901 B2 11/2017 Brogdon et al.
9,937,205 B2 4/2018 Albelda et al.
10,040,846 B2 * 8/2018 Frigault ................. C07K 16/30
10,117,896 B2 * 11/2018 Powell, Jr. .............. A61P 35/00
10,174,095 B2 * 1/2019 Brogdon ............ C07K 16/2878
10,221,245 B2 * 3/2019 Brogdon .......... C07K 14/70578
10,253,086 B2 * 4/2019 Bitter ................. C07K 16/2866
10,357,514 B2 * 7/2019 June ................... C07K 14/7051
10,421,960 B2 * 9/2019 June ........................ A61P 35/00
10,457,729 B2 * 10/2019 Powell ............. C07K 14/70578
10,577,407 B2 * 3/2020 June ................ C07K 14/70503
10,640,569 B2 * 5/2020 Beatty ........................ A61P 1/18
10,696,749 B2 * 6/2020 June ................... C07K 16/2809
10,800,840 B2 * 10/2020 Frigault ............. C07K 14/7051
10,844,117 B2 * 11/2020 Powell, Jr. ......... C07K 14/7051
10,927,184 B2 * 2/2021 Brogdon ................. A61P 35/00
11,028,177 B2 * 6/2021 Brogdon .......... C07K 14/70517
11,084,880 B2 * 8/2021 Brogdon ................. A61P 35/02
11,149,076 B2 * 10/2021 Bitter ..................... A61K 45/06
11,274,298 B2 * 3/2022 June ....................... C12N 15/11
11,299,536 B2 * 4/2022 Frigault ................. C12N 15/86
11,484,552 B2 * 11/2022 Powell, Jr. ......... A61K 39/3955
2003/0060444 A1 3/2003 Finney et al.
2003/0077249 A1 4/2003 Bebbington et al.
2003/0147869 A1 8/2003 Riley et al.
2003/0148982 A1 8/2003 Brenner et al.
2003/0224520 A1 12/2003 June et al.
2004/0038886 A1 2/2004 Finney et al.
2004/0043401 A1 3/2004 Sadelain et al.
2004/0101519 A1 5/2004 June et al.
2004/0110290 A1 6/2004 June et al.
2005/0113564 A1 5/2005 Campana et al.
2005/0129671 A1 6/2005 Cooper et al.
2006/0034810 A1 2/2006 Riley et al.
2007/0036773 A1 2/2007 Cooper et al.
2008/0131415 A1 6/2008 Riddell et al.
2009/0257994 A1 10/2009 Jensen
2010/0261269 A1 10/2010 June et al.
2011/0052554 A1 3/2011 Zakrzewski et al.
2011/0262467 A1 10/2011 Riley et al.
2012/0148552 A1 6/2012 Jensen
2012/0321667 A1 12/2012 Sentman
2013/0071409 A1 3/2013 Riley et al.
2013/0071414 A1 3/2013 Dotti et al.
2013/0149337 A1 6/2013 Cooper et al.
2013/0155909 A1 6/2013 Jackson et al.
2013/0287748 A1 10/2013 June et al.
2013/0288368 A1 10/2013 June et al.
2013/0309258 A1 11/2013 June et al.
2014/0050708 A1 2/2014 Powell et al.
2014/0099309 A1 4/2014 Powell, Jr. et al.
2014/0099340 A1 4/2014 June et al.
2014/0106449 A1 4/2014 June et al.
2014/0186947 A1 7/2014 June et al.
2014/0212446 A1 7/2014 Riley et al.
2014/0219975 A1 8/2014 June et al.
2014/0227237 A1 8/2014 June et al.
2014/0255363 A1 9/2014 Metelitsa et al.
2014/0271635 A1 9/2014 Brogdon et al.
2014/0322169 A1 10/2014 Harper et al.
2014/0322183 A1 10/2014 Milone et al.
2014/0322212 A1 10/2014 Brogdon et al.
2014/0322275 A1 10/2014 Brogdon et al.
2014/0370017 A1 12/2014 June et al.
2014/0370045 A1 12/2014 June et al.
2015/0017141 A1 1/2015 June et al.
2015/0024482 A1 1/2015 Frigault et al.
2015/0050729 A1 2/2015 June et al.
2015/0093822 A1 4/2015 June et al.
2015/0099299 A1 4/2015 June et al.
2015/0118202 A1 4/2015 June et al.
2015/0140019 A1 5/2015 June et al.
2015/0190428 A1 7/2015 June et al.
2015/0202286 A1 7/2015 June et al.
2015/0283178 A1 10/2015 June et al.
2015/0290244 A1 10/2015 June et al.
2015/0342994 A1 12/2015 Riley et al.
2016/0046724 A1 2/2016 Brogdon et al.
2016/0051651 A1 2/2016 Brogdon et al.
2016/0068601 A1 3/2016 Brogdon et al.
2016/0096892 A1 4/2016 Brogdon et al.
2016/0185861 A1 6/2016 Bedoya et al.
2016/0311907 A1 10/2016 Brogdon et al.
2016/0311917 A1 10/2016 Beatty et al.
2016/0340406 A1 11/2016 Zhao et al.
2016/0362472 A1 12/2016 Bitter et al.
2017/0008963 A1 1/2017 Brogdon et al.
2017/0081411 A1 3/2017 Engels et al.
2017/0137783 A1 5/2017 Bedoya et al.
2017/0183415 A1 6/2017 Brogdon et al.
2017/0209492 A1 7/2017 June et al.
2017/0211055 A1 7/2017 Brogdon et al.
2017/0226495 A1 8/2017 Guimaraes
2017/0239294 A1 8/2017 Thomas-Tikhonenko et al.
2017/0260268 A1 9/2017 Beatty et al.
2017/0274014 A1 9/2017 Brogdon et al.
2017/0306416 A1 10/2017 Bedoya et al.
2017/0335281 A1 11/2017 Loew et al.
2018/0022795 A1 1/2018 Milone et al.
2018/0044423 A1 2/2018 Ebersbach et al.
2018/0044424 A1 2/2018 June et al.
2018/0118834 A1 5/2018 Brogdon et al.
2018/0125892 A1 5/2018 Brannetti et al.
2018/0133296 A1 5/2018 Barrett et al.
2018/0140602 A1 5/2018 Angst et al.
2018/0230193 A1 8/2018 Loew et al.
2018/0252727 A1 9/2018 Garfall et al.
2018/0258149 A1 9/2018 Motz et al.
2018/0298068 A1 10/2018 Albelda
2018/0312595 A1 11/2018 Brogdon et al.
2019/0000880 A1 1/2019 Motz et al.
2019/0000944 A1 1/2019 Brogdon et al.
2019/0135940 A1 5/2019 Brogdon et al.
2019/0151365 A1 5/2019 Anak et al.
2019/0153061 A1 5/2019 Brogdon et al.

(56) References Cited

U.S. PATENT DOCUMENTS

| | | | |
|---|---|---|---|
| 2019/0161542 | A1 | 5/2019 | Gill et al. |
| 2019/0263914 | A1 | 8/2019 | Brogdon et al. |
| 2019/0269727 | A1 | 9/2019 | Fachin et al. |
| 2019/0292238 | A1 | 9/2019 | Bitter et al. |
| 2019/0292257 | A1 | 9/2019 | Bedoya et al. |
| 2019/0298715 | A1 | 10/2019 | Motz et al. |
| 2019/0330356 | A1 | 10/2019 | Brogdon et al. |
| 2019/0336504 | A1 | 11/2019 | Gill et al. |
| 2019/0375815 | A1 | 12/2019 | Engels et al. |
| 2019/0382500 | A1 | 12/2019 | Abujoub et al. |
| 2019/0388471 | A1 | 12/2019 | June et al. |
| 2019/0389928 | A1 | 12/2019 | Posey et al. |
| 2020/0048359 | A1 | 2/2020 | Albelda et al. |
| 2020/0055948 | A1 | 2/2020 | Daley et al. |
| 2020/0061113 | A1 | 2/2020 | Kassim et al. |
| 2020/0085869 | A1 | 3/2020 | Schuster et al. |
| 2020/0087376 | A1 | 3/2020 | Fraietta et al. |
| 2020/0113941 | A1 | 4/2020 | Brannetti et al. |
| 2020/0179511 | A1 | 6/2020 | Daley et al. |
| 2020/0215171 | A1 | 7/2020 | Brogdon et al. |
| 2020/0281973 | A1 | 9/2020 | Dranoff |
| 2020/0283729 | A1 | 9/2020 | Loew et al. |
| 2020/0291354 | A1 | 9/2020 | Johnson et al. |
| 2020/0339704 | A1 | 10/2020 | Bradner et al. |
| 2020/0360431 | A1 | 11/2020 | Garfall et al. |
| 2020/0368268 | A1 | 11/2020 | Johnson et al. |
| 2020/0370012 | A1 | 11/2020 | Fraietta et al. |
| 2020/0371091 | A1 | 11/2020 | Pruteanu-Malinici et al. |
| 2020/0399383 | A1 | 12/2020 | Scholler et al. |
| 2021/0002377 | A1 | 1/2021 | Brogdon et al. |
| 2021/0047405 | A1 | 2/2021 | Nobles et al. |
| 2021/0079073 | A1 | 3/2021 | Milone et al. |
| 2021/0087279 | A1 | 3/2021 | Engels et al. |
| 2021/0139595 | A1 | 5/2021 | Ebersbach et al. |
| 2021/0171909 | A1 | 6/2021 | Golovina |
| 2021/0172020 | A1 | 6/2021 | Bedoya et al. |
| 2021/0177896 | A1 | 6/2021 | Porter et al. |
| 2021/0177900 | A1 | 6/2021 | Engels et al. |
| 2021/0213063 | A1 | 7/2021 | Isaacs et al. |
| 2021/0220404 | A1 | 7/2021 | Abujoub et al. |
| 2021/0246423 | A1 | 8/2021 | Bedoya et al. |
| 2021/0284752 | A1 | 9/2021 | Brogdon et al. |
| 2021/0317183 | A1 | 10/2021 | Zhao et al. |
| 2021/0347851 | A1 | 11/2021 | Isaacs et al. |
| 2021/0396739 | A1 | 12/2021 | Pruteanu-Malinici et al. |
| 2022/0047633 | A1 | 2/2022 | Grupp |
| 2022/0064316 | A1 | 3/2022 | Brogdon et al. |
| 2022/0089750 | A1 | 3/2022 | June et al. |
| 2022/0152150 | A1 | 5/2022 | Koshy et al. |
| 2022/0168389 | A1 | 6/2022 | Ghassemi et al. |
| 2022/0195010 | A1 | 6/2022 | Bitter et al. |
| 2022/0251152 | A1 | 8/2022 | Carbonneau et al. |
| 2022/0364055 | A1 | 11/2022 | Treanor et al. |
| 2022/0387486 | A1 | 12/2022 | Brannetti et al. |
| 2023/0026049 | A1 | 1/2023 | Brogdon et al. |
| 2023/0071283 | A1 | 3/2023 | Golosov et al. |
| 2023/0074800 | A1 | 3/2023 | Berger et al. |
| 2023/0111593 | A1 | 4/2023 | Schuster et al. |
| 2023/0139800 | A1 | 5/2023 | Motz et al. |
| 2023/0174933 | A1 | 6/2023 | Brogdon et al. |
| 2023/0183368 | A1 | 6/2023 | Abujoub et al. |
| 2023/0220090 | A1 | 7/2023 | Brogdon et al. |
| 2023/0250179 | A1 | 8/2023 | Abujoub et al. |
| 2023/0256017 | A1 | 8/2023 | Brogdon et al. |
| 2023/0295296 | A1 | 9/2023 | Bedoya et al. |
| 2023/0302155 | A1 | 9/2023 | Koshy et al. |
| 2023/0312677 | A1 | 10/2023 | Posey et al. |
| 2023/0332104 | A1 | 10/2023 | Estevez Silva et al. |
| 2023/0357717 | A1 | 11/2023 | Johnson et al. |
| 2023/0374105 | A1 | 11/2023 | Bitter et al. |
| 2023/0416390 | A1 | 12/2023 | Abujoub et al. |
| 2024/0024360 | A1 | 1/2024 | Fachin et al. |
| 2024/0033358 | A1 | 2/2024 | Chadbourne et al. |
| 2024/0083968 | A1 | 3/2024 | Loew et al. |
| 2024/0139244 | A1 | 5/2024 | Dranoff |

FOREIGN PATENT DOCUMENTS

| | | | |
|---|---|---|---|
| EP | 1226244 | A2 | 7/2002 |
| WO | 1992015322 | A1 | 9/1992 |
| WO | 199530014 | A1 | 11/1995 |
| WO | 9623814 | A1 | 8/1996 |
| WO | 9624671 | A1 | 8/1996 |
| WO | 1997015669 | A1 | 5/1997 |
| WO | 9723613 | A2 | 7/1997 |
| WO | 9818809 | A1 | 5/1998 |
| WO | 9900494 | A2 | 1/1999 |
| WO | 9957268 | A1 | 11/1999 |
| WO | 0014257 | A1 | 3/2000 |
| WO | 2002033101 | A1 | 4/2002 |
| WO | 02077029 | A2 | 10/2002 |
| WO | 02088334 | A1 | 11/2002 |
| WO | 2003057171 | A2 | 7/2003 |
| WO | 2005019429 | A2 | 3/2005 |
| WO | 2005044996 | A2 | 5/2005 |
| WO | 2005/118788 | A2 | 12/2005 |
| WO | 2006060878 | A1 | 6/2006 |
| WO | 2008045437 | A2 | 4/2008 |
| WO | 2008121420 | A1 | 10/2008 |
| WO | 2010085660 | A2 | 7/2010 |
| WO | 2011059836 | A2 | 5/2011 |
| WO | 2011097477 | A1 | 8/2011 |
| WO | 2012058460 | A2 | 5/2012 |
| WO | 2012079000 | A1 | 6/2012 |
| WO | 2012082841 | A2 | 6/2012 |
| WO | 2012/099973 | A2 | 7/2012 |
| WO | 2012127464 | A2 | 9/2012 |
| WO | 2012129514 | A1 | 9/2012 |
| WO | 2012135854 | A2 | 10/2012 |
| WO | 2012138858 | A1 | 10/2012 |
| WO | 2013019615 | A2 | 2/2013 |
| WO | 2013033626 | A2 | 3/2013 |
| WO | 2013040371 | A2 | 3/2013 |
| WO | 2013040557 | A2 | 3/2013 |
| WO | 2013059593 | A1 | 4/2013 |
| WO | 2013063419 | A2 | 5/2013 |
| WO | 2013/126712 | A1 | 8/2013 |
| WO | 2013126729 | A1 | 8/2013 |
| WO | 2013126733 | A1 | 8/2013 |
| WO | 2014/011984 | A1 | 1/2014 |
| WO | 2014/011987 | A1 | 1/2014 |
| WO | 2014/011993 | A2 | 1/2014 |
| WO | 2014/012001 | A2 | 1/2014 |
| WO | 2014011988 | A2 | 1/2014 |
| WO | 2014011996 | A1 | 1/2014 |
| WO | 2014031687 | A1 | 2/2014 |
| WO | 2014039513 | A2 | 3/2014 |
| WO | 2014/055442 | A2 | 4/2014 |
| WO | 2014055657 | A1 | 4/2014 |
| WO | 2014130635 | A1 | 8/2014 |
| WO | 2014/145252 | A2 | 9/2014 |
| WO | 2014/186469 | A2 | 11/2014 |
| WO | 2015090229 | A1 | 6/2015 |
| WO | 2015090230 | A1 | 6/2015 |
| WO | 2015112626 | A1 | 7/2015 |
| WO | 2015/142661 | A1 | 9/2015 |
| WO | 2015142675 | A2 | 9/2015 |
| WO | 2015157252 | A1 | 10/2015 |
| WO | 2016014501 | A1 | 1/2016 |
| WO | 2016014530 | A1 | 1/2016 |
| WO | 2016014535 | A1 | 1/2016 |
| WO | 2016014553 | A1 | 1/2016 |
| WO | 2016014565 | A2 | 1/2016 |
| WO | 2016014576 | A1 | 1/2016 |
| WO | 2016019300 | A1 | 2/2016 |
| WO | 2016025880 | A1 | 2/2016 |
| WO | 2016028896 | A1 | 2/2016 |
| WO | 2016044605 | A1 | 3/2016 |

OTHER PUBLICATIONS

Kershaw et al. "Gene-engineered T cells for cancer therapy", Nature Reviews Cancer, vol. 13, No. 8, Jul. 24, 2013, pp. 525-541.

(56) References Cited

OTHER PUBLICATIONS

Kershaw et al., "A Phase I Study on Adoptive Immunotherapy Using Gene-Modified T Cells for Ovarian Cancer," Clin. Cancer Res. 12(20 Pt 1): 6106-6115 (2006).
Kim et al., "Human 4-1BB regulates CD28 co-stimulation to promote Th1 cell responses" Eur. J. Immunol. (1998) vol. 28 pp. 881-890.
Kochenderfer et al, "A Phase I Clinical Trial of Treatment of B-Cell Malignancies with Autologous Anti-Cd19-CAR-Transduced T Cells" Blood (2010) vol. 116 No. 21 pp. 1179-1180 & 52nd Annual Meeting of the American-Society-of-Hematology (ASH); Orlando, FL, USA; Dec. 4-7, 2010 abstract.
Kochenderfer et al. "Construction and Pre-clinical Evaluation of an Anti-CD19 Chimeric Antigen Receptor", J Immunother (2009) vol. 32, No. 7, pp. 689-702.
Kochenderfer et al., "Eradication of B-lineage cells and regression of lymphoma in a patient treated with autologous T cells genetically-engineered to recognize CD19," Blood 116: 4099-4102 (2010).
Kraus et al., "Antigen-dependent CD28 Signaling Selectively Enhances Survival and Proliferation in Genetically Modified Activated Human Primary T Lymphocytes" J. Exp. Med. (1998) vol. 188 Np 4 pp. 619-626.
Krebs et al. "Genetically Modified T Cells to Target Glioblastoma", Frontiers in Oncology, vol. 3, Jan. 1, 2013.
Kwon et al., "cDNA sequences of two inducible T-cell genes". Proc. Natl. Acad. Sci. U.S.A. 86(6): 1963-1967 (1989).
Lamanna et al., "Pentostatin, Cyclophosphamide, and Rutuximab Is an Active, Well-Tolerated Regimen for Patients With Previously Treated Chronic Lymphocytic Leukemia" Journal of Clinical Oncology (2008) vol. 24 No. 10 pp. 1575-1581.
Lamers et al., "Treatment of Metastatic Renal Cell Carcinoma With Autologous T-Lymphocytes Genetically Retargeted Against Carbonic Anhydrase IX: First Clinical Experience," J. Clin. Oncol. 24(13): e20-e22 (2006).
Laport et al., "Adoptive transfer of costimulated T cells induces lymphocytosis in patients with relapsed/refractory non-Hodgkin lymphoma following CD34 +-selected hematopoietic cell transplantation" Blood (2003) vol. 102 No. 6 pp. 2004-2013.
Lee et al., "In vivo Inhibition of Human CD19-Targeted Effector T Cells by Natural T Regulatory Cells in a Kenotransplant Murine Model of B Cell Malignancy" Cancer Research (2011) vol. 71 No. 8 pp. 2871-2881.
Lee et al., "The Future is Now: Chimeric Antigen Receptors as New Targeted Therapies for Childhood Cancer," Clin. Cancer Res. 18: 2780-2790 (2012).
Letourneur et al., "T-cell and basophil activation through the cytoplasmic tail of T-cell-receptor zeta family proteins," Proc. Natl. Acad. Sci. U.S.A 88: 8905-8909 (1991).
Levine et al., "Gene transfer in humans using a conditionally replicating lentiviral vector" PNAS (2006) vol. 103 No. 46 pp 17372-17377.
Macallan et al., "Measurement and modeling of human T cell kinetics" European Journal of Immunology (2003) vol. 33 pp. 2316-2326.
Maher et al., "Human T lymphocyte cytotoxicity and proliferation directed by a single chimeric TCRzeta/CD28 receptor," Nat. Biotechnol. 20: 70-75 (2002).
Markley et al. "IL-7 and IL-21 are superior to IL-2 and IL-15 in promoting human T cell-mediated rejection of systemic lymphoma in immunodeficient mice" Blood (2010) vol. 115, No. 17, pp. 3508-3519.
McGuinness et al., "Anti-tumor activity of human T cells expressing the CC49-zeta chimeric immune receptor," Hum. Gene Ther. 10: 165-173 (1999).
Milone et al, "Chimeric Receptors Containing CD137 Signal Transduction Domains Mediate Enhanced Survival of T Cells and Increased Antileukemic Efficacy In Vivo" Molecular Therapy (2009) vol. 17 No. 8 pp. 1453-1464.
Molina, "A Decade of Rituximab: Improving Survival Outcomes in Non-Hodgkin's Lymphoma" Annu. Rev. Med. (2008) vol. 59 pp. 237-250.
Morgan et al., "Case Report of a Serious Adverse Event Following the Administration of T Cells Transduced With a Chimeric Anitgen Receptor Recognizing ErbB2," Mol. Ther. 18(4): 843-851 (2010).
Moritz and Groner, "A spacer region between the single chain antibody- and the CD3 zeta-chain domain of chimeric T cell receptor components is required for efficient ligand binding and signaling activity," Gene Therapy 2(8): 539-546 (1995).
Moritz et al., "Cytotoxic T lymphocytes with a grafted recognition specificity for ERBB2-expressing tumor cells" Proc. Natl. Acad. Sci (1994) vol. 91 pp. 4318-4322.
Naldini et al., "In Vivo Gene Delivery and Stable Transduction of Nondividing Cells by a Lentiviral Vector" Science (1996) vol. 272 pp. 263-267.
NCBI accession HM_852952 accessed Sep. 29, 2015 from http://www.ncbi.nlm.nih.gov/nuccore/hm852952.
Nicholson et al., "Construction and Characterisation of a Function CD19 Specific Single Chain Fv Fragment for Immunotherapy of B Lineage Leukaemia and Lymphoma," Molecular Immunology 34(I6-I7): 1157-1165 (1997).
Park and Brentjens "Adoptive Immunotherapy for B-cell Malignancies with Autologous Chimeric Antigen Receptor Modified Tumor Targeted T Cells" Discovery Medicine (2010) vol. 9 No. 47 pp. 277-288.
Park et al. "Adoptive Transfer of Chimeric Antigen Receptor Re-directed Cytolytic T Lymphocyte Clones in Patients with Neuroblastoma", Molecular Therapy (2007) vol. 15 No. 4 pp. 825-833.
Patel et al., "Impact of chimeric immune receptor extracellular protein domains on T cell function" Gene Therapy (1999) vol. 6 pp. 412-419.
Porter et al. "Chimeric Antigen Receptor-Modified T Cells in Chronic Lymphoid Leukemia", The New England Journal of Medicine (2011) vol. 365 No. 8 pp. 725-733.
Porter et al., "A phase 1 trial of donor lumphocyte infusions expanded and activated ex vivo via CD3/CD28 costimulation" Blood (2006) vol. 107 No. 4 pp. 1325-1331.
Porter et al., "Chimeric Antigen Receptor Therapy for B-cell Malignancies" Journal of Cancer (2011) vol. 2 pp. 331-332.
Prazma et al. "Dendritic cell CD83: A therapeutic target or innocent bystander?" Immunology Letters (2008) vol. 115, pp 1-8.
Pule et al., "Virus-specific T cells engineered to coexpress tumor-specific receptors: persistence and antitumor activity in individuals with neuroblastoma" Nat. Med. (2008) vol. 14 No. 11 pp. 1264-1270.
Rapoport et al., "Restoration of immunity in lymphopenic individuals with cancer by vaccination and adoptive T-cell transfer" Nature Medicine (2005) vol. 11 No. 11 pp. 1230-1237.
Riet et al. "Nonviral RNA transfection to transiently modify T cells with chimeric antigen receptors for adoptive therapy", Methods in Molecular Biology, Humana Press, Inc, US, vol. 969, Jan. 1, 2013, pp. 187-201.
Roederer, "T-cell dynamics of immunodeficiency" Nature Medicine (1995) vol. 1 No. 7 pp. 621-622.
Romeo et al., "Cellular immunity to HIV activated by CD4 fused to T cell or Fc receptor polypeptides," Cell 64:1037-1046 (1991).
Sabbagh et al., "TNF family ligands define niches for T cell memory" Trends in Immunology (2007) vol. 28 No. 8 pp. 333-339.
Sadelain et al. "The promise and potential pitfalls of chimeric antigen receptors." Current Opinion Immunology (2009) vol. 21 No. 2 pp. 215-223.
Sadelain et al., "Targeting Tumours with Genetically Enhanced T Lymphocytes," Nature Reviews: Cancer 3: 35-45 (2003).
Savoldo et al., "CD28 costimulation improves expansion and persistence of chimeric antigen receptor-modified T cells in lymphoma patients" The Journal of Clinical Investigation (2011) vol. 121 No. 5 pp. 1822-1826.
Sebestyen et al., "Human TCR That Incorporate CD3 Induce Highly Preferred Pairing between TCR and Chains following Gene Transfer" Journal of Immunology (2008) vol. 180 pp. 7736-7746.

(56) References Cited

OTHER PUBLICATIONS

Shirasu et al., "Functional Design of Chimeric T-Cell Antigen Receptors for Adoptive Immunotherapy of Cancer: Architecture and Outcomes," AntiCancer Res. 32: 2377-2384 (2012).
Sorror et al., "Outcomes after allogeneic hematopoietic cell transplantation with nonmyeloablative or myeloablative conditioning regimens for treatment of lymphoma and chronic lymphocytic leukemia" Blood (2008) vol. 111 No. 1 pp. 446-452.
Stephan et al., "T cell-encoded CD80 and 4-1BBL induce auto- and transcostimulation, resulting in potent tumor rejection," Nature Medicine (2007) vol. 13, No. 12, pp. 1440-1449.
Till et al., "Adoptive immunotherapy for indolent non-Hodgkin lymphoma and mantle cell lymphoma using genetically modified autologous CD20-specific T cells" Blood (2008) vol. 112 No. 6 pp. 2261-2271.
Uckun et al., "Detailed studies on expression and function of CD19 surface determinant by using B43 monoclonal antibody and the clinical potential of anti-CD19 immunotoxins" Blood (1988) vol. 71 pp. 13-29.
Vinay & Kwon, "Role of 4-1BB in immune responses" Immunology (1998) vol. 10 pp. 481-489.
Willemsen et al., "Genetic Engineering of T Cell Specificity for Immunotherapy of Cancer" Human Immunology (2003) vol. 64 pp. 56-68.
Zhao et al., "A Herceptin-Based Chimeric Antigen Receptor with Modified Signaling Domains Leads to Enhanced Survival of Transduced T Lymphocytes and Antitumor Activity" The Journal of Immunology (2009) vol. 183 pp. 5563-5574.
Zufferey et al., "Multiply attenuated lentiviral vector achieves efficient gene delivery in vivo" Nature Biotechnology (1997) vol. 15 pp. 871-876.
Baeksgaard & Sorensen, "Acute tumor lysis syndrome in solid tumors—a case report and review of the literature" Cancer Chemotherapy Pharmacology (2003) vol. 51 pp. 187-192.
Bondanza et al. "Suicide gene therapy of graft-versus-host disease induced by central memory human T lymphocytes" Blood (2006) vol. 107 No. 5 pp. 1828-1836.
Brentjens et al. "Genetically Targeted T Cells Eradicate Systemic Acute Lymphoblastic Leukemia Xenografts", Clinical Cancer Research(2007) vol. 13, No. 18, pp. 5426-5435.
Brentjens et al. "Treatment of Chronic Lymphocytic Leukemia With Genetically Targeted Autologous T Cells: Case Report of an Unforeseen Adverse Event in a Phase I Clinical Trial" The American Society of Gene Therapy (2010) vol. 18 No. 4 pp. 666-668.
Brentjens et al., "A Phase I Trial for the Treatment of chemo-Refractory Chronic Lymphocytic Leukemia with CD19-Targeted Autologous T Cells" Molecular Therapy (2008) vol. 16 Suppl 1 p. S15.
Brentjens et al., "CD19-Targeted T Cells Rapidly Induce Molecular Remissions in Adults with Chemotherapy- Refractory Acute Lymphoblastic Leukemia," Sci. Transl. Med. 5:177ra138 (2013).
Brentjens et al., "Eradication of systemic B-cell tumors by genetically targeted human T lymphocytes co-stimulated by CD80 and interleukin-15" Nature Medicine (2003) vol. 9 No. 3 pp. 279-286.
Brentjens et al., "Safety and persistence of adoptively transferred autologous CD19-targeted T cells in patients with relapsed or chemotherapy refractory B-cell leukemias" Blood (2011) vol. 118 No. 18 pp. 4817-4828.
Brocker and Karjalainen, "Signals through T Cell Receptor-Chain alone Are Insufficient to Prime Resting T Lymphocytes" J. Exp. Med. (1995) vol. 181 pp. 1653-1659.
Call & Wucherpfennig, "The T Cell Receptor: Critical Role of the Membrane Environment in Receptor Assembly and Function" Annu. Rev. Immunol. (2005) vol. 23 pp. 101-125.
Carpenito et al. "Control of large, established tumor xenografts with genetically retargeted human T cells containing CD28 and CD137 domains", Proc Natl Acad Sci USA (2009) vol. 106 pp. 3360-3365.
Chinnasamy et al. "Local Delivery of Interleukin-12 Using T Cells Targeting VEGF Receptor-2 Eradicates Multiple Vascularized Tumors in Mice", Clinical Cancer Research, vol. 18, No. 6, Jan. 30, 2012, pp. 1672-1683.
Chmielewski et al. "IL-12 Release by Engineered T Cells Expressing Chimeric Antigen Receptors Can Effectively Muster an Antigen Receptors Can Effectively Muster an Antigen-Independent Macrophage Response on Tumor Cells That Have Shut Down Tumor Antigen Expression", Cancer Research, vol. 71, No. 17, Jul. 8, 2011, pp. 5697-7506.
Chmielewski et al. "Of CARs and TRUCKs: chimeric antigen receptor (CAR) T cells engineered with an inducible cytokine to modulate the tumor stroma", Immunological Reviews, vol. 257, No. 1, Jan. 13, 2014, pp. 83-90.
Davila et al. "B Cell Aplasia in a Patient with Relapsed B Cell Acute Lymphoblastic Leukemia Following Re-Induction and Consolidation with Autologous T Cells Genetically Targeted to the CD19 Antigen" 53rd ASH Annual Meeting and Exposition (2010) Oral and Poster Abstract.
Dohner et al., "p53 Gene Deletion Predicts for Poor Survival and Non-Response to Therapy With Purine Analogs in Chronic B-Cell Leukemias" Blood (1995) vol. 85 No. 6 pp. 1580-1589.
Dotti et al. "Design and development of therapies using chimeric antigen receptor-expressing T cells", Immunological Reviews, vol. 257, No. 1, Dec. 13, 2013, pp. 107-126.
Dropulic and June, "Gene-Based Immunotherapy for Human Immunodeficiency Virus Infection and Acquired Immunodeficiency Syndrome" Human Gene Therapy (2006) vol. 17 pp. 577-588.
Dull et al., "A Third-Generation Lentivirus Vector with a Conditional Packaging System" Journal of Virology (1998) vol. 72 No. 11 pp. 8463-8471.
Eshhar et al., "Specific activation and targeting of cytotoxic lymphocytes through chimeric single chains consisting of antibody-binding domains and the gamma or zeta subunits of the immunoglobulin and T-cell receptors," PNAS USA 90: 720-724 (1993).
Finney et al., "Activation of resting human primary T cells with chimeric receptors: costimulation from CD28, inducible costimulator, CD134, and CD137 (4-1BB) in series with signals from the TCR zeta chain," J. Immunol. 172: 104-113 (2004).
Finney et al., "Chimeric receptors providing both primary and costimulatory signaling in T cells from a single gene product," J. Immunol. 161: 2791-2797 (1998).
Frey, N. "Genetically Engineered Lymphocyte Therapy in Treating Patients With B-Cell Leukemia or Lymphoma That is Resistant or Refractory to Chemotherapy" (2015) Clinical Trial NCT01029366.
Friedmann-Morvinski et al., "Redirected primary T cells harboring a chimeric receptor require costimulation for their antigen-specific activation," Blood 105: 3087-3093 (2005).
Geiger & Jyothi, "Development and Application of Receptor-Modified T Lymphocytes for Adoptive Immunotherapy" Transfusion Medicine Reviews (2001) vol. 15 No. 1 pp. 21-34.
Geiger et al., "Integrated src kinase and constimulatory activity enhances signal transduction through single-chain chimeric receptors in T lymphocytes," Blood 98(8): 2364-2371 (2001).
GenBank Accession No. NP_000725.1 accessed on Jan. 7, 2016 from http://www.ncbi.nlm.nih.gov/protein/NP_000725.
GenBank Accession No. NP_932170.1 accessed Jan. 7, 2016 from http://www.ncbi.nlm.nih.gov/protein/NP_932170.
Gilham et al., "Primary Polyclonal Human T Lymphocytes Targeted to Carcino-Embryonic Antigens and Neural Cell Adhesion Molecule Tumor Antigens by CD3-Based Chimeric Immune Receptors" Journal of Immunotherapy (2002) vol. 25 No 2 pp. 139-151.
Gong et al. "Cancer Patient T Cells Genetically Targeted to Prostate-Specific Membrane Antigen Specifically Lyse Prostate Cancer Cells and Release Cytokines in Response to Prostate-Specific Membrane Antigen" Neoplasia (1999) vol. 1 No. 2 pp. 123-127.
Gribben et al., "Stem cell transplantation for indolent lymphoma and chronic lymphocytic leukemia" Biol Blood Marrow Transplant (2011) vol. 17 (1 Suppl): S63-S70.
Griffin, "Development and applications of surface-linked single chain antibodies against T-cell antigens" Journal of Immunological Methods (2001) vol. 248 pp. 77-90.

(56) References Cited

OTHER PUBLICATIONS

Gross et al., "Endowing T cells with antibody specificity using chimeric T cell receptors," The FASEB Journal 6: 3370-3378 (1992).
Grupp et al. "Chimeric Antigen Receptor-Modified T Cells for Acute Lymphoid Leukemia", New England Journal of Medicine (2013) vol. 368 No. 16 pp. 1509-1518.
Hallek et al., "Guidelines for the diagnosis and treatment of chronic lymphocytic leukemia: a report from the International Workshop on Chronic Lymphocytic Leukemia updating the National Cancer Institute Working Group 1996 guidelines" Blood (2008) vol. 111 No. 12 pp. 5446-5456.
Hekele et al., "Growth Retardation of Tumors By Adoptive Transfer of Cytotoxic T Lymphocytes Reprogrammed By CD44V6-Specific SCFV:zeta-Chimera" Int J. Cancer (1996) vol. 68 pp. 232-238.
Ho et al., "Adoptive immunotherapy: Engineering T cell responses as biological weapons for tumor mass destruction" Cancer Cell (2003) vol. 3 pp. 431-437.
Hollyman et al. "Manufacturing validation of biologically functional T cells targeted to CD19 antigen for autologous adoptive cell therapy" J Immunother (2009) vol. 32 No. 2 pp. 169-180.
Homback et al., "The Recombinant T Cell Receptor Strategy: Insights into Structure and Function of Recombinant Immunoreceptors on the Way Towards an Optimal Receptor Design for Cellular Immunotherapy," Current Gene Therapy 2: 211-226 (2002).
Hoyos et al. "Engineering CD19-specific T lymphocytes with interleukin-15 and a suicide gene to enhance their anti-lymphoma/leukemia effects and safety", Leukemia, vol. 24, No. 6, Apr. 29, 2010, pp. 1160-1170.
Imai et al., "Chimeric receptors with 4-1BB signaling capacity provoke potent cytotoxicity against acute lymphoblastic leukemia," Leukemia 18: 676-684 (2004).
Imai et al., "Genetic modification of primary natural killer cells overcomes inhibitory signals and induces specific killing of leukemic cells" Blood (2005) vol. 106 No. 1 pp. 376-383.
International Search Report from PCT/US2011/064191 dated Jan. 5, 2012.
Irving et al., "The cytoplasmic domain of the T cell receptor zeta chain is sufficient to couple to receptor-associated signal transduction pathways," Cell 64: 891-901 (1991).
Jena, Bipulendu et al. "Redirecting T-cell specificity by introducing a tumor-specific chimeric antigen receptor, Blood, May 3, 2010", vol. 116, No. 7, pp. 1035-1044.
Jensen et al., "Anti-Transgene Rejection Responses Contribute to Attenuated Persistence of Adoptively Transferred CD20/CD19-Specific Chimeric Antigen Receptor Re-directed T Cells in Humans" Biol Blood Marrow Transplant (2010) vol. 16 No. 9 pp. 1245-1256.
Johnson et al., "Gene therapy with human and mouse T-cell receptors mediates cancer regression and targets hormal tissues expressing cognate antigen" Blood (2009) vol. 114 No. 3 pp. 535-545.
June et al., "Engineering lymphocyte subsets: tools, trials and tribulations" Nat Rev Immunol (2009) vol. 9 No. 10 pp. 704-716.
Kalos et al. "Adoptive T Cell Transfer for Cancer Immunotherapy in the Era of Synthetic Biology", Immunity, Cell Press, US, vol. 39, No. 1, Jul. 25, 2013. pp. 49-60.
Kalos et al. "T Cells with Chimeric Antigen Receptors Have Potent Antitumor Effects and Can Establish Memory in Patients with Advanced Leukemia", Science Translation Medicine (2011) vol. 3 No. 95 95ra73.

* cited by examiner

Targets for RNA engineering

Costimulation

CD70, CD83
CD80, CD86
CD40, CD154
CD137L (4-1BBL)
CD252 (OX40L)
CD275 (ICOS-L)
CD54 (ICAM-1)
CD49a, CD43
CD127
CD150 (SLAM), CD160
IL-4R
GITR-L, CD265 (RANK)
CD270 (HVEM), CD258 (LIGHT)
TIM-4, TL1A
CD153 (CD30L)
CD200R (OX2R)
CD48, CD244
CD112 (PVRL2), CD155 (PVR)

Soluble

IL-2
IL-12
IL-6
IL-7
IL-15
IL-18
GM-CSF

IL-18
IL-21
IL-27

Ag Presentation

CD64
MHC I
MHC II

Trafficking/migration

CD183 (CXCR3)
CCR2, CCR6
CD50 (ICAM-3)
CD197 (CCR7)
CD58 (LFA-3)
CD62L

DC Targeting

TLR Ligands
anti-DEC-205
anti-DC-SIGN

Fig. 1

SEQUENCE LISTING

```
<160> NUMBER OF SEQ ID NOS: 54

<210> SEQ ID NO 1
<211> LENGTH: 1184
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 1

cgtgaggctc cggtgcccgt cagtgggcag agcgcacatc gcccacagtc cccgagaagt     60

tggggggagg ggtcggcaat tgaaccggtg cctagagaag gtggcgcggg gtaaactggg    120

aaagtgatgt cgtgtactgg ctccgccttt ttcccgaggg tgggggagaa ccgtatataa    180

gtgcagtagt cgccgtgaac gttctttttc gcaacgggtt tgccgccaga acacaggtaa    240

gtgccgtgtg tggttcccgc gggcctggcc tctttacggg ttatggccct tgcgtgcctt    300

gaattacttc cacctggctg cagtacgtga ttcttgatcc cgagcttcgg gttggaagtg    360

ggtgggagag ttcgaggcct tgcgcttaag gagccccttc gcctcgtgct tgagttgagg    420

cctggcctgg gcgctggggc cgccgcgtgc gaatctggtg gcaccttcgc gcctgtctcg    480

ctgctttcga taagtctcta gccatttaaa atttttgatg acctgctgcg acgctttttt    540

tctggcaaga tagtcttgta aatgcgggcc aagatctgca cactggtatt tcggtttttg    600

gggccgcggg cggcgacggg gcccgtgcgt cccagcgcac atgttcggcg aggcggggcc    660

tgcgagcgcg gccaccgaga atcggacggg ggtagtctca agctggccgg cctgctctgg    720

tgcctggcct cgcgccgccg tgtatcgccc cgccctgggc ggcaaggctg gcccggtcgg    780

caccagttgc gtgagcggaa agatggccgc ttcccggccc tgctgcaggg agctcaaaat    840

ggaggacgcg gcgctcggga gagcgggcgg gtgagtcacc cacacaaagg aaaagggcct    900

ttccgtcctc agccgtcgct tcatgtgact ccacggagta ccgggcgccg tccaggcacc    960

tcgattagtt ctcgagcttt tggagtacgt cgtctttagg ttggggggag gggttttatg   1020

cgatggagtt tccccacact gagtgggtgg agactgaagt taggccagct tggcacttga   1080

tgtaattctc cttggaattt gccctttttg agtttggatc ttggttcatt ctcaagcctc   1140

agacagtggt tcaaagtttt tttcttccat ttcaggtgtc gtga                    1184


<210> SEQ ID NO 2
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2
```

Met Ala Leu Pro Val Thr Ala Leu Leu Leu Pro Leu Ala Leu Leu Leu
1 5 10 15

His Ala Ala Arg Pro
20

<210> SEQ ID NO 3
<211> LENGTH: 63
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 3
atggccctgc ctgtgacagc cctgctgctg cctctggctc tgctgctgca tgccgctaga 60
ccc 63

<210> SEQ ID NO 4
<211> LENGTH: 45
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 4

Thr Thr Thr Pro Ala Pro Arg Pro Pro Thr Pro Ala Pro Thr Ile Ala
1 5 10 15

Ser Gln Pro Leu Ser Leu Arg Pro Glu Ala Cys Arg Pro Ala Ala Gly
20 25 30

Gly Ala Val His Thr Arg Gly Leu Asp Phe Ala Cys Asp
35 40 45

<210> SEQ ID NO 5
<211> LENGTH: 135
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 5
accacgacgc cagcgccgcg accaccaaca ccggcgccca ccatcgcgtc gcagcccctg 60
tccctgcgcc cagaggcgtg ccggccagcg gcggggggcg cagtgcacac gagggggctg 120
gacttcgcct gtgat 135

<210> SEQ ID NO 6
<211> LENGTH: 230
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 6

Glu Ser Lys Tyr Gly Pro Pro Cys Pro Pro Cys Pro Ala Pro Glu Phe
1 5 10 15

Leu Gly Gly Pro Ser Val Phe Leu Phe Pro Pro Lys Pro Lys Asp Thr
20 25 30

-continued

```
Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys Met
225                 230

<210> SEQ ID NO 7
<211> LENGTH: 690
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 7

gagagcaagt acggccctcc ctgcccccct tgccctgccc ccgagttcct gggcggaccc      60

agcgtgttcc tgttcccccc caagcccaag gacaccctga tgatcagccg gacccccgag     120

gtgacctgtg tggtggtgga cgtgtcccag gaggaccccg aggtccagtt caactggtac     180

gtggacggcg tggaggtgca caacgccaag accaagcccc gggaggagca gttcaatagc     240

acctaccggg tggtgtccgt gctgaccgtg ctgcaccagg actggctgaa cggcaaggaa     300

tacaagtgta aggtgtccaa caagggcctg cccagcagca tcgagaaaac catcagcaag     360

gccaagggcc agcctcggga gccccaggtg tacaccctgc cccctagcca agaggagatg     420

accaagaacc aggtgtccct gacctgcctg gtgaagggct tctaccccag cgacatcgcc     480

gtggagtggg agagcaacgg ccagcccgag aacaactaca agaccacccc ccctgtgctg     540

gacagcgacg gcagcttctt cctgtacagc cggctgaccg tggacaagag ccggtggcag     600

gagggcaacg tctttagctg ctccgtgatg cacgaggccc tgcacaacca ctacacccag     660

aagagcctga gcctgtccct gggcaagatg                                      690

<210> SEQ ID NO 8
<211> LENGTH: 282
```

<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 8

```
Arg Trp Pro Glu Ser Pro Lys Ala Gln Ala Ser Ser Val Pro Thr Ala
1               5                   10                  15

Gln Pro Gln Ala Glu Gly Ser Leu Ala Lys Ala Thr Thr Ala Pro Ala
            20                  25                  30

Thr Thr Arg Asn Thr Gly Arg Gly Gly Glu Glu Lys Lys Lys Glu Lys
        35                  40                  45

Glu Lys Glu Glu Gln Glu Glu Arg Glu Thr Lys Thr Pro Glu Cys Pro
    50                  55                  60

Ser His Thr Gln Pro Leu Gly Val Tyr Leu Leu Thr Pro Ala Val Gln
65                  70                  75                  80

Asp Leu Trp Leu Arg Asp Lys Ala Thr Phe Thr Cys Phe Val Val Gly
                85                  90                  95

Ser Asp Leu Lys Asp Ala His Leu Thr Trp Glu Val Ala Gly Lys Val
            100                 105                 110

Pro Thr Gly Gly Val Glu Glu Gly Leu Leu Glu Arg His Ser Asn Gly
        115                 120                 125

Ser Gln Ser Gln His Ser Arg Leu Thr Leu Pro Arg Ser Leu Trp Asn
    130                 135                 140

Ala Gly Thr Ser Val Thr Cys Thr Leu Asn His Pro Ser Leu Pro Pro
145                 150                 155                 160

Gln Arg Leu Met Ala Leu Arg Glu Pro Ala Ala Gln Ala Pro Val Lys
                165                 170                 175

Leu Ser Leu Asn Leu Leu Ala Ser Ser Asp Pro Pro Glu Ala Ala Ser
            180                 185                 190

Trp Leu Leu Cys Glu Val Ser Gly Phe Ser Pro Pro Asn Ile Leu Leu
        195                 200                 205

Met Trp Leu Glu Asp Gln Arg Glu Val Asn Thr Ser Gly Phe Ala Pro
    210                 215                 220

Ala Arg Pro Pro Pro Gln Pro Gly Ser Thr Thr Phe Trp Ala Trp Ser
225                 230                 235                 240

Val Leu Arg Val Pro Ala Pro Pro Ser Pro Gln Pro Ala Thr Tyr Thr
                245                 250                 255

Cys Val Val Ser His Glu Asp Ser Arg Thr Leu Leu Asn Ala Ser Arg
            260                 265                 270

Ser Leu Glu Val Ser Tyr Val Thr Asp His
        275                 280
```

<210> SEQ ID NO 9
<211> LENGTH: 847
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 9

```
aggtggcccg aaagtcccaa ggcccaggca tctagtgttc ctactgcaca gccccaggca      60

gaaggcagcc tagccaaagc tactactgca cctgccacta cgcgcaatac tggccgtggc     120
```

-continued

```
ggggaggaga agaaaaagga gaaagagaaa gaagaacagg aagagaggga gaccaagacc    180

cctgaatgtc catcccatac ccagccgctg ggcgtctatc tcttgactcc cgcagtacag    240

gacttgtggc ttagagataa ggccaccttt acatgtttcg tcgtgggctc tgacctgaag    300

gatgcccatt tgacttggga ggttgccgga aaggtaccca caggggggt tgaggaaggg    360

ttgctggagc gccattccaa tggctctcag agccagcact caagactcac ccttccgaga    420

tccctgtgga acgccgggac ctctgtcaca tgtactctaa atcatcctag cctgcccccca    480

cagcgtctga tggcccttag agagccagcc gcccaggcac cagttaagct tagcctgaat    540

ctgctcgcca gtagtgatcc cccagaggcc gccagctggc tcttatgcga agtgtccggc    600

tttagcccgc ccaacatctt gctcatgtgg ctggaggacc agcgagaagt gaacaccagc    660

ggcttcgctc cagcccggcc cccaccccag ccgggttcta ccacattctg ggcctggagt    720

gtcttaaggg tcccagcacc acctagcccc cagccagcca catacacctg tgttgtgtcc    780

catgaagata gcaggaccct gctaaatgct tctaggagtc tggaggtttc ctacgtgact    840

gaccatt                                                              847


<210> SEQ ID NO 10
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Gly Gly Gly Gly Ser Gly Gly Gly Gly Ser
1               5                   10


<210> SEQ ID NO 11
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 11

ggtggcggag gttctggagg tggaggttcc                                      30


<210> SEQ ID NO 12
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Ile Tyr Ile Trp Ala Pro Leu Ala Gly Thr Cys Gly Val Leu Leu Leu
1               5                   10                  15

Ser Leu Val Ile Thr Leu Tyr Cys
            20


<210> SEQ ID NO 13
<211> LENGTH: 72
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 13

atctacatct gggcgccctt ggccgggact tgtggggtcc ttctcctgtc actggttatc     60

accctttact gc                                                         72


<210> SEQ ID NO 14
<211> LENGTH: 42
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40


<210> SEQ ID NO 15
<211> LENGTH: 126
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 15

aaacggggca gaaagaaact cctgtatata ttcaaacaac catttatgag accagtacaa     60

actactcaag aggaagatgg ctgtagctgc cgatttccag aagaagaaga aggaggatgt    120

gaactg                                                               126


<210> SEQ ID NO 16
<211> LENGTH: 48
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Gln Arg Arg Lys Tyr Arg Ser Asn Lys Gly Glu Ser Pro Val Glu Pro
1               5                   10                  15

Ala Glu Pro Cys Arg Tyr Ser Cys Pro Arg Glu Glu Glu Gly Ser Thr
            20                  25                  30

Ile Pro Ile Gln Glu Asp Tyr Arg Lys Pro Glu Pro Ala Cys Ser Pro
        35                  40                  45


<210> SEQ ID NO 17
<211> LENGTH: 123
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

<400> SEQUENCE: 17
aggagtaaga ggagcaggct cctgcacagt gactacatga acatgactcc ccgccgcccc 60
gggcccaccc gcaagcatta ccagccctat gccccaccac gcgacttcgc agcctatcgc 120
tcc 123

<210> SEQ ID NO 18
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 18

Arg Val Lys Phe Ser Arg Ser Ala Asp Ala Pro Ala Tyr Lys Gln Gly
1 5 10 15

Gln Asn Gln Leu Tyr Asn Glu Leu Asn Leu Gly Arg Arg Glu Glu Tyr
20 25 30

Asp Val Leu Asp Lys Arg Arg Gly Arg Asp Pro Glu Met Gly Gly Lys
35 40 45

Pro Arg Arg Lys Asn Pro Gln Glu Gly Leu Tyr Asn Glu Leu Gln Lys
50 55 60

Asp Lys Met Ala Glu Ala Tyr Ser Glu Ile Gly Met Lys Gly Glu Arg
65 70 75 80

Arg Arg Gly Lys Gly His Asp Gly Leu Tyr Gln Gly Leu Ser Thr Ala
85 90 95

Thr Lys Asp Thr Tyr Asp Ala Leu His Met Gln Ala Leu Pro Pro Arg
100 105 110

<210> SEQ ID NO 19
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 19
agagtgaagt tcagcaggag cgcagacgcc cccgcgtaca agcagggcca gaaccagctc 60
tataacgagc tcaatctagg acgaagagag gagtacgatg ttttggacaa gagacgtggc 120
cgggaccctg agatgggggg aaagccgaga aggaagaacc ctcaggaagg cctgtacaat 180
gaactgcaga aagataagat ggcggaggcc tacagtgaga ttgggatgaa aggcgagcgc 240
cggaggggca aggggcacga tggcctttac cagggtctca gtacagccac caaggacacc 300
tacgacgccc ttcacatgca ggccctgccc cctcgc 336

<210> SEQ ID NO 20
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 20

Arg Val Lys Phe Ser Arg Ser Ala Asp Ala Pro Ala Tyr Gln Gln Gly

-continued

```
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110


<210> SEQ ID NO 21
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 21

agagtgaagt tcagcaggag cgcagacgcc cccgcgtacc agcagggcca gaaccagctc     60

tataacgagc tcaatctagg acgaagagag gagtacgatg ttttggacaa gagacgtggc    120

cgggaccctg agatgggggg aaagccgaga aggaagaacc ctcaggaagg cctgtacaat    180

gaactgcaga aagataagat ggcggaggcc tacagtgaga ttgggatgaa aggcgagcgc    240

cggaggggca aggggcacga tggcctttac cagggtctca gtacagccac caaggacacc    300

tacgacgccc ttcacatgca ggccctgccc cctcgc                              336


<210> SEQ ID NO 22
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Gly Gly Gly Gly Ser
1               5


<210> SEQ ID NO 23
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 23

ggtggcggag gttctggagg tggaggttcc                                      30


<210> SEQ ID NO 24
<211> LENGTH: 40
<212> TYPE: PRT
<213> ORGANISM: Artificial Sequence
<220> FEATURE:
```

<221> NAME/KEY: source
<223> OTHER INFORMATION: /note="Description of Artificial Sequence:
      Synthetic polypeptide"
<220> FEATURE:
<221> NAME/KEY: MISC_FEATURE
<222> LOCATION: (1)..(40)
<223> OTHER INFORMATION: /note="This sequence may encompass 1-10
      repeating "Gly Gly Gly Ser" units"

<400> SEQUENCE: 24

```
Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser
        35                  40
```

<210> SEQ ID NO 25
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

```
Gly Gly Gly Gly Ser Gly Gly Gly Gly Ser Gly Gly Gly Gly Ser Gly
1               5                   10                  15

Gly Gly Gly Ser
            20
```

<210> SEQ ID NO 26
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

```
Gly Gly Gly Gly Ser Gly Gly Gly Gly Ser Gly Gly Gly Gly Ser
1               5                   10                  15
```

<210> SEQ ID NO 27
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

```
Gly Gly Gly Ser
1
```

<210> SEQ ID NO 28
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 28

```
aaaaaaaaaa aaaaaaaaaa aaaaaaaaaa aaaaaaaaaa aaaaaaaaaa aaaaaaaaaa     60
aaaaaaaaaa aaaaaaaaaa aaaaaaaaaa aaaaaaaaaa aaaaaaaaaa aaaaaaaaaa    120
aaaaaaaaaa aaaaaaaaaa aaaaaaaaaa aaaaaaaaaa aaaaaaaaaa aaaaaaaaaa    180
aaaaaaaaaa aaaaaaaaaa aaaaaaaaaa aaaaaaaaaa aaaaaaaaaa aaaaaaaaaa    240
aaaaaaaaaa aaaaaaaaaa aaaaaaaaaa aaaaaaaaaa aaaaaaaaaa aaaaaaaaaa    300
aaaaaaaaaa aaaaaaaaaa aaaaaaaaaa aaaaaaaaaa aaaaaaaaaa aaaaaaaaaa    360
aaaaaaaaaa aaaaaaaaaa aaaaaaaaaa aaaaaaaaaa aaaaaaaaaa aaaaaaaaaa    420
aaaaaaaaaa aaaaaaaaaa aaaaaaaaaa aaaaaaaaaa aaaaaaaaaa aaaaaaaaaa    480
aaaaaaaaaa aaaaaaaaaa aaaaaaaaaa aaaaaaaaaa aaaaaaaaaa aaaaaaaaaa    540
aaaaaaaaaa aaaaaaaaaa aaaaaaaaaa aaaaaaaaaa aaaaaaaaaa aaaaaaaaaa    600
aaaaaaaaaa aaaaaaaaaa aaaaaaaaaa aaaaaaaaaa aaaaaaaaaa aaaaaaaaaa    660
aaaaaaaaaa aaaaaaaaaa aaaaaaaaaa aaaaaaaaaa aaaaaaaaaa aaaaaaaaaa    720
aaaaaaaaaa aaaaaaaaaa aaaaaaaaaa aaaaaaaaaa aaaaaaaaaa aaaaaaaaaa    780
aaaaaaaaaa aaaaaaaaaa aaaaaaaaaa aaaaaaaaaa aaaaaaaaaa aaaaaaaaaa    840
aaaaaaaaaa aaaaaaaaaa aaaaaaaaaa aaaaaaaaaa aaaaaaaaaa aaaaaaaaaa    900
aaaaaaaaaa aaaaaaaaaa aaaaaaaaaa aaaaaaaaaa aaaaaaaaaa aaaaaaaaaa    960
aaaaaaaaaa aaaaaaaaaa aaaaaaaaaa aaaaaaaaaa aaaaaaaaaa aaaaaaaaaa   1020
aaaaaaaaaa aaaaaaaaaa aaaaaaaaaa aaaaaaaaaa aaaaaaaaaa aaaaaaaaaa   1080
aaaaaaaaaa aaaaaaaaaa aaaaaaaaaa aaaaaaaaaa aaaaaaaaaa aaaaaaaaaa   1140
aaaaaaaaaa aaaaaaaaaa aaaaaaaaaa aaaaaaaaaa aaaaaaaaaa aaaaaaaaaa   1200
aaaaaaaaaa aaaaaaaaaa aaaaaaaaaa aaaaaaaaaa aaaaaaaaaa aaaaaaaaaa   1260
aaaaaaaaaa aaaaaaaaaa aaaaaaaaaa aaaaaaaaaa aaaaaaaaaa aaaaaaaaaa   1320
aaaaaaaaaa aaaaaaaaaa aaaaaaaaaa aaaaaaaaaa aaaaaaaaaa aaaaaaaaaa   1380
aaaaaaaaaa aaaaaaaaaa aaaaaaaaaa aaaaaaaaaa aaaaaaaaaa aaaaaaaaaa   1440
aaaaaaaaaa aaaaaaaaaa aaaaaaaaaa aaaaaaaaaa aaaaaaaaaa aaaaaaaaaa   1500
aaaaaaaaaa aaaaaaaaaa aaaaaaaaaa aaaaaaaaaa aaaaaaaaaa aaaaaaaaaa   1560
aaaaaaaaaa aaaaaaaaaa aaaaaaaaaa aaaaaaaaaa aaaaaaaaaa aaaaaaaaaa   1620
aaaaaaaaaa aaaaaaaaaa aaaaaaaaaa aaaaaaaaaa aaaaaaaaaa aaaaaaaaaa   1680
aaaaaaaaaa aaaaaaaaaa aaaaaaaaaa aaaaaaaaaa aaaaaaaaaa aaaaaaaaaa   1740
aaaaaaaaaa aaaaaaaaaa aaaaaaaaaa aaaaaaaaaa aaaaaaaaaa aaaaaaaaaa   1800
aaaaaaaaaa aaaaaaaaaa aaaaaaaaaa aaaaaaaaaa aaaaaaaaaa aaaaaaaaaa   1860
aaaaaaaaaa aaaaaaaaaa aaaaaaaaaa aaaaaaaaaa aaaaaaaaaa aaaaaaaaaa   1920
aaaaaaaaaa aaaaaaaaaa aaaaaaaaaa aaaaaaaaaa aaaaaaaaaa aaaaaaaaaa   1980
aaaaaaaaaa aaaaaaaaaa                                               2000
```

<210> SEQ ID NO 29
<211> LENGTH: 150
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 29
aaaaaaaaaa aaaaaaaaaa aaaaaaaaaa aaaaaaaaaa aaaaaaaaaa aaaaaaaaaa 60
aaaaaaaaaa aaaaaaaaaa aaaaaaaaaa aaaaaaaaaa aaaaaaaaaa aaaaaaaaaa 120
aaaaaaaaaa aaaaaaaaaa aaaaaaaaaa 150

<210> SEQ ID NO 30
<211> LENGTH: 5000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 30
aaaaaaaaaa aaaaaaaaaa aaaaaaaaaa aaaaaaaaaa aaaaaaaaaa aaaaaaaaaa 60
aaaaaaaaaa aaaaaaaaaa aaaaaaaaaa aaaaaaaaaa aaaaaaaaaa aaaaaaaaaa 120
aaaaaaaaaa aaaaaaaaaa aaaaaaaaaa aaaaaaaaaa aaaaaaaaaa aaaaaaaaaa 180
aaaaaaaaaa aaaaaaaaaa aaaaaaaaaa aaaaaaaaaa aaaaaaaaaa aaaaaaaaaa 240
aaaaaaaaaa aaaaaaaaaa aaaaaaaaaa aaaaaaaaaa aaaaaaaaaa aaaaaaaaaa 300
aaaaaaaaaa aaaaaaaaaa aaaaaaaaaa aaaaaaaaaa aaaaaaaaaa aaaaaaaaaa 360
aaaaaaaaaa aaaaaaaaaa aaaaaaaaaa aaaaaaaaaa aaaaaaaaaa aaaaaaaaaa 420
aaaaaaaaaa aaaaaaaaaa aaaaaaaaaa aaaaaaaaaa aaaaaaaaaa aaaaaaaaaa 480
aaaaaaaaaa aaaaaaaaaa aaaaaaaaaa aaaaaaaaaa aaaaaaaaaa aaaaaaaaaa 540
aaaaaaaaaa aaaaaaaaaa aaaaaaaaaa aaaaaaaaaa aaaaaaaaaa aaaaaaaaaa 600
aaaaaaaaaa aaaaaaaaaa aaaaaaaaaa aaaaaaaaaa aaaaaaaaaa aaaaaaaaaa 660
aaaaaaaaaa aaaaaaaaaa aaaaaaaaaa aaaaaaaaaa aaaaaaaaaa aaaaaaaaaa 720
aaaaaaaaaa aaaaaaaaaa aaaaaaaaaa aaaaaaaaaa aaaaaaaaaa aaaaaaaaaa 780
aaaaaaaaaa aaaaaaaaaa aaaaaaaaaa aaaaaaaaaa aaaaaaaaaa aaaaaaaaaa 840
aaaaaaaaaa aaaaaaaaaa aaaaaaaaaa aaaaaaaaaa aaaaaaaaaa aaaaaaaaaa 900
aaaaaaaaaa aaaaaaaaaa aaaaaaaaaa aaaaaaaaaa aaaaaaaaaa aaaaaaaaaa 960
aaaaaaaaaa aaaaaaaaaa aaaaaaaaaa aaaaaaaaaa aaaaaaaaaa aaaaaaaaaa 1020
aaaaaaaaaa aaaaaaaaaa aaaaaaaaaa aaaaaaaaaa aaaaaaaaaa aaaaaaaaaa 1080
aaaaaaaaaa aaaaaaaaaa aaaaaaaaaa aaaaaaaaaa aaaaaaaaaa aaaaaaaaaa 1140
aaaaaaaaaa aaaaaaaaaa aaaaaaaaaa aaaaaaaaaa aaaaaaaaaa aaaaaaaaaa 1200
aaaaaaaaaa aaaaaaaaaa aaaaaaaaaa aaaaaaaaaa aaaaaaaaaa aaaaaaaaaa 1260
aaaaaaaaaa aaaaaaaaaa aaaaaaaaaa aaaaaaaaaa aaaaaaaaaa aaaaaaaaaa 1320
aaaaaaaaaa aaaaaaaaaa aaaaaaaaaa aaaaaaaaaa aaaaaaaaaa aaaaaaaaaa 1380
aaaaaaaaaa aaaaaaaaaa aaaaaaaaaa aaaaaaaaaa aaaaaaaaaa aaaaaaaaaa 1440
aaaaaaaaaa aaaaaaaaaa aaaaaaaaaa aaaaaaaaaa aaaaaaaaaa aaaaaaaaaa 1500
aaaaaaaaaa aaaaaaaaaa aaaaaaaaaa aaaaaaaaaa aaaaaaaaaa aaaaaaaaaa 1560
aaaaaaaaaa aaaaaaaaaa aaaaaaaaaa aaaaaaaaaa aaaaaaaaaa aaaaaaaaaa 1620
aaaaaaaaaa aaaaaaaaaa aaaaaaaaaa aaaaaaaaaa aaaaaaaaaa aaaaaaaaaa 1680
aaaaaaaaaa aaaaaaaaaa aaaaaaaaaa aaaaaaaaaa aaaaaaaaaa aaaaaaaaaa 1740
aaaaaaaaaa aaaaaaaaaa aaaaaaaaaa aaaaaaaaaa aaaaaaaaaa aaaaaaaaaa 1800
aaaaaaaaaa aaaaaaaaaa aaaaaaaaaa aaaaaaaaaa aaaaaaaaaa aaaaaaaaaa 1860
aaaaaaaaaa aaaaaaaaaa aaaaaaaaaa aaaaaaaaaa aaaaaaaaaa aaaaaaaaaa 1920
aaaaaaaaaa aaaaaaaaaa aaaaaaaaaa aaaaaaaaaa aaaaaaaaaa aaaaaaaaaa 1980
aaaaaaaaaa aaaaaaaaaa aaaaaaaaaa aaaaaaaaaa aaaaaaaaaa aaaaaaaaaa 2040
aaaaaaaaaa aaaaaaaaaa aaaaaaaaaa aaaaaaaaaa aaaaaaaaaa aaaaaaaaaa 2100
aaaaaaaaaa aaaaaaaaaa aaaaaaaaaa aaaaaaaaaa aaaaaaaaaa aaaaaaaaaa 2160
aaaaaaaaaa aaaaaaaaaa aaaaaaaaaa aaaaaaaaaa aaaaaaaaaa aaaaaaaaaa 2220
aaaaaaaaaa aaaaaaaaaa aaaaaaaaaa aaaaaaaaaa aaaaaaaaaa aaaaaaaaaa 2280
aaaaaaaaaa aaaaaaaaaa aaaaaaaaaa aaaaaaaaaa aaaaaaaaaa aaaaaaaaaa 2340
aaaaaaaaaa aaaaaaaaaa aaaaaaaaaa aaaaaaaaaa aaaaaaaaaa aaaaaaaaaa 2400
aaaaaaaaaa aaaaaaaaaa aaaaaaaaaa aaaaaaaaaa aaaaaaaaaa aaaaaaaaaa 2460
aaaaaaaaaa aaaaaaaaaa aaaaaaaaaa aaaaaaaaaa aaaaaaaaaa aaaaaaaaaa 2520
aaaaaaaaaa aaaaaaaaaa aaaaaaaaaa aaaaaaaaaa aaaaaaaaaa aaaaaaaaaa 2580
aaaaaaaaaa aaaaaaaaaa aaaaaaaaaa aaaaaaaaaa aaaaaaaaaa aaaaaaaaaa 2640
aaaaaaaaaa aaaaaaaaaa aaaaaaaaaa aaaaaaaaaa aaaaaaaaaa aaaaaaaaaa 2700
aaaaaaaaaa aaaaaaaaaa aaaaaaaaaa aaaaaaaaaa aaaaaaaaaa aaaaaaaaaa 2760
aaaaaaaaaa aaaaaaaaaa aaaaaaaaaa aaaaaaaaaa aaaaaaaaaa aaaaaaaaaa 2820
aaaaaaaaaa aaaaaaaaaa aaaaaaaaaa aaaaaaaaaa aaaaaaaaaa aaaaaaaaaa 2880
aaaaaaaaaa aaaaaaaaaa aaaaaaaaaa aaaaaaaaaa aaaaaaaaaa aaaaaaaaaa 2940
aaaaaaaaaa aaaaaaaaaa aaaaaaaaaa aaaaaaaaaa aaaaaaaaaa aaaaaaaaaa 3000
aaaaaaaaaa aaaaaaaaaa aaaaaaaaaa aaaaaaaaaa aaaaaaaaaa aaaaaaaaaa 3060
aaaaaaaaaa aaaaaaaaaa aaaaaaaaaa aaaaaaaaaa aaaaaaaaaa aaaaaaaaaa 3120
aaaaaaaaaa aaaaaaaaaa aaaaaaaaaa aaaaaaaaaa aaaaaaaaaa aaaaaaaaaa 3180
aaaaaaaaaa aaaaaaaaaa aaaaaaaaaa aaaaaaaaaa aaaaaaaaaa aaaaaaaaaa 3240
aaaaaaaaaa aaaaaaaaaa aaaaaaaaaa aaaaaaaaaa aaaaaaaaaa aaaaaaaaaa 3300
aaaaaaaaaa aaaaaaaaaa aaaaaaaaaa aaaaaaaaaa aaaaaaaaaa aaaaaaaaaa 3360
aaaaaaaaaa aaaaaaaaaa aaaaaaaaaa aaaaaaaaaa aaaaaaaaaa aaaaaaaaaa 3420
aaaaaaaaaa aaaaaaaaaa aaaaaaaaaa aaaaaaaaaa aaaaaaaaaa aaaaaaaaaa 3480
aaaaaaaaaa aaaaaaaaaa aaaaaaaaaa aaaaaaaaaa aaaaaaaaaa aaaaaaaaaa 3540
aaaaaaaaaa aaaaaaaaaa aaaaaaaaaa aaaaaaaaaa aaaaaaaaaa aaaaaaaaaa 3600
aaaaaaaaaa aaaaaaaaaa aaaaaaaaaa aaaaaaaaaa aaaaaaaaaa aaaaaaaaaa 3660
aaaaaaaaaa aaaaaaaaaa aaaaaaaaaa aaaaaaaaaa aaaaaaaaaa aaaaaaaaaa 3720
aaaaaaaaaa aaaaaaaaaa aaaaaaaaaa aaaaaaaaaa aaaaaaaaaa aaaaaaaaaa 3780
aaaaaaaaaa aaaaaaaaaa aaaaaaaaaa aaaaaaaaaa aaaaaaaaaa aaaaaaaaaa 3840
aaaaaaaaaa aaaaaaaaaa aaaaaaaaaa aaaaaaaaaa aaaaaaaaaa aaaaaaaaaa 3900
aaaaaaaaaa aaaaaaaaaa aaaaaaaaaa aaaaaaaaaa aaaaaaaaaa aaaaaaaaaa 3960
aaaaaaaaaa aaaaaaaaaa aaaaaaaaaa aaaaaaaaaa aaaaaaaaaa aaaaaaaaaa 4020
aaaaaaaaaa aaaaaaaaaa aaaaaaaaaa aaaaaaaaaa aaaaaaaaaa aaaaaaaaaa 4080
aaaaaaaaaa aaaaaaaaaa aaaaaaaaaa aaaaaaaaaa aaaaaaaaaa aaaaaaaaaa 4140
aaaaaaaaaa aaaaaaaaaa aaaaaaaaaa aaaaaaaaaa aaaaaaaaaa aaaaaaaaaa 4200
aaaaaaaaaa aaaaaaaaaa aaaaaaaaaa aaaaaaaaaa aaaaaaaaaa aaaaaaaaaa 4260
aaaaaaaaaa aaaaaaaaaa aaaaaaaaaa aaaaaaaaaa aaaaaaaaaa aaaaaaaaaa 4320
aaaaaaaaaa aaaaaaaaaa aaaaaaaaaa aaaaaaaaaa aaaaaaaaaa aaaaaaaaaa 4380
aaaaaaaaaa aaaaaaaaaa aaaaaaaaaa aaaaaaaaaa aaaaaaaaaa aaaaaaaaaa 4440
aaaaaaaaaa aaaaaaaaaa aaaaaaaaaa aaaaaaaaaa aaaaaaaaaa aaaaaaaaaa 4500
aaaaaaaaaa aaaaaaaaaa aaaaaaaaaa aaaaaaaaaa aaaaaaaaaa aaaaaaaaaa 4560
aaaaaaaaaa aaaaaaaaaa aaaaaaaaaa aaaaaaaaaa aaaaaaaaaa aaaaaaaaaa 4620
aaaaaaaaaa aaaaaaaaaa aaaaaaaaaa aaaaaaaaaa aaaaaaaaaa aaaaaaaaaa 4680
aaaaaaaaaa aaaaaaaaaa aaaaaaaaaa aaaaaaaaaa aaaaaaaaaa aaaaaaaaaa 4740
aaaaaaaaaa aaaaaaaaaa aaaaaaaaaa aaaaaaaaaa aaaaaaaaaa aaaaaaaaaa 4800
aaaaaaaaaa aaaaaaaaaa aaaaaaaaaa aaaaaaaaaa aaaaaaaaaa aaaaaaaaaa 4860
aaaaaaaaaa aaaaaaaaaa aaaaaaaaaa aaaaaaaaaa aaaaaaaaaa aaaaaaaaaa 4920
aaaaaaaaaa aaaaaaaaaa aaaaaaaaaa aaaaaaaaaa aaaaaaaaaa aaaaaaaaaa 4980
aaaaaaaaaa aaaaaaaaaa 5000

<210> SEQ ID NO 31
<211> LENGTH: 100
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 31
tttttttttt tttttttttt tttttttttt tttttttttt tttttttttt tttttttttt 60
tttttttttt tttttttttt tttttttttt tttttttttt 100

<210> SEQ ID NO 32
<211> LENGTH: 5000
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 32
tttttttttt tttttttttt tttttttttt tttttttttt tttttttttt tttttttttt 60
tttttttttt tttttttttt tttttttttt tttttttttt tttttttttt tttttttttt 120
tttttttttt tttttttttt tttttttttt tttttttttt tttttttttt tttttttttt 180
tttttttttt tttttttttt tttttttttt tttttttttt tttttttttt tttttttttt 240
tttttttttt tttttttttt tttttttttt tttttttttt tttttttttt tttttttttt 300
tttttttttt tttttttttt tttttttttt tttttttttt tttttttttt tttttttttt 360
tttttttttt tttttttttt tttttttttt tttttttttt tttttttttt tttttttttt 420
tttttttttt tttttttttt tttttttttt tttttttttt tttttttttt tttttttttt 480
tttttttttt tttttttttt tttttttttt tttttttttt tttttttttt tttttttttt 540
tttttttttt tttttttttt tttttttttt tttttttttt tttttttttt tttttttttt 600
tttttttttt tttttttttt tttttttttt tttttttttt tttttttttt tttttttttt 660

-continued

```
tttttttttt tttttttttt tttttttttt tttttttttt tttttttttt tttttttttt    720
tttttttttt tttttttttt tttttttttt tttttttttt tttttttttt tttttttttt    780
tttttttttt tttttttttt tttttttttt tttttttttt tttttttttt tttttttttt    840
tttttttttt tttttttttt tttttttttt tttttttttt tttttttttt tttttttttt    900
tttttttttt tttttttttt tttttttttt tttttttttt tttttttttt tttttttttt    960
tttttttttt tttttttttt tttttttttt tttttttttt tttttttttt tttttttttt   1020
tttttttttt tttttttttt tttttttttt tttttttttt tttttttttt tttttttttt   1080
tttttttttt tttttttttt tttttttttt tttttttttt tttttttttt tttttttttt   1140
tttttttttt tttttttttt tttttttttt tttttttttt tttttttttt tttttttttt   1200
tttttttttt tttttttttt tttttttttt tttttttttt tttttttttt tttttttttt   1260
tttttttttt tttttttttt tttttttttt tttttttttt tttttttttt tttttttttt   1320
tttttttttt tttttttttt tttttttttt tttttttttt tttttttttt tttttttttt   1380
tttttttttt tttttttttt tttttttttt tttttttttt tttttttttt tttttttttt   1440
tttttttttt tttttttttt tttttttttt tttttttttt tttttttttt tttttttttt   1500
tttttttttt tttttttttt tttttttttt tttttttttt tttttttttt tttttttttt   1560
tttttttttt tttttttttt tttttttttt tttttttttt tttttttttt tttttttttt   1620
tttttttttt tttttttttt tttttttttt tttttttttt tttttttttt tttttttttt   1680
tttttttttt tttttttttt tttttttttt tttttttttt tttttttttt tttttttttt   1740
tttttttttt tttttttttt tttttttttt tttttttttt tttttttttt tttttttttt   1800
tttttttttt tttttttttt tttttttttt tttttttttt tttttttttt tttttttttt   1860
tttttttttt tttttttttt tttttttttt tttttttttt tttttttttt tttttttttt   1920
tttttttttt tttttttttt tttttttttt tttttttttt tttttttttt tttttttttt   1980
tttttttttt tttttttttt tttttttttt tttttttttt tttttttttt tttttttttt   2040
tttttttttt tttttttttt tttttttttt tttttttttt tttttttttt tttttttttt   2100
tttttttttt tttttttttt tttttttttt tttttttttt tttttttttt tttttttttt   2160
tttttttttt tttttttttt tttttttttt tttttttttt tttttttttt tttttttttt   2220
tttttttttt tttttttttt tttttttttt tttttttttt tttttttttt tttttttttt   2280
tttttttttt tttttttttt tttttttttt tttttttttt tttttttttt tttttttttt   2340
tttttttttt tttttttttt tttttttttt tttttttttt tttttttttt tttttttttt   2400
tttttttttt tttttttttt tttttttttt tttttttttt tttttttttt tttttttttt   2460
tttttttttt tttttttttt tttttttttt tttttttttt tttttttttt tttttttttt   2520
tttttttttt tttttttttt tttttttttt tttttttttt tttttttttt tttttttttt   2580
tttttttttt tttttttttt tttttttttt tttttttttt tttttttttt tttttttttt   2640
tttttttttt tttttttttt tttttttttt tttttttttt tttttttttt tttttttttt   2700
tttttttttt tttttttttt tttttttttt tttttttttt tttttttttt tttttttttt   2760
tttttttttt tttttttttt tttttttttt tttttttttt tttttttttt tttttttttt   2820
tttttttttt tttttttttt tttttttttt tttttttttt tttttttttt tttttttttt   2880
tttttttttt tttttttttt tttttttttt tttttttttt tttttttttt tttttttttt   2940
tttttttttt tttttttttt tttttttttt tttttttttt tttttttttt tttttttttt   3000
```

tttttttttt tttttttttt tttttttttt tttttttttt tttttttttt tttttttttt 3060
tttttttttt tttttttttt tttttttttt tttttttttt tttttttttt tttttttttt 3120
tttttttttt tttttttttt tttttttttt tttttttttt tttttttttt tttttttttt 3180
tttttttttt tttttttttt tttttttttt tttttttttt tttttttttt tttttttttt 3240
tttttttttt tttttttttt tttttttttt tttttttttt tttttttttt tttttttttt 3300
tttttttttt tttttttttt tttttttttt tttttttttt tttttttttt tttttttttt 3360
tttttttttt tttttttttt tttttttttt tttttttttt tttttttttt tttttttttt 3420
tttttttttt tttttttttt tttttttttt tttttttttt tttttttttt tttttttttt 3480
tttttttttt tttttttttt tttttttttt tttttttttt tttttttttt tttttttttt 3540
tttttttttt tttttttttt tttttttttt tttttttttt tttttttttt tttttttttt 3600
tttttttttt tttttttttt tttttttttt tttttttttt tttttttttt tttttttttt 3660
tttttttttt tttttttttt tttttttttt tttttttttt tttttttttt tttttttttt 3720
tttttttttt tttttttttt tttttttttt tttttttttt tttttttttt tttttttttt 3780
tttttttttt tttttttttt tttttttttt tttttttttt tttttttttt tttttttttt 3840
tttttttttt tttttttttt tttttttttt tttttttttt tttttttttt tttttttttt 3900
tttttttttt tttttttttt tttttttttt tttttttttt tttttttttt tttttttttt 3960
tttttttttt tttttttttt tttttttttt tttttttttt tttttttttt tttttttttt 4020
tttttttttt tttttttttt tttttttttt tttttttttt tttttttttt tttttttttt 4080
tttttttttt tttttttttt tttttttttt tttttttttt tttttttttt tttttttttt 4140
tttttttttt tttttttttt tttttttttt tttttttttt tttttttttt tttttttttt 4200
tttttttttt tttttttttt tttttttttt tttttttttt tttttttttt tttttttttt 4260
tttttttttt tttttttttt tttttttttt tttttttttt tttttttttt tttttttttt 4320
tttttttttt tttttttttt tttttttttt tttttttttt tttttttttt tttttttttt 4380
tttttttttt tttttttttt tttttttttt tttttttttt tttttttttt tttttttttt 4440
tttttttttt tttttttttt tttttttttt tttttttttt tttttttttt tttttttttt 4500
tttttttttt tttttttttt tttttttttt tttttttttt tttttttttt tttttttttt 4560
tttttttttt tttttttttt tttttttttt tttttttttt tttttttttt tttttttttt 4620
tttttttttt tttttttttt tttttttttt tttttttttt tttttttttt tttttttttt 4680
tttttttttt tttttttttt tttttttttt tttttttttt tttttttttt tttttttttt 4740
tttttttttt tttttttttt tttttttttt tttttttttt tttttttttt tttttttttt 4800
tttttttttt tttttttttt tttttttttt tttttttttt tttttttttt tttttttttt 4860
tttttttttt tttttttttt tttttttttt tttttttttt tttttttttt tttttttttt 4920
tttttttttt tttttttttt tttttttttt tttttttttt tttttttttt tttttttttt 4980
tttttttttt tttttttttt 5000

<210> SEQ ID NO 33
<211> LENGTH: 5000
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 33

-continued aaaaaaaaaa aaaaaaaaaa aaaaaaaaaa aaaaaaaaaa aaaaaaaaaa aaaaaaaaaa 60
aaaaaaaaaa aaaaaaaaaa aaaaaaaaaa aaaaaaaaaa aaaaaaaaaa aaaaaaaaaa 120
aaaaaaaaaa aaaaaaaaaa aaaaaaaaaa aaaaaaaaaa aaaaaaaaaa aaaaaaaaaa 180
aaaaaaaaaa aaaaaaaaaa aaaaaaaaaa aaaaaaaaaa aaaaaaaaaa aaaaaaaaaa 240
aaaaaaaaaa aaaaaaaaaa aaaaaaaaaa aaaaaaaaaa aaaaaaaaaa aaaaaaaaaa 300
aaaaaaaaaa aaaaaaaaaa aaaaaaaaaa aaaaaaaaaa aaaaaaaaaa aaaaaaaaaa 360
aaaaaaaaaa aaaaaaaaaa aaaaaaaaaa aaaaaaaaaa aaaaaaaaaa aaaaaaaaaa 420
aaaaaaaaaa aaaaaaaaaa aaaaaaaaaa aaaaaaaaaa aaaaaaaaaa aaaaaaaaaa 480
aaaaaaaaaa aaaaaaaaaa aaaaaaaaaa aaaaaaaaaa aaaaaaaaaa aaaaaaaaaa 540
aaaaaaaaaa aaaaaaaaaa aaaaaaaaaa aaaaaaaaaa aaaaaaaaaa aaaaaaaaaa 600
aaaaaaaaaa aaaaaaaaaa aaaaaaaaaa aaaaaaaaaa aaaaaaaaaa aaaaaaaaaa 660
aaaaaaaaaa aaaaaaaaaa aaaaaaaaaa aaaaaaaaaa aaaaaaaaaa aaaaaaaaaa 720
aaaaaaaaaa aaaaaaaaaa aaaaaaaaaa aaaaaaaaaa aaaaaaaaaa aaaaaaaaaa 780
aaaaaaaaaa aaaaaaaaaa aaaaaaaaaa aaaaaaaaaa aaaaaaaaaa aaaaaaaaaa 840
aaaaaaaaaa aaaaaaaaaa aaaaaaaaaa aaaaaaaaaa aaaaaaaaaa aaaaaaaaaa 900
aaaaaaaaaa aaaaaaaaaa aaaaaaaaaa aaaaaaaaaa aaaaaaaaaa aaaaaaaaaa 960
aaaaaaaaaa aaaaaaaaaa aaaaaaaaaa aaaaaaaaaa aaaaaaaaaa aaaaaaaaaa 1020
aaaaaaaaaa aaaaaaaaaa aaaaaaaaaa aaaaaaaaaa aaaaaaaaaa aaaaaaaaaa 1080
aaaaaaaaaa aaaaaaaaaa aaaaaaaaaa aaaaaaaaaa aaaaaaaaaa aaaaaaaaaa 1140
aaaaaaaaaa aaaaaaaaaa aaaaaaaaaa aaaaaaaaaa aaaaaaaaaa aaaaaaaaaa 1200
aaaaaaaaaa aaaaaaaaaa aaaaaaaaaa aaaaaaaaaa aaaaaaaaaa aaaaaaaaaa 1260
aaaaaaaaaa aaaaaaaaaa aaaaaaaaaa aaaaaaaaaa aaaaaaaaaa aaaaaaaaaa 1320
aaaaaaaaaa aaaaaaaaaa aaaaaaaaaa aaaaaaaaaa aaaaaaaaaa aaaaaaaaaa 1380
aaaaaaaaaa aaaaaaaaaa aaaaaaaaaa aaaaaaaaaa aaaaaaaaaa aaaaaaaaaa 1440
aaaaaaaaaa aaaaaaaaaa aaaaaaaaaa aaaaaaaaaa aaaaaaaaaa aaaaaaaaaa 1500
aaaaaaaaaa aaaaaaaaaa aaaaaaaaaa aaaaaaaaaa aaaaaaaaaa aaaaaaaaaa 1560
aaaaaaaaaa aaaaaaaaaa aaaaaaaaaa aaaaaaaaaa aaaaaaaaaa aaaaaaaaaa 1620
aaaaaaaaaa aaaaaaaaaa aaaaaaaaaa aaaaaaaaaa aaaaaaaaaa aaaaaaaaaa 1680
aaaaaaaaaa aaaaaaaaaa aaaaaaaaaa aaaaaaaaaa aaaaaaaaaa aaaaaaaaaa 1740
aaaaaaaaaa aaaaaaaaaa aaaaaaaaaa aaaaaaaaaa aaaaaaaaaa aaaaaaaaaa 1800
aaaaaaaaaa aaaaaaaaaa aaaaaaaaaa aaaaaaaaaa aaaaaaaaaa aaaaaaaaaa 1860
aaaaaaaaaa aaaaaaaaaa aaaaaaaaaa aaaaaaaaaa aaaaaaaaaa aaaaaaaaaa 1920
aaaaaaaaaa aaaaaaaaaa aaaaaaaaaa aaaaaaaaaa aaaaaaaaaa aaaaaaaaaa 1980
aaaaaaaaaa aaaaaaaaaa aaaaaaaaaa aaaaaaaaaa aaaaaaaaaa aaaaaaaaaa 2040
aaaaaaaaaa aaaaaaaaaa aaaaaaaaaa aaaaaaaaaa aaaaaaaaaa aaaaaaaaaa 2100
aaaaaaaaaa aaaaaaaaaa aaaaaaaaaa aaaaaaaaaa aaaaaaaaaa aaaaaaaaaa 2160
aaaaaaaaaa aaaaaaaaaa aaaaaaaaaa aaaaaaaaaa aaaaaaaaaa aaaaaaaaaa 2220
aaaaaaaaaa aaaaaaaaaa aaaaaaaaaa aaaaaaaaaa aaaaaaaaaa aaaaaaaaaa 2280
aaaaaaaaaa aaaaaaaaaa aaaaaaaaaa aaaaaaaaaa aaaaaaaaaa aaaaaaaaaa 2340

-continued

```
aaaaaaaaaa aaaaaaaaaa aaaaaaaaaa aaaaaaaaaa aaaaaaaaaa aaaaaaaaaa   2400
aaaaaaaaaa aaaaaaaaaa aaaaaaaaaa aaaaaaaaaa aaaaaaaaaa aaaaaaaaaa   2460
aaaaaaaaaa aaaaaaaaaa aaaaaaaaaa aaaaaaaaaa aaaaaaaaaa aaaaaaaaaa   2520
aaaaaaaaaa aaaaaaaaaa aaaaaaaaaa aaaaaaaaaa aaaaaaaaaa aaaaaaaaaa   2580
aaaaaaaaaa aaaaaaaaaa aaaaaaaaaa aaaaaaaaaa aaaaaaaaaa aaaaaaaaaa   2640
aaaaaaaaaa aaaaaaaaaa aaaaaaaaaa aaaaaaaaaa aaaaaaaaaa aaaaaaaaaa   2700
aaaaaaaaaa aaaaaaaaaa aaaaaaaaaa aaaaaaaaaa aaaaaaaaaa aaaaaaaaaa   2760
aaaaaaaaaa aaaaaaaaaa aaaaaaaaaa aaaaaaaaaa aaaaaaaaaa aaaaaaaaaa   2820
aaaaaaaaaa aaaaaaaaaa aaaaaaaaaa aaaaaaaaaa aaaaaaaaaa aaaaaaaaaa   2880
aaaaaaaaaa aaaaaaaaaa aaaaaaaaaa aaaaaaaaaa aaaaaaaaaa aaaaaaaaaa   2940
aaaaaaaaaa aaaaaaaaaa aaaaaaaaaa aaaaaaaaaa aaaaaaaaaa aaaaaaaaaa   3000
aaaaaaaaaa aaaaaaaaaa aaaaaaaaaa aaaaaaaaaa aaaaaaaaaa aaaaaaaaaa   3060
aaaaaaaaaa aaaaaaaaaa aaaaaaaaaa aaaaaaaaaa aaaaaaaaaa aaaaaaaaaa   3120
aaaaaaaaaa aaaaaaaaaa aaaaaaaaaa aaaaaaaaaa aaaaaaaaaa aaaaaaaaaa   3180
aaaaaaaaaa aaaaaaaaaa aaaaaaaaaa aaaaaaaaaa aaaaaaaaaa aaaaaaaaaa   3240
aaaaaaaaaa aaaaaaaaaa aaaaaaaaaa aaaaaaaaaa aaaaaaaaaa aaaaaaaaaa   3300
aaaaaaaaaa aaaaaaaaaa aaaaaaaaaa aaaaaaaaaa aaaaaaaaaa aaaaaaaaaa   3360
aaaaaaaaaa aaaaaaaaaa aaaaaaaaaa aaaaaaaaaa aaaaaaaaaa aaaaaaaaaa   3420
aaaaaaaaaa aaaaaaaaaa aaaaaaaaaa aaaaaaaaaa aaaaaaaaaa aaaaaaaaaa   3480
aaaaaaaaaa aaaaaaaaaa aaaaaaaaaa aaaaaaaaaa aaaaaaaaaa aaaaaaaaaa   3540
aaaaaaaaaa aaaaaaaaaa aaaaaaaaaa aaaaaaaaaa aaaaaaaaaa aaaaaaaaaa   3600
aaaaaaaaaa aaaaaaaaaa aaaaaaaaaa aaaaaaaaaa aaaaaaaaaa aaaaaaaaaa   3660
aaaaaaaaaa aaaaaaaaaa aaaaaaaaaa aaaaaaaaaa aaaaaaaaaa aaaaaaaaaa   3720
aaaaaaaaaa aaaaaaaaaa aaaaaaaaaa aaaaaaaaaa aaaaaaaaaa aaaaaaaaaa   3780
aaaaaaaaaa aaaaaaaaaa aaaaaaaaaa aaaaaaaaaa aaaaaaaaaa aaaaaaaaaa   3840
aaaaaaaaaa aaaaaaaaaa aaaaaaaaaa aaaaaaaaaa aaaaaaaaaa aaaaaaaaaa   3900
aaaaaaaaaa aaaaaaaaaa aaaaaaaaaa aaaaaaaaaa aaaaaaaaaa aaaaaaaaaa   3960
aaaaaaaaaa aaaaaaaaaa aaaaaaaaaa aaaaaaaaaa aaaaaaaaaa aaaaaaaaaa   4020
aaaaaaaaaa aaaaaaaaaa aaaaaaaaaa aaaaaaaaaa aaaaaaaaaa aaaaaaaaaa   4080
aaaaaaaaaa aaaaaaaaaa aaaaaaaaaa aaaaaaaaaa aaaaaaaaaa aaaaaaaaaa   4140
aaaaaaaaaa aaaaaaaaaa aaaaaaaaaa aaaaaaaaaa aaaaaaaaaa aaaaaaaaaa   4200
aaaaaaaaaa aaaaaaaaaa aaaaaaaaaa aaaaaaaaaa aaaaaaaaaa aaaaaaaaaa   4260
aaaaaaaaaa aaaaaaaaaa aaaaaaaaaa aaaaaaaaaa aaaaaaaaaa aaaaaaaaaa   4320
aaaaaaaaaa aaaaaaaaaa aaaaaaaaaa aaaaaaaaaa aaaaaaaaaa aaaaaaaaaa   4380
aaaaaaaaaa aaaaaaaaaa aaaaaaaaaa aaaaaaaaaa aaaaaaaaaa aaaaaaaaaa   4440
aaaaaaaaaa aaaaaaaaaa aaaaaaaaaa aaaaaaaaaa aaaaaaaaaa aaaaaaaaaa   4500
aaaaaaaaaa aaaaaaaaaa aaaaaaaaaa aaaaaaaaaa aaaaaaaaaa aaaaaaaaaa   4560
aaaaaaaaaa aaaaaaaaaa aaaaaaaaaa aaaaaaaaaa aaaaaaaaaa aaaaaaaaaa   4620
aaaaaaaaaa aaaaaaaaaa aaaaaaaaaa aaaaaaaaaa aaaaaaaaaa aaaaaaaaaa   4680
aaaaaaaaaa aaaaaaaaaa aaaaaaaaaa aaaaaaaaaa aaaaaaaaaa aaaaaaaaaa   4740
```

```
aaaaaaaaaa aaaaaaaaaa aaaaaaaaaa aaaaaaaaaa aaaaaaaaaa aaaaaaaaaa   4800

aaaaaaaaaa aaaaaaaaaa aaaaaaaaaa aaaaaaaaaa aaaaaaaaaa aaaaaaaaaa   4860

aaaaaaaaaa aaaaaaaaaa aaaaaaaaaa aaaaaaaaaa aaaaaaaaaa aaaaaaaaaa   4920

aaaaaaaaaa aaaaaaaaaa aaaaaaaaaa aaaaaaaaaa aaaaaaaaaa aaaaaaaaaa   4980

aaaaaaaaaa aaaaaaaaaa                                               5000


<210> SEQ ID NO 34
<211> LENGTH: 400
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 34

aaaaaaaaaa aaaaaaaaaa aaaaaaaaaa aaaaaaaaaa aaaaaaaaaa aaaaaaaaaa     60

aaaaaaaaaa aaaaaaaaaa aaaaaaaaaa aaaaaaaaaa aaaaaaaaaa aaaaaaaaaa    120

aaaaaaaaaa aaaaaaaaaa aaaaaaaaaa aaaaaaaaaa aaaaaaaaaa aaaaaaaaaa    180

aaaaaaaaaa aaaaaaaaaa aaaaaaaaaa aaaaaaaaaa aaaaaaaaaa aaaaaaaaaa    240

aaaaaaaaaa aaaaaaaaaa aaaaaaaaaa aaaaaaaaaa aaaaaaaaaa aaaaaaaaaa    300

aaaaaaaaaa aaaaaaaaaa aaaaaaaaaa aaaaaaaaaa aaaaaaaaaa aaaaaaaaaa    360

aaaaaaaaaa aaaaaaaaaa aaaaaaaaaa aaaaaaaaaa                          400


<210> SEQ ID NO 35
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Gly Gly Gly Gly Ser Gly Gly Gly Gly Ser
1               5                   10


<210> SEQ ID NO 36
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 36

ggtggcggag gttctggagg tggaggttcc                                      30


<210> SEQ ID NO 37
<211> LENGTH: 132
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Asp Val Pro Asp Tyr Ala Ser Leu Gly Gly Pro Ser Ser Pro Lys Lys
```

-continued

```
1               5                   10                  15

Lys Arg Lys Val Ser Arg Gly Val Gln Val Glu Thr Ile Ser Pro Gly
            20                  25                  30

Asp Gly Arg Thr Phe Pro Lys Arg Gly Gln Thr Cys Val Val His Tyr
        35                  40                  45

Thr Gly Met Leu Glu Asp Gly Lys Lys Phe Asp Ser Ser Arg Asp Arg
    50                  55                  60

Asn Lys Pro Phe Lys Phe Met Leu Gly Lys Gln Glu Val Ile Arg Gly
65                  70                  75                  80

Trp Glu Glu Gly Val Ala Gln Met Ser Val Gly Gln Arg Ala Lys Leu
                85                  90                  95

Thr Ile Ser Pro Asp Tyr Ala Tyr Gly Ala Thr Gly His Pro Gly Ile
            100                 105                 110

Ile Pro Pro His Ala Thr Leu Val Phe Asp Val Glu Leu Leu Lys Leu
        115                 120                 125

Glu Thr Ser Tyr
    130


<210> SEQ ID NO 38
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Val Gln Val Glu Thr Ile Ser Pro Gly Asp Gly Arg Thr Phe Pro Lys
1               5                   10                  15

Arg Gly Gln Thr Cys Val Val His Tyr Thr Gly Met Leu Glu Asp Gly
            20                  25                  30

Lys Lys Phe Asp Ser Ser Arg Asp Arg Asn Lys Pro Phe Lys Phe Met
        35                  40                  45

Leu Gly Lys Gln Glu Val Ile Arg Gly Trp Glu Glu Gly Val Ala Gln
    50                  55                  60

Met Ser Val Gly Gln Arg Ala Lys Leu Thr Ile Ser Pro Asp Tyr Ala
65                  70                  75                  80

Tyr Gly Ala Thr Gly His Pro Gly Ile Ile Pro Pro His Ala Thr Leu
                85                  90                  95

Val Phe Asp Val Glu Leu Leu Lys Leu Glu Thr Ser
            100                 105


<210> SEQ ID NO 39
<211> LENGTH: 93
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Ile Leu Trp His Glu Met Trp His Glu Gly Leu Glu Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45
```

```
Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Thr Gln Ala
65                  70                  75                  80

Trp Asp Leu Tyr Tyr His Val Phe Arg Arg Ile Ser Lys
                85                  90


<210> SEQ ID NO 40
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Ile Leu Trp His Glu Met Trp His Glu Gly Leu Ile Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Thr Gln Ala
65                  70                  75                  80

Trp Asp Leu Tyr Tyr His Val Phe Arg Arg Ile Ser Lys Thr Ser
                85                  90                  95


<210> SEQ ID NO 41
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Ile Leu Trp His Glu Met Trp His Glu Gly Leu Leu Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Thr Gln Ala
65                  70                  75                  80

Trp Asp Leu Tyr Tyr His Val Phe Arg Arg Ile Ser Lys Thr Ser
                85                  90                  95


<210> SEQ ID NO 42
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

-continued

<400> SEQUENCE: 42

```
Ile Leu Trp His Glu Met Trp His Glu Gly Leu Glu Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Leu Gln Ala
65                  70                  75                  80

Trp Asp Leu Tyr Tyr His Val Phe Arg Arg Ile Ser Lys Thr Ser
                85                  90                  95
```

<210> SEQ ID NO 43
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (78)..(78)
<223> OTHER INFORMATION: Any amino acid

<400> SEQUENCE: 43

```
Ile Leu Trp His Glu Met Trp His Glu Gly Leu Xaa Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Xaa Gln Ala
65                  70                  75                  80

Trp Asp Leu Tyr Tyr His Val Phe Arg Arg Ile Ser Lys Thr Ser
                85                  90                  95
```

<210> SEQ ID NO 44
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 44

```
Ile Leu Trp His Glu Met Trp His Glu Gly Leu Ile Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45
```

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Leu Gln Ala
65                  70                  75                  80

Trp Asp Leu Tyr Tyr His Val Phe Arg Arg Ile Ser Lys Thr Ser
                85                  90                  95

<210> SEQ ID NO 45
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45

Ile Leu Trp His Glu Met Trp His Glu Gly Leu Leu Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Leu Gln Ala
65                  70                  75                  80

Trp Asp Leu Tyr Tyr His Val Phe Arg Arg Ile Ser Lys Thr Ser
                85                  90                  95

<210> SEQ ID NO 46
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: misc_feature
<222> LOCATION: (1)..(2000)
<223> OTHER INFORMATION: /note="This sequence may encompass 50-2000
      nucleotides"

<400> SEQUENCE: 46
aaaaaaaaaa aaaaaaaaaa aaaaaaaaaa aaaaaaaaaa aaaaaaaaaa aaaaaaaaaa     60
aaaaaaaaaa aaaaaaaaaa aaaaaaaaaa aaaaaaaaaa aaaaaaaaaa aaaaaaaaaa    120
aaaaaaaaaa aaaaaaaaaa aaaaaaaaaa aaaaaaaaaa aaaaaaaaaa aaaaaaaaaa    180
aaaaaaaaaa aaaaaaaaaa aaaaaaaaaa aaaaaaaaaa aaaaaaaaaa aaaaaaaaaa    240
aaaaaaaaaa aaaaaaaaaa aaaaaaaaaa aaaaaaaaaa aaaaaaaaaa aaaaaaaaaa    300
aaaaaaaaaa aaaaaaaaaa aaaaaaaaaa aaaaaaaaaa aaaaaaaaaa aaaaaaaaaa    360
aaaaaaaaaa aaaaaaaaaa aaaaaaaaaa aaaaaaaaaa aaaaaaaaaa aaaaaaaaaa    420
aaaaaaaaaa aaaaaaaaaa aaaaaaaaaa aaaaaaaaaa aaaaaaaaaa aaaaaaaaaa    480
aaaaaaaaaa aaaaaaaaaa aaaaaaaaaa aaaaaaaaaa aaaaaaaaaa aaaaaaaaaa    540
aaaaaaaaaa aaaaaaaaaa aaaaaaaaaa aaaaaaaaaa aaaaaaaaaa aaaaaaaaaa    600
aaaaaaaaaa aaaaaaaaaa aaaaaaaaaa aaaaaaaaaa aaaaaaaaaa aaaaaaaaaa    660

```
aaaaaaaaaa aaaaaaaaaa aaaaaaaaaa aaaaaaaaaa aaaaaaaaaa aaaaaaaaaa    720

aaaaaaaaaa aaaaaaaaaa aaaaaaaaaa aaaaaaaaaa aaaaaaaaaa aaaaaaaaaa    780

aaaaaaaaaa aaaaaaaaaa aaaaaaaaaa aaaaaaaaaa aaaaaaaaaa aaaaaaaaaa    840

aaaaaaaaaa aaaaaaaaaa aaaaaaaaaa aaaaaaaaaa aaaaaaaaaa aaaaaaaaaa    900

aaaaaaaaaa aaaaaaaaaa aaaaaaaaaa aaaaaaaaaa aaaaaaaaaa aaaaaaaaaa    960

aaaaaaaaaa aaaaaaaaaa aaaaaaaaaa aaaaaaaaaa aaaaaaaaaa aaaaaaaaaa   1020

aaaaaaaaaa aaaaaaaaaa aaaaaaaaaa aaaaaaaaaa aaaaaaaaaa aaaaaaaaaa   1080

aaaaaaaaaa aaaaaaaaaa aaaaaaaaaa aaaaaaaaaa aaaaaaaaaa aaaaaaaaaa   1140

aaaaaaaaaa aaaaaaaaaa aaaaaaaaaa aaaaaaaaaa aaaaaaaaaa aaaaaaaaaa   1200

aaaaaaaaaa aaaaaaaaaa aaaaaaaaaa aaaaaaaaaa aaaaaaaaaa aaaaaaaaaa   1260

aaaaaaaaaa aaaaaaaaaa aaaaaaaaaa aaaaaaaaaa aaaaaaaaaa aaaaaaaaaa   1320

aaaaaaaaaa aaaaaaaaaa aaaaaaaaaa aaaaaaaaaa aaaaaaaaaa aaaaaaaaaa   1380

aaaaaaaaaa aaaaaaaaaa aaaaaaaaaa aaaaaaaaaa aaaaaaaaaa aaaaaaaaaa   1440

aaaaaaaaaa aaaaaaaaaa aaaaaaaaaa aaaaaaaaaa aaaaaaaaaa aaaaaaaaaa   1500

aaaaaaaaaa aaaaaaaaaa aaaaaaaaaa aaaaaaaaaa aaaaaaaaaa aaaaaaaaaa   1560

aaaaaaaaaa aaaaaaaaaa aaaaaaaaaa aaaaaaaaaa aaaaaaaaaa aaaaaaaaaa   1620

aaaaaaaaaa aaaaaaaaaa aaaaaaaaaa aaaaaaaaaa aaaaaaaaaa aaaaaaaaaa   1680

aaaaaaaaaa aaaaaaaaaa aaaaaaaaaa aaaaaaaaaa aaaaaaaaaa aaaaaaaaaa   1740

aaaaaaaaaa aaaaaaaaaa aaaaaaaaaa aaaaaaaaaa aaaaaaaaaa aaaaaaaaaa   1800

aaaaaaaaaa aaaaaaaaaa aaaaaaaaaa aaaaaaaaaa aaaaaaaaaa aaaaaaaaaa   1860

aaaaaaaaaa aaaaaaaaaa aaaaaaaaaa aaaaaaaaaa aaaaaaaaaa aaaaaaaaaa   1920

aaaaaaaaaa aaaaaaaaaa aaaaaaaaaa aaaaaaaaaa aaaaaaaaaa aaaaaaaaaa   1980

aaaaaaaaaa aaaaaaaaaa                                               2000
```

<210> SEQ ID NO 47
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 47

```
Glu Leu Ala Gly Ile Gly Ile Leu Thr Val
1               5                   10
```

<210> SEQ ID NO 48
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 48

```
Gly Ile Leu Gly Phe Val Phe Thr Leu
1               5
```

<210> SEQ ID NO 49
<211> LENGTH: 15

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Pro Val Ser Lys Met Arg Met Ala Thr Pro Leu Leu Met Gln Ala
1               5                   10                  15


<210> SEQ ID NO 50
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Pro Val Ser Lys Met Arg Met Ala Thr Pro Leu Leu Met Gln Ala
1               5                   10                  15


<210> SEQ ID NO 51
<211> LENGTH: 488
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

Met Ala Leu Pro Val Thr Ala Leu Leu Leu Pro Leu Ala Leu Leu Leu
1               5                   10                  15

His Ala Ala Arg Pro Gly Ser Gln Val Gln Leu Gln Gln Ser Gly Pro
            20                  25                  30

Glu Leu Glu Lys Pro Gly Ala Ser Val Lys Ile Ser Cys Lys Ala Ser
        35                  40                  45

Gly Tyr Ser Phe Thr Gly Tyr Thr Met Asn Trp Val Lys Gln Ser His
    50                  55                  60

Gly Lys Ser Leu Glu Trp Ile Gly Leu Ile Thr Pro Tyr Asn Gly Ala
65                  70                  75                  80

Ser Ser Tyr Asn Gln Lys Phe Arg Gly Lys Ala Thr Leu Thr Val Asp
                85                  90                  95

Lys Ser Ser Ser Thr Ala Tyr Met Asp Leu Leu Ser Leu Thr Ser Glu
            100                 105                 110

Asp Ser Ala Val Tyr Phe Cys Ala Arg Gly Gly Tyr Asp Gly Arg Gly
        115                 120                 125

Phe Asp Tyr Trp Gly Gln Gly Thr Thr Val Thr Val Ser Ser Gly Gly
    130                 135                 140

Gly Gly Ser Gly Gly Gly Gly Ser Ser Gly Gly Gly Ser Asp Ile Glu
145                 150                 155                 160

Leu Thr Gln Ser Pro Ala Ile Met Ser Ala Ser Pro Gly Glu Lys Val
                165                 170                 175

Thr Met Thr Cys Ser Ala Ser Ser Ser Val Ser Tyr Met His Trp Tyr
            180                 185                 190

Gln Gln Lys Ser Gly Thr Ser Pro Lys Arg Trp Ile Tyr Asp Thr Ser
        195                 200                 205

Lys Leu Ala Ser Gly Val Pro Gly Arg Phe Ser Gly Ser Gly Ser Gly
```

```
    210                 215                 220

Asn Ser Tyr Ser Leu Thr Ile Ser Ser Val Glu Ala Glu Asp Asp Ala
225                 230                 235                 240

Thr Tyr Tyr Cys Gln Gln Trp Ser Lys His Pro Leu Thr Tyr Gly Ala
                245                 250                 255

Gly Thr Lys Leu Glu Ile Lys Ala Ser Thr Thr Thr Pro Ala Pro Arg
            260                 265                 270

Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
    290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Lys Arg
                325                 330                 335

Gly Arg Lys Lys Leu Leu Tyr Ile Phe Lys Gln Pro Phe Met Arg Pro
            340                 345                 350

Val Gln Thr Thr Gln Glu Glu Asp Gly Cys Ser Cys Arg Phe Pro Glu
        355                 360                 365

Glu Glu Glu Gly Gly Cys Glu Leu Arg Val Lys Phe Ser Arg Ser Ala
    370                 375                 380

Asp Ala Pro Ala Tyr Lys Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
                405                 410                 415

Arg Asp Pro Glu Met Gly Gly Lys Pro Arg Arg Lys Asn Pro Gln Glu
            420                 425                 430

Gly Leu Tyr Asn Glu Leu Gln Lys Asp Lys Met Ala Glu Ala Tyr Ser
        435                 440                 445

Glu Ile Gly Met Lys Gly Glu Arg Arg Arg Gly Lys Gly His Asp Gly
    450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg
                485
```

<210> SEQ ID NO 52
<211> LENGTH: 5000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: misc_feature
<222> LOCATION: (1)..(5000)
<223> OTHER INFORMATION: /note="This sequence may encompass 50-5000 nucleotides"

<400> SEQUENCE: 52

```
tttttttttt tttttttttt tttttttttt tttttttttt tttttttttt tttttttttt      60

tttttttttt tttttttttt tttttttttt tttttttttt tttttttttt tttttttttt     120

tttttttttt tttttttttt tttttttttt tttttttttt tttttttttt tttttttttt     180

tttttttttt tttttttttt tttttttttt tttttttttt tttttttttt tttttttttt     240

tttttttttt tttttttttt tttttttttt tttttttttt tttttttttt tttttttttt     300
```

-continued tttttttttt tttttttttt tttttttttt tttttttttt tttttttttt tttttttttt 360
tttttttttt tttttttttt tttttttttt tttttttttt tttttttttt tttttttttt 420
tttttttttt tttttttttt tttttttttt tttttttttt tttttttttt tttttttttt 480
tttttttttt tttttttttt tttttttttt tttttttttt tttttttttt tttttttttt 540
tttttttttt tttttttttt tttttttttt tttttttttt tttttttttt tttttttttt 600
tttttttttt tttttttttt tttttttttt tttttttttt tttttttttt tttttttttt 660
tttttttttt tttttttttt tttttttttt tttttttttt tttttttttt tttttttttt 720
tttttttttt tttttttttt tttttttttt tttttttttt tttttttttt tttttttttt 780
tttttttttt tttttttttt tttttttttt tttttttttt tttttttttt tttttttttt 840
tttttttttt tttttttttt tttttttttt tttttttttt tttttttttt tttttttttt 900
tttttttttt tttttttttt tttttttttt tttttttttt tttttttttt tttttttttt 960
tttttttttt tttttttttt tttttttttt tttttttttt tttttttttt tttttttttt 1020
tttttttttt tttttttttt tttttttttt tttttttttt tttttttttt tttttttttt 1080
tttttttttt tttttttttt tttttttttt tttttttttt tttttttttt tttttttttt 1140
tttttttttt tttttttttt tttttttttt tttttttttt tttttttttt tttttttttt 1200
tttttttttt tttttttttt tttttttttt tttttttttt tttttttttt tttttttttt 1260
tttttttttt tttttttttt tttttttttt tttttttttt tttttttttt tttttttttt 1320
tttttttttt tttttttttt tttttttttt tttttttttt tttttttttt tttttttttt 1380
tttttttttt tttttttttt tttttttttt tttttttttt tttttttttt tttttttttt 1440
tttttttttt tttttttttt tttttttttt tttttttttt tttttttttt tttttttttt 1500
tttttttttt tttttttttt tttttttttt tttttttttt tttttttttt tttttttttt 1560
tttttttttt tttttttttt tttttttttt tttttttttt tttttttttt tttttttttt 1620
tttttttttt tttttttttt tttttttttt tttttttttt tttttttttt tttttttttt 1680
tttttttttt tttttttttt tttttttttt tttttttttt tttttttttt tttttttttt 1740
tttttttttt tttttttttt tttttttttt tttttttttt tttttttttt tttttttttt 1800
tttttttttt tttttttttt tttttttttt tttttttttt tttttttttt tttttttttt 1860
tttttttttt tttttttttt tttttttttt tttttttttt tttttttttt tttttttttt 1920
tttttttttt tttttttttt tttttttttt tttttttttt tttttttttt tttttttttt 1980
tttttttttt tttttttttt tttttttttt tttttttttt tttttttttt tttttttttt 2040
tttttttttt tttttttttt tttttttttt tttttttttt tttttttttt tttttttttt 2100
tttttttttt tttttttttt tttttttttt tttttttttt tttttttttt tttttttttt 2160
tttttttttt tttttttttt tttttttttt tttttttttt tttttttttt tttttttttt 2220
tttttttttt tttttttttt tttttttttt tttttttttt tttttttttt tttttttttt 2280
tttttttttt tttttttttt tttttttttt tttttttttt tttttttttt tttttttttt 2340
tttttttttt tttttttttt tttttttttt tttttttttt tttttttttt tttttttttt 2400
tttttttttt tttttttttt tttttttttt tttttttttt tttttttttt tttttttttt 2460
tttttttttt tttttttttt tttttttttt tttttttttt tttttttttt tttttttttt 2520
tttttttttt tttttttttt tttttttttt tttttttttt tttttttttt tttttttttt 2580
tttttttttt tttttttttt tttttttttt tttttttttt tttttttttt tttttttttt 2640

-continued

```
tttttttttt tttttttttt tttttttttt tttttttttt tttttttttt tttttttttt   2700
tttttttttt tttttttttt tttttttttt tttttttttt tttttttttt tttttttttt   2760
tttttttttt tttttttttt tttttttttt tttttttttt tttttttttt tttttttttt   2820
tttttttttt tttttttttt tttttttttt tttttttttt tttttttttt tttttttttt   2880
tttttttttt tttttttttt tttttttttt tttttttttt tttttttttt tttttttttt   2940
tttttttttt tttttttttt tttttttttt tttttttttt tttttttttt tttttttttt   3000
tttttttttt tttttttttt tttttttttt tttttttttt tttttttttt tttttttttt   3060
tttttttttt tttttttttt tttttttttt tttttttttt tttttttttt tttttttttt   3120
tttttttttt tttttttttt tttttttttt tttttttttt tttttttttt tttttttttt   3180
tttttttttt tttttttttt tttttttttt tttttttttt tttttttttt tttttttttt   3240
tttttttttt tttttttttt tttttttttt tttttttttt tttttttttt tttttttttt   3300
tttttttttt tttttttttt tttttttttt tttttttttt tttttttttt tttttttttt   3360
tttttttttt tttttttttt tttttttttt tttttttttt tttttttttt tttttttttt   3420
tttttttttt tttttttttt tttttttttt tttttttttt tttttttttt tttttttttt   3480
tttttttttt tttttttttt tttttttttt tttttttttt tttttttttt tttttttttt   3540
tttttttttt tttttttttt tttttttttt tttttttttt tttttttttt tttttttttt   3600
tttttttttt tttttttttt tttttttttt tttttttttt tttttttttt tttttttttt   3660
tttttttttt tttttttttt tttttttttt tttttttttt tttttttttt tttttttttt   3720
tttttttttt tttttttttt tttttttttt tttttttttt tttttttttt tttttttttt   3780
tttttttttt tttttttttt tttttttttt tttttttttt tttttttttt tttttttttt   3840
tttttttttt tttttttttt tttttttttt tttttttttt tttttttttt tttttttttt   3900
tttttttttt tttttttttt tttttttttt tttttttttt tttttttttt tttttttttt   3960
tttttttttt tttttttttt tttttttttt tttttttttt tttttttttt tttttttttt   4020
tttttttttt tttttttttt tttttttttt tttttttttt tttttttttt tttttttttt   4080
tttttttttt tttttttttt tttttttttt tttttttttt tttttttttt tttttttttt   4140
tttttttttt tttttttttt tttttttttt tttttttttt tttttttttt tttttttttt   4200
tttttttttt tttttttttt tttttttttt tttttttttt tttttttttt tttttttttt   4260
tttttttttt tttttttttt tttttttttt tttttttttt tttttttttt tttttttttt   4320
tttttttttt tttttttttt tttttttttt tttttttttt tttttttttt tttttttttt   4380
tttttttttt tttttttttt tttttttttt tttttttttt tttttttttt tttttttttt   4440
tttttttttt tttttttttt tttttttttt tttttttttt tttttttttt tttttttttt   4500
tttttttttt tttttttttt tttttttttt tttttttttt tttttttttt tttttttttt   4560
tttttttttt tttttttttt tttttttttt tttttttttt tttttttttt tttttttttt   4620
tttttttttt tttttttttt tttttttttt tttttttttt tttttttttt tttttttttt   4680
tttttttttt tttttttttt tttttttttt tttttttttt tttttttttt tttttttttt   4740
tttttttttt tttttttttt tttttttttt tttttttttt tttttttttt tttttttttt   4800
tttttttttt tttttttttt tttttttttt tttttttttt tttttttttt tttttttttt   4860
tttttttttt tttttttttt tttttttttt tttttttttt tttttttttt tttttttttt   4920
tttttttttt tttttttttt tttttttttt tttttttttt tttttttttt tttttttttt   4980
tttttttttt tttttttttt                                               5000
```

<210> SEQ ID NO 53
<211> LENGTH: 5000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: misc_feature
<222> LOCATION: (1)..(5000)
<223> OTHER INFORMATION: /note="This sequence may encompass 100-5000 nucleotides"

<400> SEQUENCE: 53
aaaaaaaaaa aaaaaaaaaa aaaaaaaaaa aaaaaaaaaa aaaaaaaaaa aaaaaaaaaa 60
aaaaaaaaaa aaaaaaaaaa aaaaaaaaaa aaaaaaaaaa aaaaaaaaaa aaaaaaaaaa 120
aaaaaaaaaa aaaaaaaaaa aaaaaaaaaa aaaaaaaaaa aaaaaaaaaa aaaaaaaaaa 180
aaaaaaaaaa aaaaaaaaaa aaaaaaaaaa aaaaaaaaaa aaaaaaaaaa aaaaaaaaaa 240
aaaaaaaaaa aaaaaaaaaa aaaaaaaaaa aaaaaaaaaa aaaaaaaaaa aaaaaaaaaa 300
aaaaaaaaaa aaaaaaaaaa aaaaaaaaaa aaaaaaaaaa aaaaaaaaaa aaaaaaaaaa 360
aaaaaaaaaa aaaaaaaaaa aaaaaaaaaa aaaaaaaaaa aaaaaaaaaa aaaaaaaaaa 420
aaaaaaaaaa aaaaaaaaaa aaaaaaaaaa aaaaaaaaaa aaaaaaaaaa aaaaaaaaaa 480
aaaaaaaaaa aaaaaaaaaa aaaaaaaaaa aaaaaaaaaa aaaaaaaaaa aaaaaaaaaa 540
aaaaaaaaaa aaaaaaaaaa aaaaaaaaaa aaaaaaaaaa aaaaaaaaaa aaaaaaaaaa 600
aaaaaaaaaa aaaaaaaaaa aaaaaaaaaa aaaaaaaaaa aaaaaaaaaa aaaaaaaaaa 660
aaaaaaaaaa aaaaaaaaaa aaaaaaaaaa aaaaaaaaaa aaaaaaaaaa aaaaaaaaaa 720
aaaaaaaaaa aaaaaaaaaa aaaaaaaaaa aaaaaaaaaa aaaaaaaaaa aaaaaaaaaa 780
aaaaaaaaaa aaaaaaaaaa aaaaaaaaaa aaaaaaaaaa aaaaaaaaaa aaaaaaaaaa 840
aaaaaaaaaa aaaaaaaaaa aaaaaaaaaa aaaaaaaaaa aaaaaaaaaa aaaaaaaaaa 900
aaaaaaaaaa aaaaaaaaaa aaaaaaaaaa aaaaaaaaaa aaaaaaaaaa aaaaaaaaaa 960
aaaaaaaaaa aaaaaaaaaa aaaaaaaaaa aaaaaaaaaa aaaaaaaaaa aaaaaaaaaa 1020
aaaaaaaaaa aaaaaaaaaa aaaaaaaaaa aaaaaaaaaa aaaaaaaaaa aaaaaaaaaa 1080
aaaaaaaaaa aaaaaaaaaa aaaaaaaaaa aaaaaaaaaa aaaaaaaaaa aaaaaaaaaa 1140
aaaaaaaaaa aaaaaaaaaa aaaaaaaaaa aaaaaaaaaa aaaaaaaaaa aaaaaaaaaa 1200
aaaaaaaaaa aaaaaaaaaa aaaaaaaaaa aaaaaaaaaa aaaaaaaaaa aaaaaaaaaa 1260
aaaaaaaaaa aaaaaaaaaa aaaaaaaaaa aaaaaaaaaa aaaaaaaaaa aaaaaaaaaa 1320
aaaaaaaaaa aaaaaaaaaa aaaaaaaaaa aaaaaaaaaa aaaaaaaaaa aaaaaaaaaa 1380
aaaaaaaaaa aaaaaaaaaa aaaaaaaaaa aaaaaaaaaa aaaaaaaaaa aaaaaaaaaa 1440
aaaaaaaaaa aaaaaaaaaa aaaaaaaaaa aaaaaaaaaa aaaaaaaaaa aaaaaaaaaa 1500
aaaaaaaaaa aaaaaaaaaa aaaaaaaaaa aaaaaaaaaa aaaaaaaaaa aaaaaaaaaa 1560
aaaaaaaaaa aaaaaaaaaa aaaaaaaaaa aaaaaaaaaa aaaaaaaaaa aaaaaaaaaa 1620
aaaaaaaaaa aaaaaaaaaa aaaaaaaaaa aaaaaaaaaa aaaaaaaaaa aaaaaaaaaa 1680
aaaaaaaaaa aaaaaaaaaa aaaaaaaaaa aaaaaaaaaa aaaaaaaaaa aaaaaaaaaa 1740
aaaaaaaaaa aaaaaaaaaa aaaaaaaaaa aaaaaaaaaa aaaaaaaaaa aaaaaaaaaa 1800
aaaaaaaaaa aaaaaaaaaa aaaaaaaaaa aaaaaaaaaa aaaaaaaaaa aaaaaaaaaa 1860

-continued

```
aaaaaaaaaa aaaaaaaaaa aaaaaaaaaa aaaaaaaaaa aaaaaaaaaa aaaaaaaaaa   1920
aaaaaaaaaa aaaaaaaaaa aaaaaaaaaa aaaaaaaaaa aaaaaaaaaa aaaaaaaaaa   1980
aaaaaaaaaa aaaaaaaaaa aaaaaaaaaa aaaaaaaaaa aaaaaaaaaa aaaaaaaaaa   2040
aaaaaaaaaa aaaaaaaaaa aaaaaaaaaa aaaaaaaaaa aaaaaaaaaa aaaaaaaaaa   2100
aaaaaaaaaa aaaaaaaaaa aaaaaaaaaa aaaaaaaaaa aaaaaaaaaa aaaaaaaaaa   2160
aaaaaaaaaa aaaaaaaaaa aaaaaaaaaa aaaaaaaaaa aaaaaaaaaa aaaaaaaaaa   2220
aaaaaaaaaa aaaaaaaaaa aaaaaaaaaa aaaaaaaaaa aaaaaaaaaa aaaaaaaaaa   2280
aaaaaaaaaa aaaaaaaaaa aaaaaaaaaa aaaaaaaaaa aaaaaaaaaa aaaaaaaaaa   2340
aaaaaaaaaa aaaaaaaaaa aaaaaaaaaa aaaaaaaaaa aaaaaaaaaa aaaaaaaaaa   2400
aaaaaaaaaa aaaaaaaaaa aaaaaaaaaa aaaaaaaaaa aaaaaaaaaa aaaaaaaaaa   2460
aaaaaaaaaa aaaaaaaaaa aaaaaaaaaa aaaaaaaaaa aaaaaaaaaa aaaaaaaaaa   2520
aaaaaaaaaa aaaaaaaaaa aaaaaaaaaa aaaaaaaaaa aaaaaaaaaa aaaaaaaaaa   2580
aaaaaaaaaa aaaaaaaaaa aaaaaaaaaa aaaaaaaaaa aaaaaaaaaa aaaaaaaaaa   2640
aaaaaaaaaa aaaaaaaaaa aaaaaaaaaa aaaaaaaaaa aaaaaaaaaa aaaaaaaaaa   2700
aaaaaaaaaa aaaaaaaaaa aaaaaaaaaa aaaaaaaaaa aaaaaaaaaa aaaaaaaaaa   2760
aaaaaaaaaa aaaaaaaaaa aaaaaaaaaa aaaaaaaaaa aaaaaaaaaa aaaaaaaaaa   2820
aaaaaaaaaa aaaaaaaaaa aaaaaaaaaa aaaaaaaaaa aaaaaaaaaa aaaaaaaaaa   2880
aaaaaaaaaa aaaaaaaaaa aaaaaaaaaa aaaaaaaaaa aaaaaaaaaa aaaaaaaaaa   2940
aaaaaaaaaa aaaaaaaaaa aaaaaaaaaa aaaaaaaaaa aaaaaaaaaa aaaaaaaaaa   3000
aaaaaaaaaa aaaaaaaaaa aaaaaaaaaa aaaaaaaaaa aaaaaaaaaa aaaaaaaaaa   3060
aaaaaaaaaa aaaaaaaaaa aaaaaaaaaa aaaaaaaaaa aaaaaaaaaa aaaaaaaaaa   3120
aaaaaaaaaa aaaaaaaaaa aaaaaaaaaa aaaaaaaaaa aaaaaaaaaa aaaaaaaaaa   3180
aaaaaaaaaa aaaaaaaaaa aaaaaaaaaa aaaaaaaaaa aaaaaaaaaa aaaaaaaaaa   3240
aaaaaaaaaa aaaaaaaaaa aaaaaaaaaa aaaaaaaaaa aaaaaaaaaa aaaaaaaaaa   3300
aaaaaaaaaa aaaaaaaaaa aaaaaaaaaa aaaaaaaaaa aaaaaaaaaa aaaaaaaaaa   3360
aaaaaaaaaa aaaaaaaaaa aaaaaaaaaa aaaaaaaaaa aaaaaaaaaa aaaaaaaaaa   3420
aaaaaaaaaa aaaaaaaaaa aaaaaaaaaa aaaaaaaaaa aaaaaaaaaa aaaaaaaaaa   3480
aaaaaaaaaa aaaaaaaaaa aaaaaaaaaa aaaaaaaaaa aaaaaaaaaa aaaaaaaaaa   3540
aaaaaaaaaa aaaaaaaaaa aaaaaaaaaa aaaaaaaaaa aaaaaaaaaa aaaaaaaaaa   3600
aaaaaaaaaa aaaaaaaaaa aaaaaaaaaa aaaaaaaaaa aaaaaaaaaa aaaaaaaaaa   3660
aaaaaaaaaa aaaaaaaaaa aaaaaaaaaa aaaaaaaaaa aaaaaaaaaa aaaaaaaaaa   3720
aaaaaaaaaa aaaaaaaaaa aaaaaaaaaa aaaaaaaaaa aaaaaaaaaa aaaaaaaaaa   3780
aaaaaaaaaa aaaaaaaaaa aaaaaaaaaa aaaaaaaaaa aaaaaaaaaa aaaaaaaaaa   3840
aaaaaaaaaa aaaaaaaaaa aaaaaaaaaa aaaaaaaaaa aaaaaaaaaa aaaaaaaaaa   3900
aaaaaaaaaa aaaaaaaaaa aaaaaaaaaa aaaaaaaaaa aaaaaaaaaa aaaaaaaaaa   3960
aaaaaaaaaa aaaaaaaaaa aaaaaaaaaa aaaaaaaaaa aaaaaaaaaa aaaaaaaaaa   4020
aaaaaaaaaa aaaaaaaaaa aaaaaaaaaa aaaaaaaaaa aaaaaaaaaa aaaaaaaaaa   4080
aaaaaaaaaa aaaaaaaaaa aaaaaaaaaa aaaaaaaaaa aaaaaaaaaa aaaaaaaaaa   4140
aaaaaaaaaa aaaaaaaaaa aaaaaaaaaa aaaaaaaaaa aaaaaaaaaa aaaaaaaaaa   4200
```

-continued

```
aaaaaaaaaa aaaaaaaaaa aaaaaaaaaa aaaaaaaaaa aaaaaaaaaa aaaaaaaaaa   4260

aaaaaaaaaa aaaaaaaaaa aaaaaaaaaa aaaaaaaaaa aaaaaaaaaa aaaaaaaaaa   4320

aaaaaaaaaa aaaaaaaaaa aaaaaaaaaa aaaaaaaaaa aaaaaaaaaa aaaaaaaaaa   4380

aaaaaaaaaa aaaaaaaaaa aaaaaaaaaa aaaaaaaaaa aaaaaaaaaa aaaaaaaaaa   4440

aaaaaaaaaa aaaaaaaaaa aaaaaaaaaa aaaaaaaaaa aaaaaaaaaa aaaaaaaaaa   4500

aaaaaaaaaa aaaaaaaaaa aaaaaaaaaa aaaaaaaaaa aaaaaaaaaa aaaaaaaaaa   4560

aaaaaaaaaa aaaaaaaaaa aaaaaaaaaa aaaaaaaaaa aaaaaaaaaa aaaaaaaaaa   4620

aaaaaaaaaa aaaaaaaaaa aaaaaaaaaa aaaaaaaaaa aaaaaaaaaa aaaaaaaaaa   4680

aaaaaaaaaa aaaaaaaaaa aaaaaaaaaa aaaaaaaaaa aaaaaaaaaa aaaaaaaaaa   4740

aaaaaaaaaa aaaaaaaaaa aaaaaaaaaa aaaaaaaaaa aaaaaaaaaa aaaaaaaaaa   4800

aaaaaaaaaa aaaaaaaaaa aaaaaaaaaa aaaaaaaaaa aaaaaaaaaa aaaaaaaaaa   4860

aaaaaaaaaa aaaaaaaaaa aaaaaaaaaa aaaaaaaaaa aaaaaaaaaa aaaaaaaaaa   4920

aaaaaaaaaa aaaaaaaaaa aaaaaaaaaa aaaaaaaaaa aaaaaaaaaa aaaaaaaaaa   4980

aaaaaaaaaa aaaaaaaaaa                                               5000


<210> SEQ ID NO 54
<211> LENGTH: 400
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: misc_feature
<222> LOCATION: (1)..(400)
<223> OTHER INFORMATION: /note="This sequence may encompass 100-400
      nucleotides"

<400> SEQUENCE: 54

aaaaaaaaaa aaaaaaaaaa aaaaaaaaaa aaaaaaaaaa aaaaaaaaaa aaaaaaaaaa     60

aaaaaaaaaa aaaaaaaaaa aaaaaaaaaa aaaaaaaaaa aaaaaaaaaa aaaaaaaaaa    120

aaaaaaaaaa aaaaaaaaaa aaaaaaaaaa aaaaaaaaaa aaaaaaaaaa aaaaaaaaaa    180

aaaaaaaaaa aaaaaaaaaa aaaaaaaaaa aaaaaaaaaa aaaaaaaaaa aaaaaaaaaa    240

aaaaaaaaaa aaaaaaaaaa aaaaaaaaaa aaaaaaaaaa aaaaaaaaaa aaaaaaaaaa    300

aaaaaaaaaa aaaaaaaaaa aaaaaaaaaa aaaaaaaaaa aaaaaaaaaa aaaaaaaaaa    360

aaaaaaaaaa aaaaaaaaaa aaaaaaaaaa aaaaaaaaaa                          400
```

ENHANCED ANTIGEN PRESENTING ABILITY OF RNA CAR T CELLS BY CO-INTRODUCTION OF COSTIMULATORY MOLECULES

This application is a divisional of U.S. application Ser. No. 15/113,044, filed Jul. 20, 2016, now issued U.S. Pat. No. 11,028,143, which is a national stage application under 35 U.S.C. § 371 of International Application No. PCT/US2015/012284, filed Jan. 21, 2015, published as International Publication No. WO2015/112626 on Jul. 30, 2015, which application claims priority to U.S. Ser. No. 61/929,813, filed Jan. 21, 2014, the entire contents of each of which are incorporated herein by reference.

SEQUENCE LISTING

The instant application contains a Sequence Listing which has been submitted electronically in ASCII format and is hereby incorporated by reference in its entirety. Said ASCII copy, created on May 17, 2015, is named N2067-7036WO-_SL.TXT and is 76,949 bytes in size.

BACKGROUND

Chimeric antigen receptors (CARs) are molecules that combine antibody-based specificity for disease-associated surface antigens with T cell receptor-activating intracellular domains with disease-directed cellular immune activity. This configuration allows T cells engineered to express a CAR to achieve MHC-independent primary activation through single chain Fv (scFv) antigen-specific extracellular regions fused to intracellular domains that provide T cell activation and co-stimulatory signals. Second and third generation CARs also provide appropriate co-stimulatory signals via CD28 and/or CD 137 (4-IBB) intracellular activation motifs, which augment cytokine secretion and anti-tumor activity in a variety of solid tumor and leukemia models (Pinthus, et al, 2004, J Clin Invest 114(12): 1774-1781; Milone, et al. 2009, Mol Ther 17(8): 1453-1464; Sadelain, et al, 2009, Curr Opin Immunol 21(2):215-223). The benefit of bypassing the need for antigen presentation by MHC molecules to achieve cytotoxicity makes CAR-engineered T cells an attractive therapeutic modality.

Adoptive transfer of cytotoxic T lymphocytes (CTLs) has shown great promise in both viral and cancer indications. After many years of less than optimum results with CAR-based T-cell therapy, improved culture systems and cell engineering technologies have made possible CAR T cells with more potent antitumor effects (Sadelain et al, 2009. Curr Opin Immunol 21:215-23). The technology has also been successfully applied in the clinical context, with improved clinical results being reported for CARs introduced with retroviral vectors (Till et al. 2008, Blood 112: 2261-71; Pule et al, 2008, Nat Med 14: 1264-70). These CAR T cells also exhibit enhanced toxicity (Brentjens et alt 2010, Mol Ther 18:666-8; Morgan et al, 2010, Mol Ther 18:843-51).

As an emerging technology, there is an urgent need in the art for improving on existing CAR-based therapies that would allow for more effective, safe, and efficient adoptive transfer of CTLs.

SUMMARY

The present invention provides T cells engineered to exhibit increased anti-tumor activity by co-expressing a chimeric antigen receptor (CAR) and one or more enhancers of T cell priming (hereafter "ETPs"). The addition of an ETP component to the CAR T cell confers enhanced "professional" antigen-presenting cell (APC) function, which confers permanent anti-tumor immunity. In an embodiment, the CAR and one or more ETPs are transiently co-expressed in a T cell. Thus, the engineered T cells are safe (given the transient nature of the CAR/ETP expression), and induce prolonged (even permanent) immunity via APC function. As such, the T cells can be used to treat a wide variety of diseases associated with cell surface (target) antigens.

Accordingly, in one aspect, the invention provides a T cell comprising nucleic acid, e.g., exogenous nucleic acid, wherein (a) the nucleic acid comprises a first nucleic acid sequence encoding a chimeric antigen receptor (CAR) comprising an extracellular domain, a transmembrane domain, and an intracellular signaling domain, and (b) the nucleic acid comprises a second nucleic acid sequence encoding a polypeptide which enhances T cell priming, or a functional fragment or variant thereof, provided that (i) the first and/or second nucleic acid sequence comprises an RNA; or (ii) the CAR further comprises a second intracellular signaling domain, e.g., a costimulatory signaling domain. In an embodiment, the first and second nucleic acid sequences are disposed on a single nucleic acid molecule. In an embodiment, the nucleic acid molecule comprises RNA. In an embodiment, the nucleic acid molecule comprises DNA.

In an embodiment, the first and second nucleic acid sequences are disposed on two or more distinct nucleic acid molecules. In an embodiment, one or both nucleic acid molecules comprise RNA molecules. In an embodiment, one or both nucleic acid molecules comprise DNA molecules.

In an embodiment, one nucleic acid molecule comprises an RNA molecule and the other nucleic acid comprises a DNA molecule.

In an embodiment, the second intracellular signaling domain comprises a costimulatory signaling domain.

In an embodiment, the CAR comprises one or more costimulatory signaling domains.

In an embodiment, the intracellular signaling domain comprises a CD3zeta domain and the second intracellular signaling domain comprises a 4-1BB domain.

In an embodiment, the first nucleic acid sequence comprises an RNA. In an embodiment, the second nucleic acid sequence comprises an RNA. In an embodiment, the first and the second nucleic acid sequence each comprise RNA.

In an embodiment, the T cell is transfected to transiently express the first and/or second RNAs.

In an embodiment, the T cell does not comprise an exogenous DNA encoding the first or second RNA.

In an embodiment, the first and/or second RNAs are generated by in vitro transcription.

In an embodiment, the first and/or second RNAs are synthetic RNAs.

In an embodiment, the first and/or second RNAs are introduced into the T cell by electroporation.

In an embodiment, the CAR further comprises one or more costimulatory signaling domains, and wherein the first and/or second nucleic acid sequence comprises DNA or cDNA.

In an embodiment, the first and/or second nucleic acid sequence comprises a vector. In an embodiment, the vector is a viral vector. In an embodiment, the viral vector is a retroviral vector or a lentiviral vector. In an embodiment, the T cell is virally transduced to express the first and/or second nucleic acid sequence.

In an embodiment, the extracellular domain of the CAR comprises an antigen-binding domain. In an embodiment, the antigen-binding domain is a scFv domain.

In an embodiment, the transmembrane domain comprises the transmembrane portion of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154.

In an embodiment, the intracellular signaling domain comprises a functional signaling domain of CD3 zeta, common FcR gamma (FCER1G), Fc gamma RIIa, FcR beta (Fc Epsilon R1b), CD3 gamma, CD3 delta, CD3 epsilon, CD79a, CD79b, DAP10, and DAP12.

In an embodiment, the extracellular domain is connected to the transmembrane domain by a hinge region.

In an embodiment, the CAR further comprises one or more costimulatory signaling domains. In an embodiment, the costimulatory signaling domain is a functional signaling domain from a protein selected from the group consisting of OX40, CD27, CD28, CD30, CD40, PD-1, CD2, CD7, CD258, NKG2C, B7-H3, a ligand that binds to CD83, ICAM-1, LFA-1 (CD11a/CD18), ICOS and 4-1BB (CD137), or any combination thereof.

In an embodiment, the polypeptide which enhances T cell priming (ETP) is selected from the group consisting of a costimulatory molecule, a soluble cytokine, a polypeptide involved in antigen presentation, a polypeptide involved in trafficking and/or migration, or a polypeptide involved in dendritic cell targeting, or a functional fragment or variant thereof. In an embodiment, the costimulatory molecule ETP is selected from the group consisting of CD70, CD83, CD80, CD86, CD40, CD154, CD137L (4-1BBL), CD252 (OX40L), CD275 (ICOS-L), CD54 (ICAM-1), CD49a, CD43, CD48, CD 112 (PVRL2), CD150 (SLAM), CD155 (PVR), CD265 (RANK), CD270 (HVEM), TL1A, CD127, IL-4R, GITR-L, CD160, CD258, TIM-4, CD153 (CD30L), CD200R (OX2R), CD44, ligands thereof, and functional fragments and variants thereof. In an embodiment, the soluble cytokine is selected from the group consisting of: IL-2, IL-12, IL-6, IL-7, IL-15, IL-18, IL-21, GM-CSF, IL-18, IL-21, IL-27, and functional fragments and variants thereof. In an embodiment, the polypeptide involved in antigen presentation is selected from the group consisting of CD64, MHC I, MHC II, and functional fragments and variants thereof. In an embodiment, the polypeptide involved in trafficking and/or migration is selected from the group consisting of CD183, CCR2, CCR6, CD50, CD197, CD58, CD62L, and functional fragments and variants thereof. In an embodiment, the polypeptide involved in DC targeting is selected from the group consisting of TLR ligands, anti-DEC-205 antibody, an anti-DC-SIGN antibody, and functional fragments and variants thereof.

In an embodiment, the antigen-binding domain binds to an antigen associated with a disease state. In an embodiment, the disease state is selected from the group consisting of a proliferative disease, a precancerous condition, a non-cancer indication, a viral infection, and a bacterial infection. In an embodiment, the antigen-binding domain binds to a tumor antigen, a viral antigen, or a bacterial antigen. In an embodiment, the tumor antigen is an antigen associated with a cancer selected from the group consisting of brain cancer, bladder cancer, breast cancer, cervical cancer, colorectal cancer, liver cancer, kidney cancer, lymphoma, leukemia, lung cancer, melanoma, metastatic melanoma, mesothelioma, neuroblastoma, ovarian cancer, prostate cancer, pancreatic cancer, renal cancer, skin cancer, thymoma, sarcoma, non-Hodgkin's lymphoma, Hodgkin's lymphoma, uterine cancer, and combinations thereof.

In an embodiment, the T cell described herein has enhanced antigen presentation ability relative to a T cell which lacks the second nucleic acid sequence.

In an embodiment, the T cell described herein has enhanced T cell priming ability relative to a T cell which lacks the second nucleic acid sequence.

In an embodiment, the T cell is transfected to transiently express a nucleic acid comprising a third nucleic acid sequence encoding a polypeptide which enhances T cell priming, or a functional fragment or variant thereof, which differs from the polypeptide encoded by the second nucleic acid sequence. In an embodiment, the T cell has increased T cell priming ability relative to a T cell comprising the first nucleic acid sequence and second nucleic acid sequence, but not the third nucleic acid sequence. In an embodiment, the third nucleic acid sequence comprises an RNA. In an embodiment, the T cell is transfected to transiently express the third RNA. In an embodiment, the cell does not comprise an exogenous DNA encoding the third RNA. In an embodiment, the CAR comprises one or more costimulatory signaling domains, and wherein the third nucleic acid sequence comprises DNA. In an embodiment, the T cell further comprises one or more additional distinct nucleic acid sequences encoding a polypeptide which enhances T cell priming, or a functional fragment or variant thereof, which differ from the polypeptides encoded by the second and third nucleic acid sequences. In an embodiment, the one or more additional nucleic acid sequences comprises RNA. In an embodiment, the CAR comprises one or more costimulatory signaling domains, and wherein the one or more additional nucleic acids comprise DNA. In an embodiment, the first, second, and/or additional nucleic acid sequences are transcribed from one or more in vitro transcription vectors.

In an embodiment, expression of the polypeptide encoded by the second and/or additional nucleic acid sequences does not substantially affect, e.g., decrease, reduce, or inhibit, the cell-killing function of the CAR encoded by the first nucleic acid sequence.

In an embodiment, the T cell has increased efficacy in killing tumor cells or reducing tumor size in a subject with a tumor relative to a T cell comprising only the CAR encoded by the first nucleic acid sequence.

In an embodiment, the T cell enhances the priming of T cells with a tumor antigen, a viral antigen, a bacterial antigen.

In an embodiment, the T cells described herein are made by introducing a nucleic acid wherein (a) the nucleic acid comprises a first nucleic acid sequence encoding a chimeric antigen receptor (CAR) comprising an extracellular domain, a transmembrane domain, and an intracellular signaling domain, and (b) the nucleic acid comprises a second nucleic acid sequence encoding a polypeptide which enhances T cell priming, or a functional fragment or variant thereof; provided that (i) the first and/or second nucleic acid sequence comprises an RNA; or (ii) the CAR further comprises a second intracellular signaling domain.

In another aspect, the invention provides a method of generating a T cell having enhanced anti-cancer activity, e.g., anti-tumor activity, the method comprising introducing a nucleic acid, wherein:

(a) the nucleic acid comprises a first nucleic acid sequence encoding a chimeric antigen receptor (CAR) described herein comprising an extracellular domain, a transmembrane domain, and an intracellular signaling domain, and (b) the nucleic acid comprises a second nucleic acid sequence encoding a polypeptide which enhances T cell priming (ETP) described herein, or a functional fragment or variant thereof;

provided that (i) the first and/or second nucleic acid sequence comprises an RNA; or (ii) the CAR further comprises a second intracellular signaling domain.

In an embodiment, the first and second nucleic acid sequences are disposed on a single nucleic acid molecule. In an embodiment, the nucleic acid molecule comprises RNA. In an embodiment, the nucleic acid molecule comprises DNA.

In an embodiment, the first and second nucleic acid sequences are disposed on two or more distinct nucleic acid molecules. In an embodiment, one or both nucleic acid molecules comprise RNA molecules. In an embodiment, one or both nucleic acid molecules comprise DNA molecules.

In an embodiment, one nucleic acid molecule comprises an RNA molecule and the other nucleic acid comprises a DNA molecule.

In an embodiment, the second intracellular signaling domain comprises a costimulatory signaling domain. In an embodiment, the CAR comprises one or more costimulatory signaling domains. In an embodiment, the intracellular signaling domain comprises a CD3zeta domain and the second intracellular signaling domain comprises a 4-1BB domain.

In an embodiment, the first nucleic acid sequence comprises an RNA. In an embodiment, the second nucleic acid sequence comprises an RNA. In an embodiment, the first and the second nucleic acid sequence each comprise RNA.

In an embodiment, the T cell is transfected to transiently express the first and/or second RNAs.

In an embodiment, the T cell does not comprise an exogenous DNA encoding the first or second RNA.

In an embodiment, the first and/or second RNAs are generated by in vitro transcription.

In an embodiment, the first and/or second RNAs are synthetic RNAs.

In an embodiment, the first and/or second RNAs are introduced into the T cell by electroporation.

In an embodiment, the CAR further comprises one or more costimulatory signaling domains, and wherein the first and/or second nucleic acid sequence comprises DNA or cDNA.

In an embodiment, the first and/or second nucleic acid sequence comprises a vector. In an embodiment, the vector is a viral vector. In an embodiment, the viral vector is a retroviral vector or a lentiviral vector. In an embodiment, the T cell is virally transduced to express the first and/or second nucleic acid sequence.

In another aspect, the invention provides a method of vaccinating a subject comprising administering to the subject the T cell described herein. In an embodiment, the method further comprises administering to the subject an antigen. In an embodiment, the antigen is a tumor antigen, a viral antigen, or a bacterial antigen.

In another aspect, the invention provides a T cell, transfected to transiently express two or more distinct exogenous RNAs, wherein (a) the first RNA comprises a nucleic acid sequence encoding a CAR comprising an extracellular domain, a transmembrane domain, and an intracellular signaling domain, and (b) the second RNA comprises a nucleic acid sequence encoding a polypeptide which enhances T cell priming (i.e., an ETP). The ETP can, for example, be a functional fragment or variant of the wild-type ETP. In some embodiments, the T cells of the invention are transfected to transiently express a third distinct RNA comprising a nucleic acid sequence encoding an ETP, or a functional fragment or variant thereof, which differs from that encoded by the second RNA.

Exemplary extracellular domains of the CAR include, for example, an antigen-binding moiety, e.g., an scFv domain, which binds a disease-associated antigen (i.e., an antigen that is either unique, or expressed more highly in diseased cells compared to normal cells). Such antigens can be associated with a proliferative disease, a precancerous condition, and a non-cancer indication. In some embodiments, the antigen-binding moiety binds a tumor antigen, for example, an antigen associated with brain cancer (e.g., a glioma), bladder cancer, breast cancer, cervical cancer, colorectal cancer, liver cancer, kidney cancer, lymphoma, leukemia, lung cancer, melanoma, metastatic melanoma, mesothelioma, neuroblastoma, ovarian cancer, prostate cancer, pancreatic cancer, renal cancer, skin cancer, thymoma, sarcoma, non-Hodgkin's lymphoma, Hodgkin's lymphoma, uterine cancer, and combinations thereof.

In one embodiment, the transmembrane domain of the CAR is a transmembrane domain described herein. Exemplary transmembrane domains of the CAR include a transmembrane domain of, for example, the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, or CD154. The extracellular domain can be connected to the transmembrane domain by a hinge region.

In one embodiment, the intracellular domain of the CAR is an intracellular domain described herein. Exemplary intracellular domains of the CAR include, for example, the functional signaling domain of TCR zeta, FcR gamma, FcR beta, CD3 gamma, CD3 delta, CD3 epsilon, CD5, CD22, CD79a, CD79b, CD66d, 4-1BB, and/or CD3-zeta. In an embodiment, the intracellular signaling domain comprises a functional signaling domain of CD3 zeta, common FcR gamma (FCER1G), Fc gamma RIIa, FcR beta (Fc Epsilon R1b), CD3 gamma, CD3 delta, CD3 epsilon, CD79a, CD79b, DAP10, and DAP12.

The CAR may also comprise one or more costimulatory signaling domains, e.g., a costimulatory signaling domain described herein. For example, the costimulatory signaling domain can be a costimulatory signaling domain of OX40, CD27, CD28, CD30, CD40, PD-1, CD2, CD7, CD258, NKG2C, B7-H3, a ligand that binds to CD83, ICAM-1, LFA-1 (CD11a/CD18), ICOS and 4-1BB (CD137), or any combination thereof.

The ETP encoded by the second RNA can be, for example, a costimulatory molecule (e.g., CD70, CD83, CD80, CD86, CD40, CD154, CD137L (4-1BBL), CD252 (OX40L), CD275 (ICOS-L), CD54 (ICAM-1), CD49a, CD43, CD48, CD 112 (PVRL2), CD150 (SLAM), CD155 (PVR), CD265 (RANK), CD270 (HVEM), TL1A, CD127, IL-4R, GITR-L, CD160, CD258, TIM-4, CD153 (CD30L), CD200R (OX2R), CD44, ligands thereof, for functional fragments or variants thereof), a soluble cytokine (e.g., IL-2, IL-12, IL-6, IL-7, IL-15, IL-18, IL-21, GM-CSF, IL-18, IL-21, and IL-27, or functional fragments or variants thereof), a polypeptide involved in antigen presentation (e.g., CD64, MHC I, and MHC II, or functional fragments or variants thereof), a polypeptide involved in trafficking and/or migration (e.g., CD183, CCR2, CCR6, CD50, CD197, CD58, and CD62L, or functional fragments or variants thereof), or a polypeptide involved in dendritic cell targeting (e.g., TLR ligands, anti-DEC-205 antibody, and an anti-DC-SIGN antibody, or functional fragments or variants thereof).

The RNA ETP-CAR T cells of the invention have enhanced antigen presentation and/or T cell priming ability relative to a T cell which lacks the RNA encoding the ETP. When two or more ETPs are transiently transfected into a T cell, the additional ETPs enhance the antigen presentation and/or T cell priming ability of a T cell lacking the additional ETPs. In some embodiments, the T cell is transfected to transiently express a third distinct RNA comprising a nucleic acid sequence encoding an ETP which differs from the ETP encoded by the second RNA. In this case, the T cell has increased antigen presentation and/or T cell priming ability relative to a T cell comprising the first RNA and second RNA, but not the third RNA.

In some embodiments, the expression of the CAR or CARs does not substantially affect the level of expression of the ETP or ETPs in the RNA ETP-CAR T cell, wherein the CAR comprises an antigen binding domain that binds the antigen, and the expression of the ETP or ETPs does not substantially affect the level of expression or cell-killing function of the CAR or CARs in the RNA ETP-CAR T cell.

The RNA ETP-CAR T cells of the invention have, for example, increased efficacy in killing tumor cells and/or reducing tumor size and/or priming of T cells with a tumor antigen in a subject with a tumor relative to a RNA CAR T cell, i.e., a T cell transiently expressing the CAR alone.

The RNAs encoding the CAR or CARs and ETP or ETPs are transcribed from, e.g., an in vitro transcription vector, and introduced into T cells by, e.g., electroporation.

In another aspect, the invention provides compositions, for example, a pharmaceutical composition comprising a pharmaceutically acceptable carrier, comprising an RNA ETP-CAR T cell described herein.

In another aspect, the invention relates to method of generating a T cell having enhanced anti-tumor activity, the method comprising transiently transfecting a T cell with two or more distinct exogenous RNAs, wherein: (a) the first RNA comprises a nucleic acid sequence encoding a CAR comprising an extracellular domain, a transmembrane domain, and an intracellular signaling domain, and b) the second RNA comprises a nucleic acid sequence encoding an ETP, or a functional fragment or variant thereof.

In another aspect, the invention relates to a method of providing anti-tumor immunity in a subject comprising administering to the subject, for example, a human subject, an effective amount of a RNA ETP-CAR T cell described herein.

In another aspect, the invention relates to a method of treating a subject, for example, a human subject, having a disease associated with a disease-associated antigen comprising administering to the subject an effective amount of a RNA ETP-CAR T cell described herein. In some embodiments, the disease is a proliferative disease, a precancerous condition, or a non-cancer-related indication. In one embodiment, the cancer is a cancer described herein. In an embodiment, the non-cancer-related indication is a viral infection or a bacterial infection.

In another aspect, the invention relates to a method of enhancing epitope spreading in a subject, for example, a human subject, with cancer comprising administering to the subject the RNA ETP-CAR T cell described herein.

In another aspect, the invention relates to the RNA ETP-CAR T cells and RNA ETP-CAR T cell compositions and their use for preparing medicaments or use for treating, diseases associated with disease-associated antigens, such as cancer, autoimmune diseases, inflammatory diseases, and infectious diseases.

BRIEF DESCRIPTION OF THE FIGURES

FIG. 1 shows candidate molecules associated with various aspects of CTL priming for RNA engineering and use in conjunction with CARs. The exemplary molecules listed are highly upregulated in dendritic cells, which are potent professional antigen-presenting cells (APCs).

DETAILED DESCRIPTION

Definitions

Figure 2:
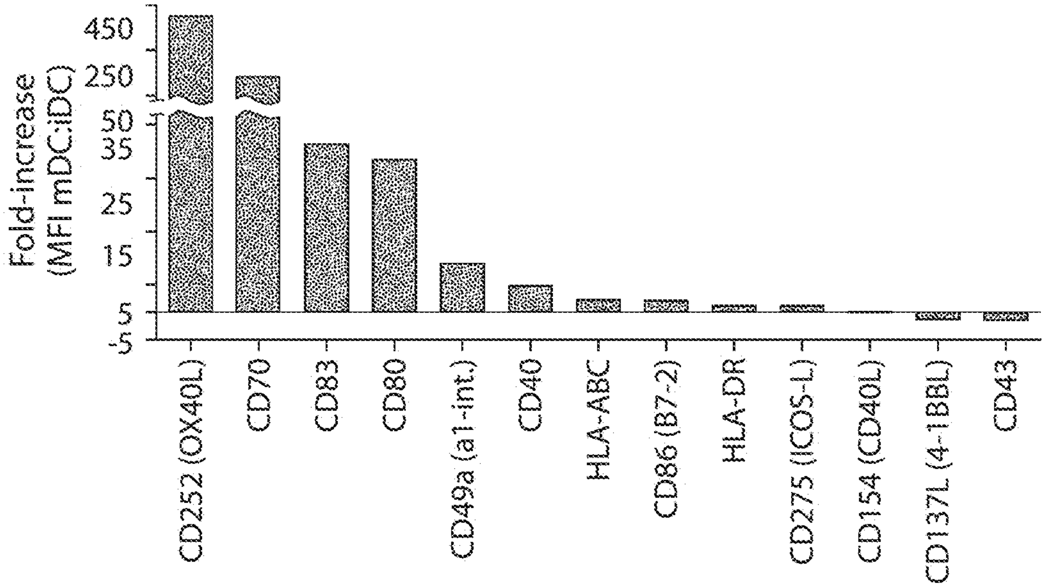
FIG. 2 is a bar graph showing the upregulation of costimulatory molecule expression in mature dendritic cells. Immature DCs were cultured from adherent monocytes in the presence of IL-4 and GM-CSF for 7 days. Mature DCs were first cultured in the presence of IL-4 and GM-CSF for 5 days, followed by the addition of TNFα, IL-1β, IL-6, and $PGE_2$ for an additional 2 days. Immature and mature DCs were stained with antibodies (Abs) specific for the indicated markers and analyzed by flow cytometry. The fold-increase of each marker was calculated as a ratio of marker expression in mature DCs over immature DCs.
Figure 3:
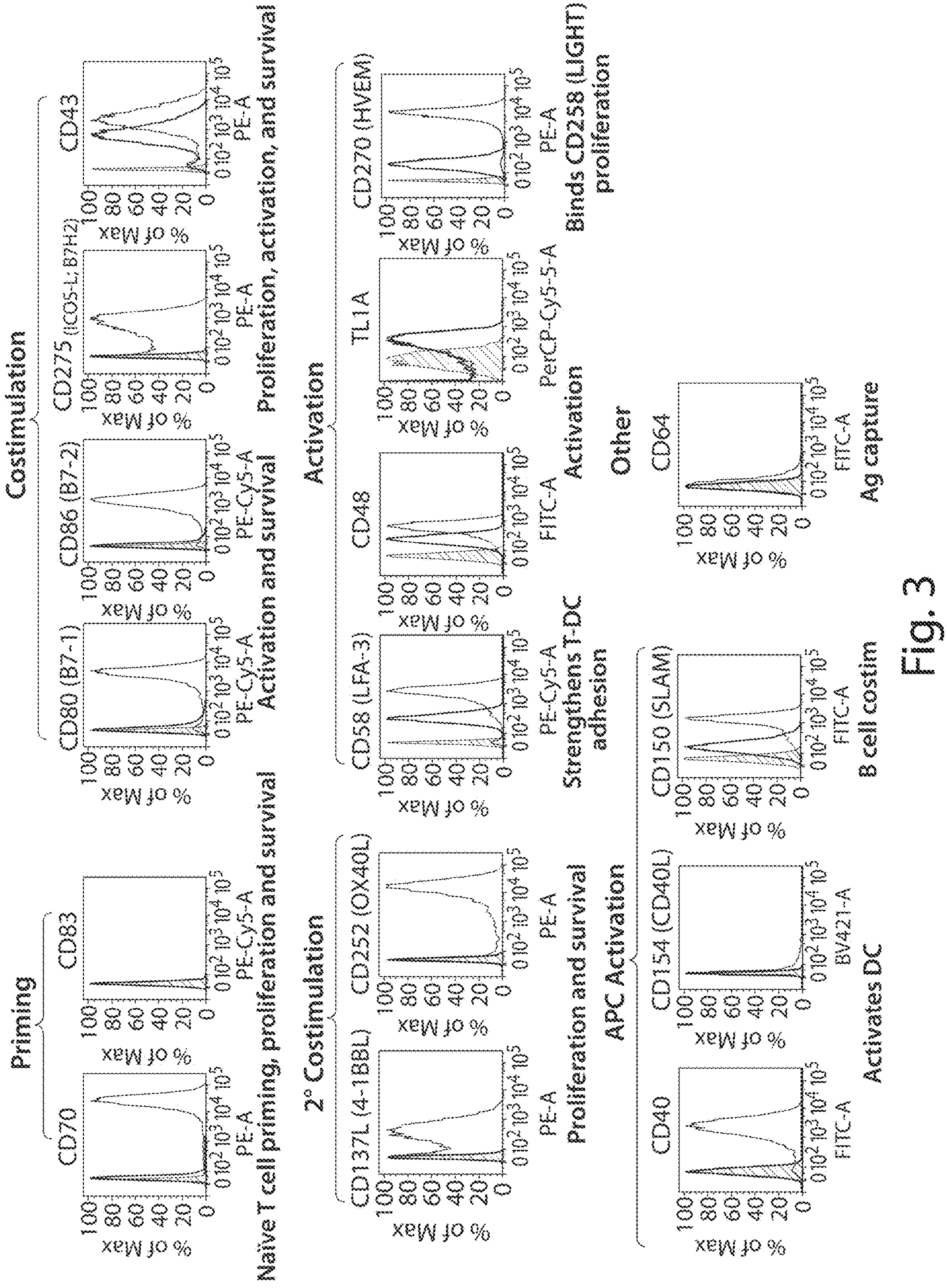
FIG. 3 shows the expression of CD70, CD83, CD80 (B7-1), CD86 (B7-2), CD275 (ICOS-L), CD43, CD137L (4-1BBL), CD252 (OX40L), CD58 (LFA-3), CD48, TL1A, CD270 (HVEM), CD40, CD154 (CD40L), CD150 (SLAM), and CD64 after electroporation of their RNAs into T cells. High quality mRNA encoding costimulatory molecules was produced following gene cloning into a plasmid DNA template. 8-10 μg of RNA was electroporated into $2.5\times10^6$ T cells using a BTX ECM 830 electroporator for a single pulse at 500 V for 0.7 ms. Electroporated T cells were then cultured overnight in standard T cell culture medium and then stained for respective molecule expression by flow cytometry. Filled lines display costimulatory molecule expression in T cells that were not stained. Also shown are T cells that were electroporated but without RNA and stained, and T cells that were electroporated with the indicated RNAs and stained.

Unless defined otherwise, all technical and scientific terms used herein have the same meaning as commonly understood by one of ordinary skill in the art to which the invention pertains.

The term "a" and "an" refers to one or to more than one (i.e., to at least one) of the grammatical object of the article. By way of example, "an element" means one element or more than one element.

The term "about" when referring to a measurable value such as an amount, a temporal duration, and the like, is meant to encompass variations of ±20% or in some instances ±10%, or in some instances ±5%, or in some instances ±1%, or in some instances ±0.1% from the specified value, as such variations are appropriate to perform the disclosed methods.

As used herein, a 5' cap (also termed an RNA cap, an RNA 7-methylguanosine cap or an RNA $m^7G$ cap) is a modified guanine nucleotide that has been added to the "front" or 5' end of a eukaryotic messenger RNA shortly after the start of transcription. The 5' cap consists of a terminal group which is linked to the first transcribed nucleotide. Its presence is critical for recognition by the ribosome and protection from RNases. Cap addition is coupled to transcription, and occurs co-transcriptionally, such that each influences the other. Shortly after the start of transcription, the 5' end of the mRNA being synthesized is bound by a cap-synthesizing complex associated with RNA polymerase. This enzymatic complex catalyzes the chemical reactions that are required for mRNA capping. Synthesis proceeds as a multi-step biochemical reaction. The capping moiety can be modified to modulate functionality of mRNA such as its stability or efficiency of translation.

As used herein. "polyadenylation" refers to the covalent linkage of a polyadenylyl moiety, or its modified variant, to a messenger RNA molecule. In eukaryotic organisms, most messenger RNA(mRNA) molecules are polyadenylated at the 3' end. The 3' poly(A) tail is a long sequence of adenine nucleotides (often several hundred) added to the pre-mRNA through the action of an enzyme, polyadenylate polymerase. In higher eukaryotes, the poly(A) tail is added onto transcripts that contain a specific sequence, the polyadenylation signal. The poly(A) tail and the protein bound to it aid in protecting mRNA from degradation by exonucleases. Polyadenylation is also important for transcription termination, export of the mRNA from the nucleus, and translation. Polyadenylation occurs in the nucleus immediately after transcription of DNA into RNA, but additionally can also occur later in the cytoplasm. After transcription has been terminated, the mRNA chain is cleaved through the action of an endonuclease complex associated with RNA polymerase. The cleavage site is usually characterized by the presence of the base sequence AAUAAA near the cleavage site. After the mRNA has been cleaved, adenosine residues are added to the free 3' end at the cleavage site.

The term "in vitro transcribed RNA" refers to RNA, preferably mRNA, that has been synthesized in vitro. Generally, the in vitro transcribed RNA is generated from an in vitro transcription vector. The in vitro transcription vector comprises a template that is used to generate the in vitro transcribed RNA.

The term "Chimeric Antigen Receptor" or alternatively a "CAR" refers to a recombinant polypeptide construct comprising at least an extracellular antigen binding domain, a transmembrane domain and a cytoplasmic signaling domain (also referred to as an intracellular signaling domain") comprising a functional signaling domain derived from a stimulatory molecule as defined below (also referred to herein as a "primary signaling domain"). In some embodiments, the stimulatory molecule is TCR zeta, FcR gamma, FcR beta, CD3 gamma, CD3 delta, CD3 epsilon, CD5, CD22, CD79a, CD79b, CD66d, 4-1BB or CD3-zeta. In a particular embodiment, the stimulatory molecule is the zeta chain associated with the T cell receptor complex. In one embodiment, the stimulatory molecule is 4-1BB. In one embodiment, the cytoplasmic signaling domain further comprises one or more functional signaling domains derived from at least one costimulatory molecule as defined below (also referred to as a "costimulatory signaling domain"). In one embodiment, the costimulatory molecule is chosen from a costimulatory molecule described herein, e.g., OX40, CD27, CD28, CD30, CD40, PD-1, CD2, CD7, CD258, NKG2C, B7-H3, a ligand that binds to CD83, ICAM-1, LFA-1 (CD11a/CD18), ICOS and 4-1BB (CD137), or any combination thereof. In one embodiment, the CAR comprises a chimeric fusion protein comprising an extracellular antigen recognition domain, a transmembrane domain and an intracellular signaling domain comprising a functional signaling domain derived from a stimulatory molecule (a primary signaling domain). In one embodiment, the CAR comprises a chimeric fusion protein comprising an extracellular antigen recognition domain, a transmembrane domain and an intracellular signaling domain comprising a functional signaling domain derived from a co-stimulatory molecule (a costimulatory signaling domain) and a functional signaling domain derived from a stimulatory molecule (a primary signaling domain). In one aspect, the CAR comprises a chimeric fusion protein comprising an extracellular antigen binding domain, a transmembrane domain and an intracellular signaling domain comprising two functional signaling domains derived from one or more costimulatory molecule(s) and a functional signaling domain derived from a stimulatory molecule. In one embodiment, the CAR comprises a chimeric fusion protein comprising an extracellular antigen binding domain, a transmembrane domain and an intracellular signaling domain comprising at least two functional signaling domains derived from one or more costimulatory molecule(s) and a functional signaling domain derived from a stimulatory molecule. In one embodiment the CAR comprises an optional leader sequence at the amino-terminus (N-ter) of the CAR fusion protein. In one embodiment, the CAR further comprises a leader sequence at the N-terminus of the extracellular antigen binding domain, wherein the leader sequence is optionally cleaved from the scFv domain during cellular processing and localization of the CAR to the cellular membrane. In one embodiment, the leader sequence comprises (e.g., consists of) the amino acid sequence of SEQ ID NO: 2. In one embodiment, the CAR is a regulatable chimeric antigen receptor (RCAR).

The term "regulatable chimeric antigen receptor (RCAR)," as that term is used herein, refers to a set of polypeptides, typically two in the simplest embodiments, which when expressed in a cell, e.g., an RCARX cell, provides the cell with specificity for a target cell, typically a cancer cell, and with regulatable intracellular signal generation or proliferation, which can optimize an immune effector property of the RCAR-expressing cell. An RCAR-expressing cell relies at least in part, on an antigen binding domain to provide specificity to a target cell that comprises the antigen bound by the antigen binding domain. In an embodiment, an RCAR includes a dimerization switch that, upon the presence of a dimerization molecule, can couple a polypeptide comprising an intracellular signaling domain to a polypeptide comprising an antigen binding domain.

The term "dimerization molecule," as that term is used herein, e.g., when referring to an RCAR, refers to a molecule that promotes the association of a first switch domain with a second switch domain. In embodiments, the dimerization molecule does not naturally occur in the subject, or does not occur in concentrations that would result in significant dimerization. In embodiments, the dimerization molecule is a small molecule, e.g., rapamycin or a rapalogue, e.g, RAD001.

The term "signaling domain" refers to the functional portion of a protein which acts by transmitting information within the cell to regulate cellular activity via defined signaling pathways by generating second messengers or functioning as effectors by responding to such messengers.

The term "antibody," as used herein, refers to a protein, or polypeptide sequence derived from an immunoglobulin molecule which specifically binds with an antigen. Antibodies can be polyclonal or monoclonal, multiple or single chain, or intact immunoglobulins, and may be derived from natural sources or from recombinant sources. Antibodies are typically tetramers of immunoglobulin molecules.

The term "antibody fragment" refers to at least one portion of an antibody, that retains the ability to specifically interact with (e.g., by binding, steric hinderance, stabilizing/destabilizing, spatial distribution) an epitope of an antigen. Examples of antibody fragments include, but are not limited to, Fab, Fab', $F(ab')_2$, Fv fragments, scFv antibody fragments, disulfide-linked Fvs (sdFv), a Fd fragment consisting of the VH and CHI domains, linear antibodies, single domain antibodies such as sdAb (either VL or VH), camelid VHH domains, multi-specific antibodies formed from antibody fragments such as a bivalent fragment comprising two Fab fragments linked by a disulfide brudge at the hinge region, and an isolated CDR or other epitope binding fragments of an antibody. An antigen binding fragment can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antigen binding fragments can also be grafted into scaffolds based on polypeptides such as a fibronectin type III (Fn3)(see U.S. Pat. No. 6,703,199, which describes fibronectin polypeptide minibodies). The term "scFv" refers to a fusion protein comprising at least one antibody fragment comprising a variable region of a light chain and at least one antibody fragment comprising a variable region of a heavy chain, wherein the light and heavy chain variable regions are contiguously linked, e.g., via a synthetic linker, e.g., a short flexible polypeptide linker, and capable of being expressed as a single chain polypeptide, and wherein the scFv retains the specificity of the intact antibody from which it is derived. Unless specified, as used herein an scFv may have the VL and VH variable regions in either order, e.g., with respect to the N-terminal and C-terminal ends of the polypeptide, the scFv may comprise VL-linker-VH or may comprise VH-linker-VL.

The portion of the CAR of the invention comprising an antibody or antibody fragment thereof may exist in a variety of forms where the antigen binding domain is expressed as part of a contiguous polypeptide chain including, for example, a single domain antibody fragment (sdAb), a single chain antibody (scFv), a humanized antibody or bispecific antibody (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426). In one aspect, the antigen binding domain of a CAR composition of the invention comprises an antibody fragment. In a further aspect, the CAR comprises an antibody fragment that comprises a scFv.

The term "antibody heavy chain," refers to the larger of the two types of polypeptide chains present in antibody molecules in their naturally occurring conformations, and which normally determines the class to which the antibody belongs.

The term "antibody light chain," refers to the smaller of the two types of polypeptide chains present in antibody molecules in their naturally occurring conformations. Kappa (κ) and lambda (λ) light chains refer to the two major antibody light chain isotypes.

The term "recombinant antibody" refers to an antibody which is generated using recombinant DNA technology, such as, for example, an antibody expressed by a bacteriophage or yeast expression system. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using recombinant DNA or amino acid sequence technology which is available and well known in the art.

The term "anti-cancer effect" refers to a biological effect which can be manifested by various means, including but not limited to, e.g., a decrease in tumor volume, a decrease in the number of cancer cells, a decrease in the number of metastases, an increase in life expectancy, decrease in cancer cell proliferation, decrease in cancer cell survival, or amelioration of various physiological symptoms associated with the cancerous condition. An "anti-cancer effect" can also be manifested by the ability of the peptides, polynucleotides, cells and antibodies in prevention of the occurrence of cancer in the first place. The term "anti-tumor effect" refers to a biological effect which can be manifested by various means, including but not limited to, e.g., a decrease in tumor volume, a decrease in the number of tumor cells, a decrease in tumor cell proliferation, or a decrease in tumor cell survival.

The term "autologous" refer to any material derived from the same individual to whom it is later to be re-introduced into the individual.

The term "allogeneic" refers to any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically.

The term "xenogeneic" refers to a graft derived from an animal of a different species.

The term "proliferative disease" refers to any disease or disorder including cancers, malignancies, benign growths and other conditions that result from hyperactivity or hyperplasia of somatic cells.

The term "cancer" refers to a disease characterized by the uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

The term "T cell priming" refers to the process by which a naive T cell undergoes clonal expansion and differentiation into an effector cytotoxic T cell (CTL) after being stimulated by contact with an antigen.

The term "Enhancer of T cell priming" or "ETP" refers to a molecule that, when introduced into a cell, enhances the cell's antigen presentation and T cell priming activities. Exemplary ETPs of the present invention include, but are not limited to, costimulatory molecules (e.g., CD70, CD83, CD80, CD86, CD40, CD154, CD137L (4-1BBL), CD252 (OX40L), CD275 (ICOS-L), CD54 (ICAM-1), CD49a, CD43, CD48, CD 112 (PVRL2), CD150 (SLAM), CD155 (PVR), CD265 (RANK), CD270 (HVEM), TL1A, CD127, IL-4R, GITR-L, CD160, CD258, TIM-4, CD153 (CD30L), CD200R (OX2R), CD44, and ligands thereof), soluble cytokines (e.g., IL-2, IL-12, IL-6, IL-7, IL-15, IL-18, IL-21, GM-CSF, IL-18, IL-21, IL-27), polypeptides involved in antigen presentation (e.g., CD64, MHC I, MHC II), polypeptides involved in trafficking and/or migration (e.g., CD183, CCR2, CCR6, CD50, CD197, CD58, CD62L), and polypeptides involved in dendritic cell targeting (e.g., TLR ligands, anti-DEC-205 antibody, anti-DC-SIGN antibody). Candidate ETPs can be tested for T cell priming activity using assays described in the Examples. T cells comprising a nucleic acid sequence encoding a CAR and a nucleic acid encoding an ETP are referred to herein as "ETP-CAR T cells". T cells transiently transfected with an RNA encoding a CAR and an RNA encoding an ETP are referred to herein as "RNA ETP-CAR T cells."

The term "epitope spreading" or "antigen spreading" refers to the ability of the immune system to attack new targets beyond that to which a vaccine is designed to attack, by recognizing antigenic fragments of killed cells as new targets.

The term "conservative sequence modifications" refers to amino acid modifications that do not significantly affect or alter the binding characteristics of the antibody or antibody fragment containing the amino acid sequence. Such conservative modifications include amino acid substitutions, additions and deletions. Modifications can be introduced into an antibody or antibody fragment of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine).

The term "stimulation," refers to a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate the altered expression of certain molecules, such as downregulation of TGF-β, and/or reorganization of cytoskeletal structures, and the like.

The term "stimulatory molecule," refers to a molecule expressed by an immune cell, e.g., a T cell, a NK cell, or a B cell, that provide the cytoplasmic signaling sequence(s) that regulate activation of the immune cellin a stimulatory way for at least some aspect of the immune cell signaling pathway. In one aspect, the signal is a primary signal that is initiated by, for instance, binding of a TCR/CD3 complex with an MHC molecule loaded with a peptide, and which leads to mediation of a T cell response, including, but not limited to, proliferation, activation, differentiation, and the like. Primary cytoplasmic signaling sequences (primary signaling domain) that act in a stimulatory manner may contain signaling motifs which are known as immunoreceptor tyrosine-based activation motifs or ITAMs. Examples of ITAM containing cytoplasmic signaling sequences that are of particular use in the invention include those derived from CD3 zeta, common FcR gamma (FCER1G), Fc gamma RIIa, FcR beta (Fc Epsilon R1b), CD3 gamma, CD3 delta, CD3 epsilon, CD79a, CD79b, DAP10, and DAP12. In one embodiment, the cytoplasmic signaling molecule in any one or more CARs of the invention comprises a cytoplasmic signaling sequence derived from CD3-zeta. In one embodiment, the cytoplasmic signaling sequence derived from CD3-zeta is the sequence provided as SEQ ID NO: 18 or the equivalent residues from a non-human species, e.g., mouse, rodent, monkey, ape and the like.

The term "antigen presenting cell," refers to an immune system cell such as an accessory cell (e.g., a B-cell, a dendritic cell, and the like) that displays foreign antigens complexed with major histocompatibility complexes (MHC's) on their surfaces. T-cells may recognize these complexes using their T-cell receptors (TCRs). APCs process antigens and present them to T-cells.

The term "zeta" or alternatively "zeta chain", "CD3-zeta" or "TCR-zeta" is defined as the protein provided as GenBank Acc No. BAG36664.1, or the equivalent residues from a non-human species, e.g., mouse, rodent, monkey, ape and the like, and a "zeta stimulatory domain" or alternatively a "CD3-zeta stimulatory domain" or a "TCR-zeta stimulatory domain" is defined as the amino acid residues from the cytoplasmic domain of the zeta chain, or functional derivatives thereof, that are sufficient to functionally transmit an initial signal necessary for T cell activation. In one aspect the cytoplasmic domain of zeta comprises residues 52 through 164 of GenBank Acc No. BAG36664.1 or the equivalent residues from a non-human species, e.g., mouse, rodent, monkey, ape and the like, that are functional orthologs thereof. In one aspect, the "zeta stimulatory domain" or a "CD3-zeta stimulatory domain" is the sequence provided as SEQ ID NO:18.

The term a "costimulatory molecule" refers to a cognate binding partner on a T cell that specifically binds with a costimulatory ligand, thereby mediating a costimulatory response by the T cell, such as, but not limited to, proliferation. Costimulatory molecules are cell surface molecules other than antigen receptors or their ligands that are required for an efficient immune response. Costimulatory molecules, e.g., that may confer T cell priming activity when expressed in an ETP-CAR T cell as described herein, include, but are not limited to an MHC class I molecule, BTLA and a Toll ligand receptor, as well as CD70, CD83, CD80, CD86, CD40, CD154, CD137L (4-1BBL), CD252 (OX40L), CD275 (ICOS-L), CD54 (ICAM-1), CD49a, CD43, CD48, CD43, CD48, CD 112 (PVRL2), CD150 (SLAM), CD155 (PVR), CD265 (RANK), CD270 (HVEM), TL1A, CD 112 (PVRL2), CD150 (SLAM), CD155 (PVR), CD265 (RANK), CD270 (HVEM), TL1A, CD127, IL-4R, GITR-L, CD160, CD258, TIM-4, CD153 (CD30L), CD200R (OX2R), and CD44.

A costimulatory intracellular signaling domain of a CAR described herein can be the intracellular portion of a costimulatory molecule. A costimulatory molecule can be represented in the following protein families: TNF receptor proteins, Immunoglobulin-like proteins, cytokine receptors, integrins, signaling lymphocytic activation molecules (SLAM proteins), and activating NK cell receptors. Examples of such molecules include CD27, CD28, 4-1BB (CD137), OX40, GITR, CD30, CD40, ICOS, BAFFR, HVEM, ICAM-1, lymphocyte function-associated antigen-1 (LFA-1), CD2, CDS, CD7, CD287, LIGHT, NKG2C, NKG2D, SLAMF7, NKp80, NKp30, NKp44, NKp46, CD160, B7-H3, and a ligand that specifically binds with CD83, and the like.

The intracellular signaling domain can comprise the entire intracellular portion, or the entire native intracellular signaling domain, of the molecule from which it is derived, or a functional fragment or derivative thereof.

The term "4-1BB" refers to member of the TNFR superfamily with an amino acid sequence provided as GenBank accno. AAA62478.2, or the equivalent residues from a non-human species, e.g., mouse, rodent, monkey, ape and the like; and a "4-1BB costimulatory domain" are defined amino acid residues 214-255 of GenBank accno. AAA62478.2, or the equivalent residues from a non-human species, e.g., mouse, rodent, monkey, ape and the like. In one aspect, the "4-1BB costimulatory domain" is the sequence provided as SEQ ID NO: 14 or the equivalent residues from a non-human species, e.g., mouse, rodent, monkey, ape and the like.

The term "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA, and mRNA) or a defined sequence of amino acids and the biological properties resulting therefrom. Thus, a gene, cDNA, or RNA, encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleic acid sequence encoding an amino acid sequence" includes all nucleic acid sequences that are degenerate versions of each other and that encode the same amino acid sequence. The phrase nucleic acid sequence that encodes a protein or a RNA may also include introns to the extent that the nucleotide sequence encoding the protein may in some version contain an intron (s).

The term "effective amount" or "therapeutically effective amount" are used interchangeably herein, and refer to an amount of a compound, formulation, material, or composition, as described herein effective to achieve a particular biological result. Such results may include, but are not limited to, the inhibition of virus infection as determined by any means suitable in the art.

The term "endogenous" refers to any material from or produced inside an organism, cell, tissue or system.

The term "exogenous" refers to any material introduced from or produced outside an organism, cell, tissue or system.

The term "expression" refers to the transcription and/or translation of a particular nucleotide sequence driven by its promoter.

The term "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

The term "homologous" refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Humanized" forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies and antibody fragments thereof are human immunoglobulins (recipient antibody or antibody fragment) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies/antibody fragments can comprise residues which are found neither in the recipient antibody nor in the imported CDR or framework sequences. These modifications are made to further refine and optimize antibody or antibody fragment performance. In general, the humanized antibody or antibody fragment thereof will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody or antibody fragment can also comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

The term "variant," as used with respect to an ETP, refers to an RNA or polypeptide that differs from a wild-type ETP encoding RNA or polypeptide respectively, but retains essential properties of the wild-type ETP (e.g., ability to enhance antigen presentation and/or T cell priming).

The term "fully human" refers to an immunoglobulin, such as an antibody or antibody fragment, where the whole molecule is of human origin or consists of an amino acid sequence identical to a human form of the antibody or immunoglobulin.

The term "functional fragment," in connection with an ETP, is intended to mean a portion of the ETP that maintains the ability to enhance T cell priming.

The term "isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "lentivirus" refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses.

The term "lentiviral vector" refers to a vector derived from at least a portion of a lentivirus genome, including especially a self-inactivating lentiviral vector as provided in Milone et al., Mol. Ther. 17(8): 1453-1464 (2009). Other examples of lentivirus vectors that may be used in the clinic, include but are not limited to, e.g., the LENTIVECTOR® gene delivery technology from Oxford BioMedica, the LENTIMAX™ vector system from Lentigen and the like. Nonclinical types of lentiviral vectors are also available and would be known to one skilled in the art.

"Membrane anchor" or "membrane tethering domain", as that term is used herein, refers to a polypeptide or moiety, e.g., a myristoyl group, sufficient to anchor an extracellular or intracellular domain to the plasma membrane.

"Substantially complementary", as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a gene that is normally transcribed in cells (the open reading frame), including 5' and 3' UTRs. The primers can also be designed to amplify a portion of a gene that encodes a particular domain of interest. In one embodiment, the primers are designed to amplify the coding region of a human cDNA, including all or portions of the 5' and 3' UTRs. Primers useful for PCR are generated by synthetic methods that are well known in the art.

The term "substantially" refers to degree of variations of +/− by about 20%, about 25%, about 30%, about 35%, about 40%, about 45%, about 50%, or more. In one embodiment, an ETP co-expressed with a CAR in a T cell does not inhibit the cell killing function of a CAR by more than about 40%.

"Forward primers" are primers that contain a region of nucleotides that are substantially complementary to nucleotides on the DNA template that are upstream of the DNA sequence that is to be amplified.

"Upstream" is used herein to refer to a location 5, to the DNA sequence to be amplified relative to the coding strand.

"Reverse primers" are primers that contain a region of nucleotides that are substantially complementary to a double-stranded DNA template that are downstream of the DNA sequence that is to be amplified.

"Downstream" is used herein to refer to a location 3' to the DNA sequence to be amplified relative to the coding strand.

The term "operably linked" or "transcriptional control" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Operably linked DNA sequences can be contiguous with each other and, where necessary to join two protein coding regions, are in the same reading frame.

The term "parenteral" administration of an immunogenic composition includes, e.g., subcutaneous (s.c.), intravenous (i.v.), intramuscular (i.m.), or intrasternal injection, or infusion techniques.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, recombinant peptides, or a combination thereof.

The term "promoter" refers to a DNA sequence recognized by the synthetic machinery of the cell, or introduced synthetic machinery, required to initiate the specific transcription of a polynucleotide sequence.

The term "promoter/regulatory sequence" refers to a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

The term "flexible polypeptide linker" as used in the context of a scFv refers to a peptide linker that consists of amino acids such as glycine and serine residues used alone or in combination, to link variable heavy and variable light chain regions together. In one embodiment, the flexible polypeptide linker is a Gly/Ser linker and comprises the amino acid sequence (Gly-Gly-Gly-Ser)n, where n is a positive integer equal to or greater than 1. For example, n=1, n=2, n=3, n=4, n=5 and n=6, n=7, n=8, n=9 and n=10. In one embodiment, the flexible polypeptide linkers include, but are not limited to, (Gly4 Ser)4 or (Gly4 Ser)3 In another embodiment, the linkers include multiple repeats of (Gly2Ser), (GlySer) or (Gly3Ser). Also included within the scope of the invention are linkers described in WO2012/138475, incorporated herein by reference).

The term "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the membrane of a cell.

The term "subject" refers to any living organisms in which an immune response can be elicited (e.g., mammals, human).

The term "switch domain," as that term is used herein, e.g., when referring to an RCAR, refers to an entity, typically a polypeptide-based entity, that, in the presence of a dimerization molecule, associates with another switch domain. The association results in a functional coupling of a first entity linked to, e.g., fused to, a first switch domain, and a second entity linked to, e.g., fused to, a second switch domain. A first and second switch domain are collectively referred to as a dimerization switch. In embodiments, the first and second switch domains are the same as one another, e.g., they are polypeptides having the same primary amino acid sequence, and are referred to collectively as a homodimerization switch. In embodiments, the first and second switch domains are different from one another, e.g., they are polypeptides having different primary amino acid sequences, and are referred to collectively as a heterodimerization switch. In embodiments, the switch is intracellular. In embodiments, the switch is extracellular. In embodiments, the switch domain is a polypeptide-based entity, e.g., FKBP or FRB-based, and the dimerization molecule is small molecule, e.g., a rapalogue. In embodiments, the switch domain is a polypeptide-based entity, e.g., an scFv that binds a myc peptide, and the dimerization molecule is a polypeptide, a fragment thereof, or a multimer of a polypeptide, e.g., a myc ligand or multimers of a myc ligand that bind to one or more myc scFvs. In embodiments, the switch domain is a polypeptide-based entity, e.g., myc receptor, and the dimerization molecule is an antibody or fragments thereof, e.g., myc antibody.

The term "substantially purified" cell refers to a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some aspects, the cells are cultured in vitro. In other aspects, the cells are not cultured in vitro.

The term "therapeutic" as used herein means a treatment. A therapeutic effect is obtained by reduction, suppression, remission, or eradication of a disease state.

The term "prophylaxis" as used herein means the prevention of or protective treatment for a disease or disease state.

In the context of the present invention, "tumor antigen" or "hyperproliferative disorder antigen" or "antigen associated with a hyperproliferative disorder" refers to antigens that are common to specific hyperproliferative disorders. In certain aspects, the hyperproliferative disorder antigens of the present invention are derived from, cancers including but not limited to primary or metastatic melanoma, thymoma, lymphoma, sarcoma, lung cancer, liver cancer, non-Hodgkin's lymphoma, non-Hodgkins lymphoma, leukemias, uterine cancer, cervical cancer, bladder cancer, kidney cancer and adenocarcinomas such as breast cancer, prostate cancer, ovarian cancer, pancreatic cancer, and the like.

The term "transfected" refers to a process by which exogenous nucleic acid is transferred or introduced into the host cell. A "transfected" cell is one which has been transfected with exogenous nucleic acid. The cell includes the primary subject cell and its progeny.

As used herein, "transient" refers to expression of a non-integrated transgene for a period of hours, days or weeks, wherein the period of time of expression is less than the period of time for expression of the gene if integrated into the genome or contained within a stable plasmid replicon in the host cell.

As used herein, the terms "treat", "treatment" and "treating" refer to the reduction or amelioration of the progression, severity and/or duration of a proliferative disorder, or the amelioration of one or more symptoms (preferably, one or more discernible symptoms) of a proliferative disorder resulting from the administration of one or more therapies (e.g., one or more therapeutic agents such as a CAR of the invention). In specific embodiments, the terms "treat", "treatment" and "treating" refer to the amelioration of at least one measurable physical parameter of a proliferative disorder, such as growth of a tumor, not necessarily discernible by the patient. In other embodiments the terms "treat", "treatment" and "treating"-refer to the inhibition of the progression of a proliferative disorder, either physically by, e.g., stabilization of a discernible symptom, physiologically by, e.g., stabilization of a physical parameter, or both. In other embodiments the terms "treat", "treatment" and "treating" refer to the reduction or stabilization of tumor size or cancerous cell count.

The term "specifically binds," refers to an antibody, or a ligand, which recognizes and binds with a binding partner (e.g., a tumor antigen) protein present in a sample, but which antibody or ligand does not substantially recognize or bind other molecules in the sample.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Overview

The present invention is based on the discovery that the anti-tumor activities of T cells that express nucleic acid sequences encoding CARs can be further enhanced by the co-expression of nucleic acid sequences encoding molecules that enhance T cell priming (i.e., hereafter, "ETPs"), e.g., molecules involved in cellular co-stimulation and/or antigen presentation. Such T cells are referred to herein as "ETP-CAR T cells". In this way, the ETP-CAR T cells are armed not only with CAR T cell-directed cell killing ability, they also exhibit enhanced antigen presenting function, allowing for ETP-CAR T cell-mediated priming of non-engineered tumor-reactive T cells, both naïve and antigen experienced. That is, the ETP-CAR T cells are dual functional T cells with both killer and "professional" APC function, creating a transient therapy with permanent anti-tumor effects. In embodiments, the T cells transiently express RNAs encoding CARs and/or RNAs encoding ETPs. In other embodiments, the T cells exhibit prolonged expression of CAR and/or ETPs, e.g., by virus-mediated transduction of nucleic acids encoding CARs and/or ETPs.

It was further discovered that ETP-CAR T cells, e.g., RNA ETP-CAR T cells, provide the added benefit of enhancing epitope spreading, which is classically defined by an immune response to a single antigen leading to the development of immunity against other antigens on the same tumor (Lehmann, Forsthuber et al. 1992, Kaufman, Clare-Salzler et al. 1993, Tisch, Yang et al. 1993, McRae, Vanderlugt et al. 1995, Vanderlugt and Miller 2002). Without being bound by theory, it is believed that, in the context of tumor rejection, ETP-CAR T cells, e.g., RNA ETP-CAR T cells, reacting specifically to a given tumor antigen via the CAR induces an inflammatory cascade at the site of antigen encounter. This then results in tissue destruction and the release of tumor antigens that may be processed and cross-presented by ETP-CAR T cells (which have been endowed with enhanced antigen-presenting and T cell priming abilities via the ETP component), e.g., RNA ETP-CAR T cells, and other antigen-presenting cells, thus amplifying the response due to the recruitment of a diversified repertoire of T and B cells reacting to subdominant and/or cryptic tumor-derived epitopes.

The T cells provided herein can be genetically modified, e.g., by transfection or transduction, to express a nucleic acid sequence encoding a CAR described herein and a nucleic acid sequence encoding an ETP described herein. Depending on the clinical context, e.g., patient's condition or condition to be treated, prolonged or permanent expression of the CAR and/or the ETP may be desired, e.g., for robust and long-lasting CAR activity, e.g., anti-tumor activity, and ETP-based T cell priming activity. In such embodiments, the T cells can be genetically modified, e.g., transduced, e.g., virally transduced, using vectors comprising nucleic acid sequences encoding a CAR and/or ETP described herein to confer prolonged expression of the CAR and/or the ETP.

Alternatively, in some embodiments, transient expression of the CAR and/or the ETP may be desired. The transient presence of RNA ETP-CAR T cells (i.e., the reversibility of CAR and ETP expression) in a host presents a flexible platform for the fine tuning of and patient-tailored adoptive T cell therapy, which distinct from the strategy of permanently genetically modifying T cells with, e.g., virus-mediated CAR delivery. For example, RNA ETP-CAR T cells can be administered to subjects as needed (e.g., with single or multiple infusions), and the expression of the components (ETP and CAR) can be controlled by altering the amount of RNA encoding each for fine tuning of CAR-based cell killing or ETP-based T cell priming activity, depending on the patient's condition. This strategy may be particularly attractive in certain clinical contexts, for example, when there is a desire to limit the duration of on-target off-tumor toxicity, particularly in cases where disease-associated antigens are also expressed on normal tissues.

Engineered T Cell Receptors

The present invention provides nucleic acid sequences encoding engineered T cell receptors, e.g., T cell receptors (TCR), TCRs modified as described herein, and chimeric antigen receptors (CAR) for expression in T cells with nucleic acid sequences encoding polypeptides that enhance T cell priming (ETP). Components of the TCR and CARs are further described herein.

The TCR is a disulfide-linked membrane-anchored heterodimer present on T cell lymphocytes, and normally consisting of an alpha (α) chain and a beta (β) chain. Each chain comprises a variable (V) and a constant (C) domain, wherein the variable domain recognizes an antigen, or an MHC-presented peptide. TCRα and TCRβ chains with a known specificity or affinity for specific antigens, e.g., tumor antigens described herein, can be introduced to a T cells using the methods described herein. TCRα and TCRβ chains having a desired, e.g., increased, specificity or affinity for a particular antigen can be isolated using standard molecular cloning techniques known in the art. Other modifications that increase specificity, avidity, or function of the TCRs or the engineered T cells expressing the TCRs can be readily envisioned by the ordinarily skilled artisan, e.g., promoter selection for regulated expression, mutations in the antigen binding regions of the TCRα and TCRβ chains. Any isolated or modified TCRα and TCRβ chain can be operably linked to or can associate with one or more intracellular signaling domains described herein. Signaling can be mediated through interaction between the antigen-bound as heterodimer to CD3 chain molecules, e.g., CD3zeta (ζ). Upon binding of a TCR to its antigen, a signal transduction cascade is initiated that can result in T cell activation, T cell expansion, and anticancer effect, e.g., increased cytolytic activity against cancer cells.

Accordingly, in an embodiment, a T cell comprises a nucleic acid sequence encoding a TCR, e.g., a modified TCR that targets a tumor antigen described herein, and a nucleic acid sequence encoding an ETP. In any of the embodiments described herein, a TCR can be substituted for a CAR described herein to generate a T cell with enhanced T cell priming activity. An engineered TCR described herein can be substituted for a CAR in any of the embodiments described herein.

Chimeric Antigen Receptor (CAR)

The present invention provides a nucleic acid sequence, e.g., a DNA or an RNA construct, encoding a CAR, wherein the CAR further comprises an antibody fragment that binds to a disease-associated antigen. In one embodiment, the sequence encoding the antibody fragment is contiguous with, and in the same reading frame as a nucleic acid sequence encoding an intracellular domain. The intracellular domain comprises, a costimulatory signaling region and/or a zeta chain. The costimulatory signaling region refers to a portion of the CAR comprising the intracellular domain of a costimulatory molecule.

In one embodiment, the CAR construct comprises an optional leader sequence, an extracellular antigen binding domain, a hinge, a transmembrane domain, and an intracellular stimulatory domain. In one aspect, the CAR construct comprises an optional leader sequence, an extracellular antigen binding domain, a hinge, a transmembrane domain, an intracellular costimulatory domain and an intracellular stimulatory domain.

An exemplary leader sequence is provided as SEQ ID NO: 2. An exemplary hinge/spacer sequence is provided as SEQ ID NO: 4, SEQ ID NO: 6, or SEQ ID NO: 8. An exemplary transmembrane domain sequence is provided as SEQ ID NO: 12. An exemplary sequence of the intracellular stimulatory domain, e.g., intracellular costimulatory domain, of the 4-1BB protein is provided as SEQ ID NO: 14. Another exemplary sequence of an intracellular stimulatory domain, e.g., costimulatory signaling domain, of the CD27 protein is provided as SEQ ID NO: 16. An exemplary CD3zeta domain sequence is provided as SEQ ID NO: 18 or 20.

Exemplary transmembrane domains that can be used in the CAR include, but are not limited to, a transmembrane domain from alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, and the like.

Exemplary intracellular domains that can be used in the CAR include, but are not limited to, one or more intracellular signaling domains including, but not limited to, e.g., CD3-zeta, CD28, 4-1BB, and the like. In some instances, the CAR can comprise any combination of CD3-zeta, CD28, 4-1BB, and the like.

Exemplary costimulatory signaling domains that can be used in the CAR include, but are not limited to, any combination of OX40, CD27, CD28, CD30, CD40, PD-1, CD2, CD7, CD258, NKG2C, B7-H3, a ligand that binds to CD83, ICAM-1, LFA-1 (CD11a/CD18), ICOS, 4-1BB (CD137), and the like.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The present invention includes an RNA construct that can be directly transfected or electroporated into a cell. A method for generating mRNA for use in transfection involves in vitro transcription (IVT) of a template with specially designed primers, followed by polyA addition, to produce a construct containing 3' and 5' untranslated sequence ("UTR"), a 5' cap and/or Internal Ribosome Entry Site (IRES), the gene to be expressed, and a polyA tail, typically 50-2000 bases in length. RNA so produced can efficiently transfect different kinds of cells. In one embodiment, the template includes sequences for the CAR.

Antigen Binding Domain

In one embodiment, the CAR of the invention comprises a target-specific binding element otherwise referred to as an antigen binding domain. The choice of moiety depends upon the type and number of ligands that define the surface of a target cell. For example, the antigen binding domain may be chosen to recognize a ligand that acts as a cell surface marker on target cells associated with a particular disease state. Thus, examples of cell surface markers that may act as ligands for the antigen moiety domain in the CAR of the invention include those associated with viral, bacterial and parasitic infections, autoimmune disease, and cancer cells.

In another embodiment, the CAR-mediated T-cell response can be directed to an antigen of interest by way of engineering an antigen binding domain that specifically binds a desired antigen into the CAR.

The present invention provides CAR comprising an antigen binding domain on the CAR that is specific for a tumor antigen. There are two classes of tumor antigens that can be targeted by the CARs of the instant invention: (1) tumor antigens that are expressed on the surface of cancer cells; and (2) tumor antigens that itself is intracellar, however, a fragment of such antigen (peptide) is presented on the surface of the cancer cells by MHC (major histocompatibility complex).

Accordingly, the present invention provides CARs that target the following cancer associated antigens (tumor antigens): CD19, CD123, CD22, CD30, CD171, CS-1, CLL-1 (CLECL1), CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-11Ra, PSCA, VEGFR2, LewisY, CD24, PDGFR-beta, PRSS21, SSEA-4, CD20, Folate receptor alpha, ERBB2 (Her2/neu), MUC1, EGFR, NCAM, Prostase, PAP, ELF2M, Ephrin B2, IGF-I receptor, CAIX, LMP2, gp100, bcr-abl, tyrosinase, EphA2, Fucosyl GM1, sLe, GM3, TGS5, HMWMAA, o-acetyl-GD2, Folate receptor beta, TEM1/CD248, TEM7R, CLDN6, TSHR, GPRC5D, CXORF61, CD97, CD179a, ALK, Plysialic acid, PLAC1, GloboH, NY-BR-1, UPK2, HAVCR1, ADRB3, PANX3, GPR20, LY6K, OR51E2, TARP, WT1, NY-ESO-1, LAGE-1a, legumain, HPV E6, E7, MAGE-A1, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYPiB1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, and IGLL1.

The present invention also provides a CAR comprising an antigen binding domain that is specific for a viral antigen or a bacterial antigen.

The antigen binding domain can be any domain that binds to the antigen including but not limited to antigen binding domains derived from any one or more of monoclonal antibodies, polyclonal antibodies, recombinant antibodies, human antibodies, humanized antibodies, and fragments thereof, including but not limited to single-domain antibodies such as a heavy chain variable domain (VH), a light chain variable domain (VL) and a variable domain (VHH) of camelid derived nanobody, and to alternative scaffolds known in the art that function as antigen binding domains, such as recombinant fibronectin domains, and the like. In some instances, it is beneficial for the antigen binding domain to be derived from the same species in which the CAR will ultimately be used in. For example, for use in humans, it may be beneficial for the antigen binding domain of the CAR to comprise human or humanized residues for the antigen binding domain of an antibody or antibody fragment. Thus, in one aspect, the antigen binding domain comprises a humanized antibody or an antibody fragment.

In other embodiments, a non-human antibody is humanized, where specific sequences or regions of the antibody are modified to increase similarity to an antibody naturally produced in a human or fragment thereof. In one aspect, the antigen binding domain is humanized.

A humanized antibody can be produced using a variety of techniques known in the art, including but not limited to, CDR-grafting (see, e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, Molecular Immunology, 28(4/5):489-498; Studnicka et al., 1994, Protein Engineering, 7(6):805-814; and Roguska et al., 1994, PNAS, 91:969-973, each of which is incorporated herein by its entirety by reference), chain shuffling (see, e.g., U.S. Pat. No. 5,565,332, which is incorporated herein in its entirety by reference), and techniques disclosed in, e.g., U.S. Patent Application Publication No. US2005/0042664, U.S. Patent Application Publication No. US2005/0048617, U.S. Pat. Nos. 6,407,213, 5,766,886, International Publication No. WO 9317105, Tan et al., 2002, J. Immunol., 169:1119-25; Caldas et al., 2000, Protein Eng., 13(5):353-60; Morea et al., 2000, Methods, 20:267-79; Baca et al., 1997, J. Biol. Chem., 272:10678-84; Roguska et al., 1996, Protein Eng., 9(10):895-904; Couto et al., 1995, Cancer Res., 55:5973s-5977; Couto et al., 1995, Cancer Res., 55(8):1717-22; Sandhu 1994 Gene, 150(2):409-10; and Pedersen et al., 1994, J. Mol. Biol., 235(3):959-73, each of which is incorporated herein in its entirety by reference. Often, framework residues in the framework regions will be substituted with the corresponding residue from the CDR donor antibody to alter, for example improve, antigen binding. These framework substitutions are identified by methods well-known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature, 332:323, which are incorporated herein by reference in their entireties.)

A humanized antibody or antibody fragment has one or more amino acid residues remaining in it from a source which is nonhuman. These nonhuman amino acid residues are often referred to as “import” residues, which are typically taken from an “import” variable domain. As provided herein, humanized antibodies or antibody fragments comprise one or more CDRs from nonhuman immunoglobulin molecules and framework regions wherein the amino acid residues comprising the framework are derived completely or mostly from human germline. Multiple techniques for humanization of antibodies or antibody fragments are well-known in the art and can essentially be performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody, i.e., CDR-grafting (EP 239,400; PCT Publication No. WO 91/09967; and U.S. Pat. Nos. 4,816,567; 6,331,415; 5,225,539; 5,530,101; 5,585,089; 6,548,640, the contents of which are incorporated herein by reference herein in their entirety). In such humanized chimeric antibodies and antibody fragments, substantially less than an intact human variable domain has been substituted by the corresponding sequence from a nonhuman species. In practice, humanized antibodies are typically human antibodies in which some CDR residues and possibly some framework (FR) residues are substituted by residues from analogous sites in rodent antibodies. Humanization of antibodies and antibody fragments can also be achieved by veneering or resurfacing (EP 592,106; EP 519,596; Padlan, 1991, Molecular Immunology, 28(4/5): 489-498; Studnicka et al., Protein Engineering, 7(6):805-814 (1994); and Roguska et al., PNAS, 91:969-973 (1994)) or chain shuffling (U.S. Pat. No. 5,565,332), the contents of which are incorporated herein by reference herein in their entirety.

The choice of human variable domains, both light and heavy, to be used in making the humanized antibodies is to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151:2296 (1993); Chothia et al., J. Mol. Biol., 196:901 (1987), the contents of which are incorporated herein by reference herein in their entirety). Another method uses a particular framework derived from the consensus sequence of all human antibodies of a particular subgroup of light or heavy chains. The same framework may be used for several different humanized antibodies (see, e.g., Carter et al., Proc. Natl. Acad. Sci. USA, 89:4285 (1992); Presta et al., J. Immunol., 151:2623 (1993), the contents of which are incorporated herein by reference herein in their entirety).

In certain embodiments, the portion of the CAR composition of the invention that comprises an antibody fragment is humanized with retention of high affinity for the target antigen and other favorable biological properties. According to one aspect of the invention, humanized antibodies and antibody fragments are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind the target antigen. In this way, FR residues can be selected and combined from the recipient and import sequences so that the desired antibody or antibody fragment characteristic, such as increased affinity for the target antigen, is achieved. In general, the CDR residues are directly and most substantially involved in influencing antigen binding.

In another embodiments, the antibodies of the invention may exist in a variety of other forms including, for example, Fv, Fab, and (Fab')2, as well as bi-functional (i.e. bi-specific) hybrid antibodies (e.g., Lanzavecchia et al., Eur. J. Immunol. 17, 105 (1987)). In one aspect, the antibody fragment provided herein is a scFv. In some instances, a human scFv may also be derived from a yeast display library.

In some instances, scFvs can be prepared according to method known in the art (see, for example, Bird et al., (1988) Science 242:423-426 and Huston et al., (1988) Proc. Natl. Acad. Sci. USA 85:5879-5883). ScFv molecules can be produced by linking VH and VL regions together using flexible polypeptide linkers. The scFv molecules comprise flexible polypeptide linker (e.g., a Ser-Gly linker) with an optimized length and/or amino acid composition. The flexible polypeptide linker length can greatly affect how the variable regions of an scFv fold and interact. In fact, if a short polypeptide linker is employed (e.g., between 5-10 amino acids, intrachain folding is prevented. Interchain folding is also required to bring the two variable regions together to form a functional epitope binding site. For examples of linker orientation and size see, e.g., Hollinger et al. 1993 Proc Natl Acad. Sci. U.S.A. 90:6444-6448, U.S. Patent Application Publication Nos. 2005/0100543, 2005/0175606, 2007/0014794, and PCT publication Nos. WO2006/020258 and WO2007/024715, is incorporated herein by reference.

The scFv can comprise a polypeptide linker sequence of at least 1, 2, 3, 4, 5, 6, 7, 8, 9, 10, 11, 12, 13, 14, 15, 16, 17, 18, 19, 20, 25, 30, 35, 40, 45, 50, or more amino acid residues between its VL and VH regions. The flexible polypeptide linker sequence may comprise any naturally occurring amino acid. In some embodiments, the flexible polypeptide linker sequence comprises amino acids glycine and serine. In another embodiment, the flexible polypeptide linker sequence comprises sets of glycine and serine repeats such as $(Gly_4Ser)n$, where n is a positive integer equal to or greater than 1. In one embodiment, the flexible polypeptide linkers include, but are not limited to, $(Gly_4Ser)_4$ or $(Gly_4Ser)_3$. Variation in the flexible polypeptide linker length may retain or enhance activity, giving rise to superior efficacy in activity studies.

In one aspect, the present invention contemplates modifications of the starting antibody or fragment (e.g., svFv) amino acid sequence that generate functionally equivalent molecules. For example, the VH or VL of an scFv comprised in the CAR can be modified to retain at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity of the starting VH or VL framework region of the scFv. The present invention also contemplates modifications of the entire CAR construct, e.g., modifications in one or more amino acid sequences of the various domains of the CAR construct in order to generate functionally equivalent molecules. The CAR construct can be modified to retain at least about 70%, 71%. 72%. 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity of the starting CAR construct.

Transmembrane Domain

With respect to the transmembrane domain, in various embodiments, the CAR is designed to comprise a transmembrane domain that is fused to the extracellular domain of the CAR. In one embodiment, the transmembrane domain is one that naturally is associated with one of the domains in the CAR. In some instances, the transmembrane domain can be selected or modified by amino acid substitution to avoid binding of such domains to the transmembrane domains of the same or different surface membrane proteins to minimize interactions with other members of the receptor complex. In another embodiment, the transmembrane domain is capable of homodimerization with another CAR on the CAR T cell surface. In another embodiment, the amino acid sequence of the transmembrane domain may be modified or substituted so as to minimize interactions with the binding domains of the native binding partner present in the same CAR T cell.

A transmembrane domain can include one or more additional amino acids adjacent to the transmembrane region, e.g., one or more amino acid associated with the extracellular region of the protein from which the transmembrane was derived (e.g., 1, 2, 3, 4, 5, 6, 7, 8, 9, 10 up to 15 amino acids of the extracellular region) and/or one or more additional amino acids associated with the intracellular region of the protein from which the transmembrane protein is derived (e.g., 1, 2, 3, 4, 5, 6, 7, 8, 9, 10 up to 15 amino acids of the intracellular region). In one aspect, the transmembrane domain is one that is associated with one of the other domains of the CAR e.g., in one embodiment, the transmembrane domain may be from the same protein that the signaling domain, costimulatory domain or the hinge domain is derived from. In another aspect, the transmembrane domain is not derived from the same protein that any other domain of the CAR is derived from. In some instances, the transmembrane domain can be selected or modified by amino acid substitution to avoid binding of such domains to the transmembrane domains of the same or different surface membrane proteins, e.g., to minimize interactions with other members of the receptor complex. In one aspect, the transmembrane domain is capable of homodimerization with another CAR on the cell surface of a CAR-expressing cell. In a different aspect, the amino acid sequence of the transmembrane domain may be modified or substituted so as to minimize interactions with the binding domains of the native binding partner present in the same CAR-expressing cell.

The transmembrane domain may be derived either from a natural or from a recombinant source. Where the source is natural, the domain may be derived from any membrane-bound or transmembrane protein. In one embodiment, the transmembrane region is capable of signaling to the intracellular domain(s) whenever the CAR has bound to a target. Transmembrane regions of particular use in this invention may be derived from (i.e., comprise at least the transmembrane region(s) of), but not limited to, e.g., regions selected from any one or more of e.g., the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. In some embodiments, a transmembrane domain may include at least the transmembrane region(s) of, e.g., KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), NKp44, NKp30, NKp46, CD160, CD19, IL2R beta, IL2R gamma, IL7R α, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMFI, CD150, IPO-3), BLAME (SLAMF8), SELPLG (CD162), LTBR, PAG/Cbp, NKG2D, or NKG2C.

In some instances, a variety of hinges (aka "spacers") can be employed as well, e.g., including but not limited to the human Ig (immunoglobulin) hinge (e.g., an IgG4 hinge, an IgD hinge), a GS linker (e.g., a GS linker described herein), a KIR2DS2 hinge or a CD8α hinge. In one aspect, the hinge or spacer is the amino acid sequence provided as SEQ ID NO:4. In one aspect, the transmembrane domain is a transmembrane domain from the sequence provided as SEQ ID NO: 12.

In one aspect, the transmembrane domain may be recombinant, in which case it will comprise predominantly hydrophobic residues such as leucine and valine. In one aspect, a triplet of phenylalanine, tryptophan and valine will be found at each end of a recombinant transmembrane domain. Optionally, a short oligo- or polypeptide linker, between 2 and 10 amino acids in length may form the linkage between the transmembrane domain and the cytoplasmic signaling domain of the CAR. A glycine-serine doublet provides a particularly suitable linker, e.g., GGGGSGGGGS (SEQ ID NO: 35). In some embodiments, the linker is encoded by a nucleotide sequence of GGTGGCGGAGGTTCTGGAGGTGGAGGTTCC (SEQ ID NO: 36). Other suitable linkers can be found in Table 2.

In one aspect, the hinge or spacer comprises a KIR2DS2 hinge.

Cytoplasmic Domain

The cytoplasmic domain or intracellular signaling domain of the CAR of the invention is responsible for activation of at least one of the normal effector functions of the immune cell in which the CAR has been placed in. The term "effector function" refers to a specialized function of a cell. The effector function of a T cell, for example, may be cytolytic activity or helper activity, including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Examples of intracellular signaling domains for use in the CAR of the invention include the cytoplasmic sequences of the T cell receptor (TCR) and co-receptors that act in concert to initiate signal transduction following antigen receptor engagement, as well as any derivative or variant of these sequences and any recombinant sequence that has the same functional capability.

It is known that signals generated through the TCR alone are insufficient for full activation of the T cell and that a secondary and/or costimulatory signal is also required. Thus, T cell activation can be said to be mediated by two distinct classes of cytoplasmic signaling sequences: those that initiate antigen-dependent primary activation through the TCR (primary cytoplasmic signaling sequences) and those that act in an antigen-independent manner to provide a secondary or costimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM containing primary intracellular signaling domains that are of particular use in the invention include those of CD3 zeta, common FcR gamma (FCER1G), Fc gamma RIIa, FcR beta (Fc Epsilon R1b), CD3 gamma, CD3 delta, CD3 epsilon, CD79a, CD79b, DAP10, and DAP12. In one embodiment, a CAR of the invention comprises an intracellular signaling domain, e.g., a primary signaling domain of CD3-zeta.

In one aspect, the cytoplasmic domain of the CAR is designed to comprise the CD3-zeta signaling domain by itself or combined with any other desired cytoplasmic domain(s) useful in the context of the CAR of the invention. For example, the cytoplasmic domain of the CAR can comprise a CD3 zeta chain portion and a costimulatory signaling region. The costimulatory signaling region refers to a portion of the CAR comprising the intracellular domain of a costimulatory molecule. A costimulatory molecule is a cell surface molecule other than an antigen receptor or its ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. Further examples of such costimulatory molecules include CDS, ICAM-1, GITR, BAFFR, HVEM (LIGHTR), SLAMF7, NKp80 (KLRF1), NKp44, NKp30, NKp46, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMFI, CD150, IPO-3), BLAME (SLAMF8), SELPLG (CD162), LTBR, LAT, GADS, SLP-76, PAG/Cbp, and a ligand that specifically binds with CD83.

The cytoplasmic signaling sequences within the cytoplasmic signaling portion of the CAR of the invention may be linked to each other in a random or specified order. Optionally, a short oligo- or polypeptide linker, for example, between 2 and 10 amino acids in length may form the linkage. A glycine-serine doublet provides a particularly suitable linker. Exemplary glycine-serine linkers are listed in Table 2, e.g., SEQ ID NOs: 22, 24, 25, 26, or 27.

In one aspect, the cytoplasmic domain is designed to comprise the signaling domain of CD3-zeta and the signaling domain of CD28. In one aspect, the cytoplasmic domain is designed to comprise the signaling domain of CD3-zeta and the signaling domain of 4-1BB. In one aspect, the signaling domain of 4-1BB is a signaling domain set forth in SEQ ID NO: 14. In one aspect, the signaling domain of CD3-zeta is a signaling domain set forth in SEQ ID NO: 18 or SEQ ID NO: 20.

Regulatable Chimeric Antigen Receptors

In some embodiments, a regulatable CAR (RCAR) where the CAR activity can be controlled is desirable to optimize the safety and efficacy of a CAR therapy. An RCAR can be used substituted for a CAR in any of the embodiments described herein.

There are many ways CAR activities can be regulated. For example, inducible apoptosis using, e.g., a caspase fused to a dimerization domain (see, e.g., Di et al., N Engl. J. Med. 2011 Nov. 3; 365(18):1673-1683), can be used as a safety switch in the CAR therapy of the instant invention. In an aspect, a RCAR comprises a set of polypeptides, typically two in the simplest embodiments, in which the components of a standard CAR described herein, e.g., an antigen binding domain and an intracellular signaling domain, are partitioned on separate polypeptides or members. In some embodiments, the set of polypeptides include a dimerization switch that, upon the presence of a dimerization molecule, can couple the polypeptides to one another, e.g., can couple an antigen binding domain to an intracellular signaling domain.

In an aspect, an RCAR comprises two polypeptides or members: 1) an intracellular signaling member comprising an intracellular signaling domain, e.g., a primary intracellular signaling domain described herein, and a first switch domain; 2) an antigen binding member comprising an antigen binding domain, e.g., that targets a tumor antigen, as described herein and a second switch domain. Optionally, the RCAR comprises a transmembrane domain described herein. In an embodiment, a transmembrane domain can be disposed on the intracellular signaling member, on the antigen binding member, or on both. (Unless otherwise indicated, when members or elements of an RCAR are described herein, the order can be as provided, but other orders are included as well. In other words, in an embodiment, the order is as set out in the text, but in other embodiments, the order can be different. E.g., the order of elements on one side of a transmembrane region can be different from the example, e.g., the placement of a switch domain relative to a intracellular signaling domain can be different, e.g., reversed).

In an embodiment, the first and second switch domains can form an intracellular or an extracellular dimerization switch. In an embodiment, the dimerization switch can be a homodimerization switch, e.g., where the first and second switch domain are the same, or a heterodimerization switch, e.g., where the first and second switch domain are different from one another.

In embodiments, an RCAR can comprise a "multi switch." A multi switch can comprise heterodimerization switch domains or homodimerization switch domains. A multi switch comprises a plurality of, e.g., 2, 3, 4, 5, 6, 7, 8, 9, or 10, switch domains, independently, on a first member, e.g., an antigen binding member, and a second member, e.g., an intracellular signaling member. In an embodiment, the first member can comprise a plurality of first switch domains, e.g., FKBP-based switch domains, and the second member can comprise a plurality of second switch domains, e.g., FRB-based switch domains. In an embodiment, the first member can comprise a first and a second switch domain, e.g., a FKBP-based switch domain and a FRB-based switch domain, and the second member can comprise a first and a second switch domain, e.g., a FKBP-based switch domain and a FRB-based switch domain.

In an embodiment, the intracellular signaling member comprises one or more intracellular signaling domains, e.g., a primary intracellular signaling domain and one or more costimulatory signaling domains.

In an embodiment, the antigen binding member may comprise one or more intracellular signaling domains, e.g., one or more costimulatory signaling domains. In an embodiment, the antigen binding member comprises a plurality, e.g., 2 or 3 costimulatory signaling domains described herein, e.g., selected from 41BB, CD28, CD27, ICOS, and OX40, and in embodiments, no primary intracellular signaling domain. In an embodiment, the antigen binding member comprises the following costimulatory signaling domains, from the extracellular to intracellular direction: 41BB-CD27; 41BB-CD27; CD27-41BB; 41BB-CD28; CD28-41BB; OX40-CD28; CD28-OX40; CD28-41BB; or 41BB-CD28. In such embodiments, the intracellular binding member comprises a CD3zeta domain. In one such embodiment the RCAR comprises (1) an antigen binding member comprising, an antigen binding domain, a transmembrane domain, and two costimulatory domains and a first switch domain; and (2) an intracellular signaling domain comprising a transmembrane domain or membrane tethering domain and at least one primary intracellular signaling domain, and a second switch domain.

An embodiment provides RCARs wherein the antigen binding member is not tethered to the surface of the CAR cell. This allows a cell having an intracellular signaling member to be conveniently paired with one or more antigen binding domains, without transforming the cell with a sequence that encodes the antigen binding member. In such embodiments, the RCAR comprises: 1) an intracellular signaling member comprising: a first switch domain, a transmembrane domain, an intracellular signaling domain, e.g., a primary intracellular signaling domain, and a first switch domain; and 2) an antigen binding member comprising: an antigen binding domain, and a second switch domain, wherein the antigen binding member does not comprise a transmembrane domain or membrane tethering domain, and, optionally, does not comprise an intracellular signaling domain. In some embodiments, the RCAR may further comprise 3) a second antigen binding member comprising: a second antigen binding domain, e.g., a second antigen binding domain that binds a different antigen than is bound by the antigen binding domain; and a second switch domain.

Also provided herein are RCARs wherein the antigen binding member comprises bispecific activation and targeting capacity. In this embodiment, the antigen binding member can comprise a plurality, e.g., 2, 3, 4, or 5 antigen binding domains, e.g., scFvs, wherein each antigen binding domain binds to a target antigen, e.g. different antigens or the same antigen, e.g., the same or different epitopes on the same antigen. In an embodiment, the plurality of antigen binding domains are in tandem, and optionally, a linker or hinge region is disposed between each of the antigen binding domains. Suitable linkers and hinge regions are described herein.

An embodiment provides RCARs having a configuration that allows switching of proliferation. In this embodiment, the RCAR comprises: 1) an intracellular signaling member comprising: optionally, a transmembrane domain or membrane tethering domain; one or more co-stimulatory signaling domain, e.g., selected from 41BB, CD28, CD27, ICOS, and OX40, and a switch domain; and 2) an antigen binding member comprising: an antigen binding domain, a transmembrane domain, and a primary intracellular signaling domain, e.g., a CD3zeta domain, wherein the antigen binding member does not comprise a switch domain, or does not comprise a switch domain that dimerizes with a switch domain on the intracellular signaling member. In an embodiment, the antigen binding member does not comprise a co-stimulatory signaling domain. In an embodiment, the intracellular signaling member comprises a switch domain from a homodimerization switch. In an embodiment, the intracellular signaling member comprises a first switch domain of a heterodimerization switch and the RCAR comprises a second intracellular signaling member which comprises a second switch domain of the heterodimerization switch. In such embodiments, the second intracellular signaling member comprises the same intracellular signaling domains as the intracellular signaling member. In an embodiment, the dimerization switch is intracellular. In an embodiment, the dimerization switch is extracellular.

In any of the RCAR configurations described here, the first and second switch domains comprise a FKBP-FRB based switch as described herein.

Also provided herein are cells comprising an RCAR described herein. Any cell that is engineered to express a RCAR can be used as a RCARX cell. In an embodiment the RCARX cell is a T cell, and is referred to as a RCART cell. In an embodiment the RCARX cell is an NK cell, and is referred to as a RCARN cell.

Also provided herein are nucleic acids and vectors comprising RCAR encoding sequences. Sequence encoding various elements of an RCAR can be disposed on the same nucleic acid molecule, e.g., the same plasmid or vector, e.g., viral vector, e.g., lentiviral vector. In an embodiment, (i) sequence encoding an antigen binding member and (ii) sequence encoding an intracellular signaling member, can be present on the same nucleic acid, e.g., vector. Production of the corresponding proteins can be achieved, e.g., by the use of separate promoters, or by the use of a bicistronic transcription product (which can result in the production of two proteins by cleavage of a single translation product or by the translation of two separate protein products). In an embodiment, a sequence encoding a cleavable peptide, e.g., a P2A or F2A sequence, is disposed between (i) and (ii). In an embodiment, a sequence encoding an IRES, e.g., an EMCV or EV71 IRES, is disposed between (i) and (ii). In these embodiments, (i) and (ii) are transcribed as a single RNA. In an embodiment, a first promoter is operably linked to (i) and a second promoter is operably linked to (ii), such that (i) and (ii) are transcribed as separate mRNAs.

Alternatively, the sequence encoding various elements of an RCAR can be disposed on the different nucleic acid molecules, e.g., different plasmids or vectors, e.g., viral vector, e.g., lentiviral vector. E.g., the (i) sequence encoding an antigen binding member can be present on a first nucleic acid, e.g., a first vector, and the (ii) sequence encoding an intracellular signaling member can be present on the second nucleic acid, e.g., the second vector.

Dimerization Switches

Dimerization switches can be non-covalent or covalent. In a non-covalent dimerization switch, the dimerization molecule promotes a non-covalent interaction between the switch domains. In a covalent dimerization switch, the dimerization molecule promotes a covalent interaction between the switch domains.

In an embodiment, the RCAR comprises a FKBP/FRAP, or FKBP/FRB,-based dimerization switch. FKBP12 (FKBP, or FK506 binding protein) is an abundant cytoplasmic protein that serves as the initial intracellular target for the natural product immunosuppressive drug, rapamycin. Rapamycin binds to FKBP and to the large PI3K homolog FRAP (RAFT, mTOR). FRB is a 93 amino acid portion of FRAP, that is sufficient for binding the FKBP-rapamycin complex (Chen, J., Zheng, X. F., Brown, E. J. & Schreiber, S. L. (1995) *Identification of an 11-kDa FKBP12-rapamycin-binding domain within the 289-kDa FKBP12-rapamycin-associated protein and characterization of a critical serine residue*. Proc Natl Acad Sci USA 92: 4947-51.)

In embodiments, an FKBP/FRAP, e.g., an FKBP/FRB, based switch can use a dimerization molecule, e.g., rapamycin or a rapamycin analog.

The amino acid sequence of FKBP is as follows:

(SEQ ID NO: 37)
D V P D Y A S L G G P S S P K K K R K V S R G V Q

V E T I S P G D G R T F P K R G Q T C V V H Y T G

M L E D G K K F D S S R D R N K P F K F M L G K Q

-continued

E V I R G W E E G V A Q M S V G Q R A K L T I S P

D Y A Y G A T G H P G I I P P H A T L V F D V E L

L K L E T S Y

In embodiments, an FKBP switch domain can comprise a fragment of FKBP having the ability to bind with FRB, or a fragment or analog thereof, in the presence of rapamycin or a rapalog, e.g., the underlined portion of SEQ ID NO: 37, which is:

(SEQ ID NO: 38)
V Q V E T I S P G D G R T F P K R G Q T C V V H Y

T G M L E D G K K F D S S R D R N K P F K F M L G

K Q E V I R G W E E G V A Q M S V G Q R A K L T I

S P D Y A Y G A T G H P G I I P P H A T L V F D V

E L L K L E T S

The amino acid sequence of FRB is as follows:

(SEQ ID NO: 39)
ILWHEMWHEG LEEASRLYFG ERNVKGMFEV LEPLHAMMER

GPQTLKETSF NQAYGRDLME AQEWCRKYMK SGNVKDLTQA

WDLYYHVFRR ISK

"FKBP/FRAP, e.g., an FKBP/FRB, based switch" as that term is used herein, refers to a dimerization switch comprising: a first switch domain, which comprises an FKBP fragment or analog thereof having the ability to bind with FRB, or a fragment or analog thereof, in the presence of rapamycin or a rapalog, e.g., RAD001, and has at least 70, 75, 80, 85, 90, 95, 96, 97, 98, or 99% identity with, or differs by no more than 30, 25, 20, 15, 10, 5, 4, 3, 2, or 1 amino acid residues from, the FKBP sequence of SEQ ID NO: 18 or 19; and a second switch domain, which comprises an FRB fragment or analog thereof having the ability to bind with FRB, or a fragment or analog thereof, in the presence of rapamycin or a rapalog, and has at least 70, 75, 80, 85, 90, 95, 96, 97, 98, or 99% identity with, or differs by no more than 30, 25, 20, 15, 10, 5, 4, 3, 2, or 1 amino acid residues from, the FRB sequence of SEQ ID NO: 20. In an embodiment, a RCAR described herein comprises one switch domain comprises amino acid residues disclosed in SEQ ID NO: 37 (or SEQ ID NO: 38), and one switch domain comprises amino acid residues disclosed in SEQ ID NO: 39.

In embodiments, the FKBP/FRB dimerization switch comprises a modified FRB switch domain that exhibits altered, e.g., enhanced, complex formation between an FRB-based switch domain, e.g., the modified FRB switch domain, a FKBP-based switch domain, and the dimerization molecule, e.g., rapamycin or a rapalogue, e.g., RAD001. In an embodiment, the modified FRB switch domain comprises one or more mutations, e.g., 2, 3, 4, 5, 6, 7, 8, 9, 10 or more, selected from mutations at amino acid position(s) L2031, E2032, S2035, R2036, F2039, G2040, T2098, W2101, D2102, Y2105, and F2108, where the wild-type amino acid is mutated to any other naturally-occurring amino acid. In an embodiment, a mutant FRB comprises a mutation at E2032, where E2032 is mutated to phenylalanine (E2032F), methionine (E2032M), arginine (E2032R), valine (E2032V), tyrosine (E2032Y), isoleucine (E2032I), e.g., SEQ ID NO: 40, or leucine (E2032L), e.g., SEQ ID NO: 41. In an embodiment, a mutant FRB comprises a mutation at T2098, where T2098 is mutated to phenylalanine (T2098F) or leucine (T2098L), e.g., SEQ ID NO: 42. In an embodiment, a mutant FRB comprises a mutation at E2032 and at T2098, where E2032 is mutated to any amino acid, and where T2098 is mutated to any amino acid, e.g., SEQ ID NO: 43. In an embodiment, a mutant FRB comprises an E2032I and a T2098L mutation, e.g., SEQ ID NO: 44. In an embodiment, a mutant FRB comprises an E2032L and a T2098L mutation, e.g., SEQ ID NO: 45.

TABLE 1

Exemplary mutant FRB having increased affinity for a dimerization molecule.

| FRB mutant | Amino Acid Sequence | SEQ ID NO: |
|---|---|---|
| E2032I mutant | ILWHEMWHEGLIEASRLYFGERNVKGMF EVLEPLHAMMERGPQTLKETSFNQAYGR DLMEAQEWCRKYMKSGNVKDLTQAWDLY YHVFRRISKTS | 40 |
| E2032L mutant | ILWHEMWHEGLLEASRLYFGERNVKGMF EVLEPLHAMMERGPQTLKETSFNQAYGR DLMEAQEWCRKYMKSGNVKDLTQAWDLY YHVFRRISKTS | 41 |
| T2098L mutant | ILWHEMWHEGLEEASRLYFGERNVKGMF EVLEPLHAMMERGPQTLKETSFNQAYGR DLMEAQEWCRKYMKSGNVKDLLQAWDLY YHVFRRISKTS | 42 |
| E2032, T2098 mutant | ILWHEMWHEGLXEASRLYFGERNVKGMF EVLEPLHAMMERGPQTLKETSFNQAYGR DLMEAQEWCRKYMKSGNVKDLXQAWDLY YHVFRRISKTS | 43 |
| E2032I, T2098L mutant | ILWHEMWHEGLIEASRLYFGERNVKGMF EVLEPLHAMMERGPQTLKETSFNQAYGR DLMEAQEWCRKYMKSGNVKDLLQAWDLY YHVFRRISKTS | 44 |
| E2032L, T2098L mutant | ILWHEMWHEGLLEASRLYFGERNVKGMF EVLEPLHAMMERGPQTLKETSFNQAYGR DLMEAQEWCRKYMKSGNVKDLLQAWDLY YHVFRRISKTS | 45 |

Other suitable dimerization switches include a GyrB-GyrB based dimerization switch, a Gibberellin-based dimerization switch, a tag/binder dimerization switch, and a halo-tag/snap-tag dimerization switch. Following the guidance provided herein, such switches and relevant dimerization molecules will be apparent to one of ordinary skill.

Dimerization Molecule

Association between the switch domains is promoted by the dimerization molecule. In the presence of dimerization molecule interaction or association between switch domains allows for signal transduction between a polypeptide associated with, e.g., fused to, a first switch domain, and a polypeptide associated with, e.g., fused to, a second switch domain. In the presence of non-limiting levels of dimerization molecule signal transduction is increased by 1.1, 1.2, 1.3, 1.4, 1.5, 1.6, 1.7, 1.8, 1.9, 2, 5, 10, 50, 100 fold, e.g., as measured in a system described herein.

Rapamycin and rapamycin analogs (sometimes referred to as rapalogues), e.g., RAD001, can be used as dimerization molecules in a FKBP/FRB-based dimerization switch described herein. In an embodiment the dimerization molecule can be selected from rapamycin (sirolimus), RAD001 (everolimus), zotarolimus, temsirolimus, AP-23573

(ridaforolimus), biolimus, simapimo, XL765, AP21967, and analogs or derivatives thereof.

Enhancers of T Cell Priming (ETPs)

The present invention also provides nucleic acids, e.g., DNA or RNA constructs, encoding ETPs for co-delivery with nucleic acids, e.g., DNA or RNA constructs, encoding CARs. The ETPs of the invention enhance the CAR-expressing T cell's antigen presentation and T cell priming activities, leading to enhanced anti-disease effects. In the context of cancer, without being bound by theory, it is believed that co-delivery of ETP, e.g., ETP DNAs or ETP RNAs, with CAR, e.g., CAR RNA or CAR ETP into a T cell enhances anti-tumor activity by increasing the ability of the T cell to function as antigen presenting cells and prime T cells, in addition to the CAR-mediated cell killing ability. This allows for T cell-mediated priming of non-engineered tumor-reactive T cells, which can persist as tumor suppressors once CAR expression by adoptive ETP-CAR T cells, e.g., RNA ETP-CAR T cells, has subsided, creating a transient therapy with permanent anti-cancer effects, e.g., anti-tumor effects.

In one embodiment, the ETP is a costimulatory molecule. Exemplary costimulatory molecules include, but are not limited to, CD70, CD83, CD80, CD86, CD40, CD154, CD137L (4-1BBL), CD252 (OX40L), CD275 (ICOS-L), CD54 (ICAM-1), CD49a, CD43, CD48, CD112 (PVRL2), CD150 (SLAM), CD155 (PVR), CD265 (RANK), CD270 (HVEM), TL1A, CD127, IL-4R, GITR-L, CD160, CD258, TIM-4, CD153 (CD30L), CD200R (OX2R), CD44, ligands thereof, and functional fragments and variants thereof.

In an embodiment, the ETP comprises an amino acid sequence of CD70 (e.g., GenBank Acc. No. NP_001243.1), or a nucleic acid sequence of CD70 (e.g., GenBank Acc. No. NM_001252.4). In an embodiment, the ETP comprises an amino acid sequence of CD83 (e.g., GenBank Acc. No. AAH30830.1), or a nucleic acid sequence of CD83 (e.g., GenBank Acc. No. BC030830.1). In an embodiment, the ETP comprises an amino acid sequence of CD80 (e.g., GenBank Acc. No. AAH42665.1), or a nucleic acid sequence of CD80 (e.g., GenBank Acc. No. BC042655.1). In an embodiment, the ETP comprises an amino acid sequence of CD86 (e.g., GenBank Acc. No. AAB03814.1), or a nucleic acid sequence of CD86 (e.g., GenBank Acc. No. U04343.1). In an embodiment, the ETP comprises an amino acid sequence of CD40 (e.g., GenBank Acc. No. AAH64518.1, or AAH12419.1), or a nucleic acid sequence of CD40 (e.g., GenBank Acc. No. BC064518.1 or BC012419.1). In an embodiment, the ETP comprises an amino acid sequence of CD154 (e.g., GenBank Acc. No. NP_000065.1 or AAH74950.1), or a nucleic acid sequence of CD154 (e.g., GenBank Acc. No. NM_000074.2 or BC074950.2). In an embodiment, the ETP comprises an amino acid sequence of CD137L (4-1BBL) (e.g., GenBank Acc. No. NP_003802.1), or a nucleic acid sequence of CD137L (4-1BBL) (e.g., GenBank Acc. No. NM_003811.3). In an embodiment, the ETP comprises an amino acid sequence of CD252 (OX40L) (e.g., GenBank Acc. No. AAH41663.1), or a nucleic acid sequence of CD252 (OX40L) (e.g., GenBank Acc. No. BC041663.1). In an embodiment, the ETP comprises an amino acid sequence of CD275 (ICOSL) (e.g., GenBank Acc. No. AAH20674.1), or a nucleic acid sequence of CD275 (ICOSL) (e.g., GenBank Acc. No. BC020674.1). In an embodiment, the ETP comprises an amino acid sequence of CD54 (ICAM-1) (e.g., GenBank Acc. No. AAP35500.1 or CAA41977.1), or a nucleic acid sequence of CD54 (ICAM-1) (e.g., GenBank Acc. No. BT006854.1 or X59286.1). In an embodiment, the ETP comprises an amino acid sequence of CD49a (e.g., GenBank Acc. No. AAI37123.1), or a nucleic acid sequence of CD49a (e.g., GenBank Acc. No. BC137122.1). In an embodiment, the ETP comprises an amino acid sequence of CD43 (e.g., GenBank Acc. No. NP_001025459.1 or AAB20910.1), or a nucleic acid sequence of CD43 (e.g., GenBank Acc. No. NM_001030288.2 or AAB20910.1). In an embodiment, the ETP comprises an amino acid sequence of CD48 (e.g., GenBank Acc. No. CAG33293.1), or a nucleic acid sequence of CD48 (e.g., GenBank Acc. No. CR457012.1). In an embodiment, the ETP comprises an amino acid sequence of CD112 (PVRL2) (e.g., GenBank Acc. No. CAG33099.1), or a nucleic acid sequence of CD 112 (PVRL2) (e.g., GenBank Acc. No. CR456818.1). In an embodiment, the ETP comprises an amino acid sequence of CD150 (SLAM) (e.g., GenBank Acc. No. NP_003028.1), or a nucleic acid sequence of CD150 (SLAM) (e.g., GenBank Acc. No. NM_003037.3). In an embodiment, the ETP comprises an amino acid sequence of CD155 (PVR) (e.g., GenBank Acc. No. NP_006496.4), or a nucleic acid sequence of CD155 (PVR) (e.g., GenBank Acc. No. NM_006505.4). In an embodiment, the ETP comprises an amino acid sequence of CD265 (RANK) (e.g., GenBank Acc. No. Q9Y6Q6.1), or a nucleic acid sequence of CD265 (RANK) (e.g., GenBank Acc. No. AF018253.1). In an embodiment, the ETP comprises an amino acid sequence of CD270 (HVEM) (e.g., GenBank Acc. No. CAG33190.1 or AAH29848.1), or a nucleic acid sequence of CD270 (HVEM) (e.g., GenBank Acc. No. CR456909.1 or BC029848.1). In an embodiment, the ETP comprises an amino acid sequence of TL1A (e.g., GenBank Acc. No. AAI04464.1), or a nucleic acid sequence of TL1A (e.g., GenBank Acc. No. BC104463.1). In an embodiment, the ETP comprises an amino acid sequence of CD127 (e.g., GenBank Acc. No. AAH69999.1), or a nucleic acid sequence of CD127 (e.g., GenBank Acc. No. BC069999.1). In an embodiment, the ETP comprises an amino acid sequence of GITR-L (e.g., GenBank Acc. No. AAQ89227.1), or a nucleic acid sequence of GITR-L (e.g., GenBank Acc. No. AY358868.1). In an embodiment, the ETP comprises an amino acid sequence of CD160 (e.g., GenBank Acc. No. CAG46665.1), or a nucleic acid sequence of CD160 (e.g., GenBank Acc. No. CR541867.1). In an embodiment, the ETP comprises an amino acid sequence of CD258 (e.g., GenBank Acc. No. NP_742011.2), or a nucleic acid sequence of CD258 (e.g., GenBank Acc. No. NM_172014.2). In an embodiment, the ETP comprises an amino acid sequence of TIM-4 (e.g., GenBank Acc. No. AF066594.1), or a nucleic acid sequence of TIM-4 (e.g., GenBank Acc. No. JX049980.1). In an embodiment, the ETP comprises an amino acid sequence of CD153 (CD30L) (e.g., GenBank Acc. No. AAI11940.1), or a nucleic acid sequence of CD153 (CD30L) (e.g., GenBank Acc. No. BC111939.1). In an embodiment, the ETP comprises an amino acid sequence of CD200R (OX2R) (e.g., GenBank Acc. No. AAI43394.1), or a nucleic acid sequence of CD200R (OX2R) (e.g., GenBank Acc. No. BC143393.1). In an embodiment, the ETP comprises an amino acid sequence of CD44 (e.g., GenBank Acc. No. ACI46596.1), or a nucleic acid sequence of CD44 (e.g., GenBank Acc. No. FJ21664.1).

In another embodiment, the ETP is a soluble cytokine. Exemplary soluble cytokines include, but are not limited to, IL-2, IL-12, IL-6, IL-7, IL-15, IL-18, IL-21, GM-CSF, IL-18, IL-21, and IL-27, and functional fragments and variants thereof.

In an embodiment, the ETP comprises an amino acid sequence of interleukin 2 (IL-2) (e.g., GenBank Acc. No. AAB46833.1), or a nucleic acid sequence of IL-2 (e.g., GenBank Acc. No. 582692.1). In an embodiment, the ETP comprises an amino acid sequence of interleukin 12 (IL-12) (e.g., GenBank Acc. No. AAD16432.1), or a nucleic acid sequence of IL-12 (e.g., GenBank Acc. No. AF101062.1). In an embodiment, the ETP comprises an amino acid sequence of interleukin 6 (IL-6) (e.g., GenBank Acc. No. AAD13886.1 or NP_000591.1), or a nucleic acid sequence of IL-6 (e.g., GenBank Acc. No. 556892.1 or NM_000600.3). In an embodiment, the ETP comprises an amino acid sequence of interleukin 7 (IL-7) (e.g., GenBank Acc. No. AAH47698.1 or NP_000871.1), or a nucleic acid sequence of IL-7 (e.g., GenBank Acc. No. BC047698.1 or NM_000880.3). In an embodiment, the ETP comprises an amino acid sequence of interleukin 15 (IL-15) (e.g., GenBank Acc. No. AAU21241.1), or a nucleic acid sequence of IL-15 (e.g., GenBank Acc. No. AY720442.1). In an embodiment, the ETP comprises an amino acid sequence of interleukin 18 (IL-18) (e.g., GenBank Acc. No. AAK95950.1), or a nucleic acid sequence of IL-18 (e.g., GenBank Acc. No. AY044641.1). In an embodiment, the ETP comprises an amino acid sequence of interleukin 21 (IL-21) (e.g., GenBank Acc. No. AAG29348.1), or a nucleic acid sequence of IL-21 (e.g., GenBank Acc. No. AF254069.1). In an embodiment, the ETP comprises an amino acid sequence of GM-CSF (e.g., GenBank Acc. No. AAA52578.1), or a nucleic acid sequence of GM-CSF (e.g., GenBank Acc. No. M11220.1).

In another embodiment, the ETP is a polypeptide involved in antigen presentation. Exemplary polypeptides involved in antigen presentation include, but are not limited to, CD64, MHC I, and MHC II, and functional fragments and variants thereof.

In an embodiment, the ETP comprises an amino acid sequence of CD64 (e.g., GenBank Acc. No. AAI52384.1), or a nucleic acid sequence of CD64 (e.g., GenBank Acc. No. BC152383.1). In an embodiment, the ETP comprises an amino acid sequence of MHCI (e.g., GenBank Acc. No. AAH40479.1), or a nucleic acid sequence of MHCI (e.g., GenBank Acc. No. BC040479.1).

In another embodiment, the ETP is a polypeptide involved in trafficking and/or migration. Exemplary polypeptides involved in trafficking and/or migration include, but are not limited to, CD183, CCR2, CCR6, CD50, CD197, CD58, and CD62L, and functional fragments and variants thereof.

In an embodiment, the ETP comprises an amino acid sequence of CD183 (e.g., GenBank Acc. No. AAH34403.1), or a nucleic acid sequence of CD183 (e.g., GenBank Acc. No. BC034403.1). In an embodiment, the ETP comprises an amino acid sequence of CCR2 (e.g., GenBank Acc. No. AAH95540.1), or a nucleic acid sequence of CCR2 (e.g., GenBank Acc. No. BC095540.1). In an embodiment, the ETP comprises an amino acid sequence of CCR6 (e.g., GenBank Acc. No. NP_113597.2), or a nucleic acid sequence of CCR6 (e.g., GenBank Acc. No. NM_031409.3). In an embodiment, the ETP comprises an amino acid sequence of CD50 (e.g., GenBank Acc. No. AAH58903.1), or a nucleic acid sequence of CD50 (e.g., GenBank Acc. No. BC058903.1). In an embodiment, the ETP comprises an amino acid sequence of CD197 (e.g., GenBank Acc. No. NP_001829.1), or a nucleic acid sequence of CD197 (e.g., GenBank Acc. No. NM_001838.3). In an embodiment, the ETP comprises an amino acid sequence of CD58 (e.g., GenBank Acc. No. CAG33220.1), or a nucleic acid sequence of CD58 (e.g., GenBank Acc. No. CR456939.1). In an embodiment, the ETP comprises an amino acid sequence of CD62L (e.g., GenBank Acc. No. AAH20758.1), or a nucleic acid sequence of CD62L (e.g., GenBank Acc. No. BC020758.1).

In another embodiment, the ETP is a polypeptide involved in dendritic cell targeting. Exemplary polypeptides involved in dendritic cell targeting include TLR ligands, anti-DEC-205 antibody, and anti-DC-SIGN antibody, and functional fragments and variants thereof.

In another embodiment, more than 1, such as 2, 3, 4, 5, 6 or more ETPs are co-delivered with a nucleic acid sequence encoding a CAR, e.g., a CAR RNA, into a T cell. In one aspect, the co-delivery of 1 or more ETPs does not affect, e.g., substantially decrease or substantitally inhibit, the expression or activity of the co-delivered or co-expressed CAR in the ETP-CAR T cell, e.g., RNA ETP-CAR T cell. In another aspect, the co-delivery of a CAR does not affect, e.g., substantially decrease or substantially inhibit, the expression or activity of the co-delivered or co-expressed ETP or ETPs.

Candidate molecules (i.e., candidate ETPs) can be tested for T cell priming activity alone or in conjunction with a CAR using assays described in the Examples.

In embodiments, an ETP comprises an amino acid sequence with at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to, or which differs by no more than 30, 25, 20, 15, 10 or 5 amino acid residues from, an ETP described herein, or a functional fragment thereof, or a naturally occurring ETP, e.g., a naturally occurring ETP described herein, e.g., at least 80%, at least 85%, at least 90%, at least 91%, at least 92%, at least 93%, at least 94%, at least 95%, at least 96%, at least 97%, at least 98%, or at least 99% identity to an ETP described herein, or a functional fragment thereof.

Percent identity in the context of two or more nucleic acids or polypeptide sequences, refers to two or more sequences that are the same. Two sequences are "substantially identical" if two sequences have a specified percentage of amino acid residues or nucleotides that are the same (i.e., 60% identity, optionally 70%, 71%, 72%. 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. Methods of alignment of sequences for comparison are well known in the art. Optimal alignment of sequences for comparison can be conducted, e.g., by the local homology algorithm of Smith and Waterman, (1970) Adv. Appl. Math. 2:482c, by the homology alignment algorithm of Needleman and Wunsch, (1970) J. Mol. Biol. 48:443, by the search for similarity method of Pearson and Lipman, (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Brent et al., (2003) Current Protocols in Molecular Biology).

Two examples of algorithms that are suitable for determining percent sequence identity and sequence similarity are the BLAST and BLAST 2.0 algorithms, which are described in Altschul et al., (1977) Nuc. Acids Res. 25:3389-3402; and Altschul et al., (1990) J. Mol. Biol. 215:403-410, respectively. Software for performing BLAST analyses is publicly available through the National Center for Biotechnology Information.

The percent identity between two amino acid sequences can also be determined using the algorithm of E. Meyers and W. Miller, (1988) Comput. Appl. Biosci. 4:11-17) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (1970) J. Mol. Biol. 48:444-453) algorithm which has been incorporated into the GAP program in the GCG software package (available at www.gcg.com), using either a Blossom 62 matrix or a PAM250 matrix, and a gap weight of 16, 14, 12, 10, 8, 6, or 4 and a length weight of 1, 2, 3, 4, 5, or 6.

Functional variants of an ETP provided herein may comprise one or more mutations, such that the variant retains some level of T cell priming activity of the ETP described herein. In an embodiment, the functional variant has at least 10%, at least 20%, at least 30%, at least 40%, at least 50%, at least 60%, at least 70%, at least 75%, at least 80%, at least 85%, at least 90%, at least 95%, or at least 99% (e.g., at least 80%, at least 85%, at least 90%, at least 95%, or at least 99%) of the T cell priming activity as the corresponding naturally occurring or parental ETP. In embodiments, the functional variant has at least 200%, at least 300%, at least 400%, at least 500%, at least 1000% or more of the T cell priming activity as the corresponding naturally occurring or parental ETP. The mutations present in a functional variant include amino acid substitutions, additions, and deletions. Mutations can be introduced by standard techniques known in the art, such as site-directed mutagenesis and PCR-mediated mutagenesis. The mutation may be a conservative amino acid substitution, in which the amino acid residue is replaced with an amino acid residue having a similar side chain.

In an embodiment, the ETP comprises a functional fragment of a naturally occurring ETP, e.g., an ETP disclosed herein. In an embodiment, the functional fragment comprises at least 5, 10, 15, 20, 25, 30, 35, 40, 45, 50, 55, 60, 65, 70, 75, 80, 85, 90, or 95% of the amino acid residues of the naturally occurring ETP. For example, the ETP comprises a domain or a functional fragment of a domain of an ETP disclosed herein, that comprises T cell priming activity.

Nucleic Acids

Disclosed herein are methods for producing the CARs and ETPs of the invention. In one embodiment, the nucleic acid encoding the CAR and/or ETP to be introduced into a T cell is a DNA molecule (e.g., a cDNA molecule). In another embodiment, the nucleic acid encoding the CAR and/or ETP to be introduced into a T cell is an RNA molecule. In another embodiment, the RNA is generated by in vitro transcription. In one embodiment, the RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA.

RNA Constructs

Disclosed herein are methods for expressing an RNA encoding a CAR and/or an RNA encoding an ETP. The present invention also includes a CAR encoding RNA construct and/or an ETP encoding RNA construct that can be directly transfected into a cell. A method for generating mRNA for use in transfection can involve in vitro transcription (IVT) of a template with specially designed primers, followed by polyA addition, to produce a construct containing 3' and 5' untranslated sequence ("UTR"), a 5' cap and/or Internal Ribosome Entry Site (IRES), the nucleic acid to be expressed, and a polyA tail, typically 50-2000 bases in length (SEQ ID NO:46). RNA so produced can efficiently transfect different kinds of cells. In one aspect, the template includes sequences for the CAR and/or the ETP.

In one embodiment, the in vitro transcribed RNA CAR and/or RNA ETP can be introduced to a cell as a form of transient transfection. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired template for in vitro transcription is a CAR or ETP described herein. For example, the template for the RNA CAR comprises an extracellular region comprising a single chain variable domain of an antibody to a tumor associated antigen described herein; a hinge region (e.g., a hinge region described herein), a transmembrane domain (e.g., a transmembrane domain described herein such as a transmembrane domain of CD8a); and a cytoplasmic region that includes an intracellular signaling domain, e.g., an intracellular signaling domain described herein, e.g., comprising the signaling domain of CD3-zeta and the signaling domain of 4-1BB.

In one embodiment, the template for in vitro transcription is the CAR of the present invention. For example, the template for the RNA CAR comprises an extracellular domain comprising a single chain variable domain of an antibody of interest (e.g., an anti-tumor antibody); a transmembrane domain (e.g., from the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154); and one or more intracellular signaling domains (e.g., 4-1BB, CD3-zeta).

In one embodiment, the template for in vitro transcription is a ETP. For example, the template for ETP comprises the nucleic acid sequence encoding a costimulatory molecule (e.g., CD70, CD83, CD80, CD86, CD40, CD154, CD137L (4-1BBL), CD252 (OX40L), CD275 (ICOS-L), CD54 (ICAM-1), CD49a, CD43, CD48, CD112 (PVRL2), CD150 (SLAM), CD155 (PVR), CD265 (RANK), CD270 (HVEM), TL1A, CD127, IL-4R, GITR-L, CD160, CD258, TIM-4, CD153 (CD30L), CD200R (OX2R), CD44, ligands thereof, or functional fragments or variants thereof), a soluble cytokine (e.g., IL-2, IL-12, IL-6, IL-7, IL-15, IL-18, IL-21, GM-CSF, IL-18, IL-21, IL-27), a polypeptide involved in antigen presentation (e.g., CD64, MHC I, MHC II), a polypeptide involved in trafficking and/or migration (e.g., CD183, CCR2, CCR6, CD50, CD197, CD58, CD62L), or a polypeptide involved in dendritic cell targeting (e.g., TLR ligands, anti-DEC-205 antibody, anti-DC-SIGN antibody).

In one embodiment, the DNA to be used for PCR contains an open reading frame. The DNA can be from a naturally occurring DNA sequence from the genome of an organism. In one embodiment, the DNA is a full length gene of interest of a portion of a gene. The gene can include some or all of the 5' and/or 3' untranslated regions (UTRs). The gene can include exons and introns. In one embodiment, the DNA to be used for PCR is a human gene. In another embodiment, the DNA to be used for PCR is a human gene including the 5' and 3' UTRs. The DNA can alternatively be an artificial DNA sequence that is not normally expressed in a naturally occurring organism. An exemplary artificial DNA sequence is one that contains portions of genes that are ligated together to form an open reading frame that encodes a fusion protein. The portions of DNA that are ligated together can be from a single organism or from more than one organism.

Genes that can be used as sources of DNA for PCR include genes that encode polypeptides that provide a therapeutic or prophylactic effect to an organism or that can be used to diagnose a disease or disorder in an organism. Preferred genes are genes which are useful for a short term treatment, or where there are safety concerns regarding dosage or the expressed gene. For example, for treatment of cancer, autoimmune disorders, parasitic, viral, bacterial, fungal or other infections, the transgene(s) to be expressed may encode a polypeptide that functions as a ligand or receptor for cells of the immune system, or can function to stimulate or inhibit the immune system of an organism. It is not desirable to have prolonged ongoing stimulation of the immune system, nor necessary to produce changes which last after successful treatment, since this may then elicit a new problem. For treatment of an autoimmune disorder, it may be desirable to inhibit or suppress the immune system during a flare-up, but not long term, which could result in the patient becoming overly sensitive to an infection.

PCR is used to generate a template for in vitro transcription of mRNA which is used for transfection. Methods for performing PCR are well known in the art. Primers for use in PCR are designed to have regions that are substantially complementary to regions of the DNA to be used as a template for the PCR. Any DNA polymerase useful for PCR can be used in the methods disclosed herein. The reagents and polymerase are commercially available from a number of sources.

Chemical structures with the ability to promote stability and/or translation efficiency may also be used. The RNA preferably has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one preferred embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In one embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270: 1485-65 (2003).

PolyA/T stretches can be integrated into a DNA template (e.g., a plasmid) by molecular cloning. Alternatively, the polyA/T segment of the transcriptional DNA template can be produced during PCR by using a reverse primer containing a polyT tail, such as 100T tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as *E. coli* polyA polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps on also provide stability to RNA molecules. In a preferred embodiment, RNAs produced by the methods disclosed herein include a 5' cap. The 5' cap is provided using techniques known in the art and described herein (Cougot, et al, Trends in Biochem. Sci., 29:436-444 (2001); Stepinski, et al, RNA, 7: 1468-95 (2001); Elango, et al, Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

In one embodiment, the present invention includes synthetic RNA and RNA-like analogs encoding the CARs and ETPs of the invention. That is, the present invention includes CAR-and ETP-encoding RNA and RNA-like constructs manufactured in any method known in the art, including, for example IVT RNA and synthesized RNA. In one embodiment, RNA is synthesized through known methods of oligonucleotide synthesis. Methods of oligonucleotide synthesis include, for example, H-phosphonate synthesis, phosphodiester synthesis, phosphotriester synthesis, phosphite triester synthesis, and the phosphoramidite method. In some instances, synthesis of the RNA construct includes the incorporation of nucleotide/nucleoside derivatives or analogs. As such, in one embodiment, the RNA of the invention comprises a nucleotide/nucleoside derivative or analog. For example, one type of analog is LNA, such as beta-D-oxy-LNA, alpha-L-oxy-LNA, beta-D-amino-LNA and beta-D-thio-LNA, and beta-D-oxy-LNA. Methods of producing synthesized RNA are well known in the art, described, for example, in U.S. Pat. Nos. 8,242,248, 6,111,095, U.S. Patent Application Publication No.: 2010/0324278, U.S. Patent Application Publication No.: 2010/0137010, and PCT International Publication No.: WO 2007/031081, each of which is incorporated by reference. Further, the present invention includes CAR- and ETP-encoding RNA and RNA-like constructs manufactured via methods heretofore unknown, provided that the constructs comprise a sequence which encodes the components of the CAR or ETP described herein.

RNA or DNA can be introduced into target cells using any of a number of different methods, for instance, commercially available methods which include, but are not limited to, electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany), cationic liposome mediated transfection using lipofection, polymer encapsulation, peptide mediated transfection, or biolistic particle delivery systems such as "gene guns" (see, for example, Nishikawa, et al. Hum Gene Ther., 12(8):861-70 (2001).

DNA Constructs

Disclosed herein are methods for expressing a DNA or a cDNA encoding a CAR and/or a DNA or a cDNA encoding an ETP. The present invention also provides vectors in which a DNA of the present invention is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

In another embodiment, the vector comprising the nucleic acid encoding the desired CAR of the invention is an adenoviral vector (A5/35). In another embodiment, the expression of nucleic acids encoding CARs can be accomplished using of transposons such as sleeping beauty, crisper, CAS9, and zinc finger nucleases. See below June et al. 2009 Nature Reviews Immunology 9.10: 704-716, is incorporated herein by reference.

In brief summary, the expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The expression constructs of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al., 2012, MOLECULAR CLONING: A LABORATORY MANUAL, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, retrovirus vectors are used. In some embodiments, adenovirus vectors are used. A number of adenovirus vectors are known in the art. In one embodiment, lentivirus vectors are used.

Additional promoter elements, e.g., enhancers, regulate the frequency of transcriptional initiation. Typically, these are located in the region 30-110 bp upstream of the start site, although a number of promoters have been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription. Exemplary promoters include the CMV IE gene, EF-1α, ubiquitin C, or phosphoglycerokinase (PGK) promoters.

Engineered T Cells ("ETP-CAR T Cells")

Provided herein are T cells comprising one or more, e.g., one, two, or more, nucleic acid molecules comprising a nucleic acid sequence encoding a CAR described herein and a nucleic acid sequence encoding an ETP described herein. In an embodiment, the nucleic acid comprises both the nucleic acid sequence encoding a CAR described herein and the nucleic acid sequence encoding an ETP described herein, e.g., the nucleic acid sequences comprising the CAR and the ETP are disposed on the same nucleic acid molecule. In an embodiment, the nucleic acid comprises two nucleic acid molecules, wherein the nucleic acid sequence encoding a CAR described herein is disposed on one nucleic acid molecule and the nucleic acid sequence encoding an ETP described herein is disposed on the other nucleic acid molecule. In an embodiment, the nucleic acid molecule comprises RNA. In an embodiment, the nucleic acid comprises DNA. In embodiments where the nucleic acid sequences encoding the CAR and ETP are disposed on two nucleic acid molecules, both nucleic acid molecules comprise RNA or both nucleic acid molecules comprise DNA. Alternatively, in embodiments where the nucleic acid sequences encoding the CAR and ETP are disposed on two nucleic acid molecules, one nucleic acid molecule comprises RNA and the other nucleic acid molecule comprises DNA.

In some embodiments, one or both of the nucleic acid sequences encoding a CAR and the nucleic acid sequences encoding an ETP comprise RNA. For example, the nucleic acid sequence encoding the CAR can comprise RNA and the nucleic acid sequence encoding the ETP can comprise DNA. In another example, the nucleic acid sequence encoding the CAR can comprise DNA and the nucleic acid sequence encoding the ETP can comprise RNA.

In some embodiments where the nucleic acid sequence encoding a CAR comprises DNA, e.g., a vector, e.g., a viral vector, the CAR comprises an extracellular domain, e.g., an antigen binding domain described herein, a transmembrane domain, and two or more intracellular signaling domains, e.g., a primary signaling domain and a costimulatory signaling domain. In an embodiment, the CAR comprises a primary signaling domain, e.g., a CD3 zeta domain as described herein, and a costimulatory signaling domain, e.g., a 4-1BB domain as described herein. In such embodiments, the CAR comprises one or more additional intracellular signaling domains, e.g., 1, 2, 3, 4, or 5 additional costimulatory signaling domains as described herein. In any of the foregoing embodiments, the CAR may be a regulatable CAR, e.g., an RCAR described herein, in which the CAR activity can be controlled, e.g., by administering or withdrawing the dimerization molecule. In such embodiments where an RCAR is used, the CAR activity may be transient, while the antigen presenting or T cell priming activity is prolonged, and results in a more long lasting immune response against the disease.

In embodiments, the T cell comprises a nucleic acid sequence encoding a CAR described herein and two or more, e.g., 2, 3, 4, 5, 6, 7, 8, 9 or 10 or more nucleic acid sequences encoding an ETP, wherein the nucleic acid sequences encode different ETPs described herein. In such embodiments where the T cell comprises more than one nucleic acid sequence encoding an ETP described herein, each nucleic acid sequence encoding the ETPs can be present on the same nucleic acid molecule or on different nucleic acid molecules. Two or more nucleic acid sequences encoding ETPs, e.g., 2, 3, 4, 5, 6, 7, 8, 9 or 10 or more, can be disposed on the same nucleic acid molecule. By way of example, in an embodiment where the T cell comprises three nucleic acid sequences encoding ETPs, two of the nucleic acid sequences encoding ETPs can be disposed on one nucleic acid molecule, and one nucleic acid sequence encoding an ETP can be disposed on another nucleic acid molecule. In any of these embodiments, the nucleic acid sequence encoding a CAR described herein can be disposed on a nucleic acid molecule further comprising one or more nucleic acid sequences encoding an ETP. In an alternative embodiment, the nucleic acid sequence encoding a CAR described herein is disposed on a nucleic acid molecule that does not comprise a nucleic acid sequence encoding an ETP.

Also provided herein are methods for generating a T cell comprising a nucleic acid sequence encoding a CAR and a nucleic acid sequence encoding an ETP. In embodiments where one or both of the nucleic acid sequences encoding a CAR and ETP comprise RNA, the RNA molecule(s) are transfected, e.g., electroporated, into the T cell using standard transfection methods and reagents known in the art. In embodiments where one or both of the nucleic acid sequences encoding a CAR and ETP comprise DNA, the DNA molecule(s) can be introduced, e.g., by transfection, electroporation, viral transduction, into the T cell using standard methods and reagents known in the art.

The in vitro transcribed CAR mRNA and ETP mRNA, cDNAs, or vectors, e.g., retroviral or lentiviral vectors, encoding the CAR and ETP of interest, can be delivered into different types of lymphocytes (e.g., T cells), as well as into tissues and whole organisms using transfected cells as carriers or cell-free local or systemic delivery of encapsulated, bound or naked nucleic acid molecules, e.g., in vitro transcribed RNA, mRNA, cDNA, or DNA vectors. The method used can be for any purpose where transient expression is required or sufficient. T cells that have been modified to express a nucleic acid sequence encoding CAR and a nucleic acid sequence encoding an ETP are referred to as "ETP-CAR T cells". T cells can be transduced, e.g., virally transduced, with CAR DNA, e.g., a vector encoding a CAR, and ETP DNA, e.g., a vector encoding an ETP. T cells co-transfected with CAR RNA and ETP RNA are referred to as "RNA ETP-CAR T cells."

The disclosed methods can be applied to modulation of cell activity in basic research and therapy, in the fields of cancer, stem cells, acute and chronic infections, and autoimmune diseases, including modulation of the developmental pathways.

The methods also provide the ability to control the level of expression over a wide range by changing the amount of input RNA, making it possible to individually regulate the expression level of each transfected gene. Furthermore, the PCR-based technique of mRNA production greatly facilitates the design of the chimeric receptor mRNAs with different structures and combination of their domains. For example, varying of different intracellular effector/costimulator domains on multiple chimeric receptors in the same cell allows determination of the structure of the receptor combinations which assess the highest level of cytotoxicity against multi-antigenic targets, and at the same time lowest cytotoxicity toward normal cells.

An advantage of the methods of the invention is that RNA transfection is essentially transient and a vector-free. Moreover, RNA transfection of multiple distinct RNAs can be performed with high efficiency without substantially altering the expression of the distinct polypeptides encoded by co-delivered RNA molecules. An RNA transgene can be delivered to a lymphocyte and expressed therein following a brief in vitro cell activation, as a minimal expressing cassette without the need for any additional viral sequences. Under these conditions, integration of the transgene into the host cell genome is unlikely. Cloning of cells is not necessary because of the high efficiency of transfection of the RNA and its ability to uniformly modify the entire lymphocyte population. Thus, cells containing an RNA construct introduced according to the disclosed method can be used therapeutically. For example, a lymphocyte cell population is withdrawn from a patient, transfected with different RNA constructs, and then reintroduced into the patient. The transfected cell population then can target, e.g., cancer cells or cells containing other disease-associated antigens. A benefit of the use of RNA transfected cells is that the RNA transgene has a limited half-life. The encoded protein will only be produced by the transfected cell for a limited period of time. This serves to reduce the risk of any unintended consequences when genetically modified cells are introduced into a patient.

In a preferred embodiment, the technology is used for personalized therapy. For example, for treatment of tumors, the patient's blood or cells is collected by an appropriate method such as apheresis, biopsy or venapuncture. The cells are cultured for at least 24 hours during which time the cells are modified with an appropriate nucleic acid, e.g., transfected with an appropriate RNA construct or transduced with an appropriate DNA, e.g., vector, construct, to treat the tumor. The cells can be stored frozen before transfection or tranduction, if necessary. They are then returned back to the patient at the appropriate time and in the appropriate dose. In one embodiment, modified cells, e.g., RNA-modified cells or DNA-modified cells, are administered to the patient multiple times.

Immune therapy with in vitro-transcribed RNA (IVT-RNA) makes use of two different strategies both of which have been successively tested in various animal models. Cells are transfected with in vitro-transcribed RNA by means of lipofection or electroporation and administered to the subject. Preferably, it is desirable to stabilize IVT-RNA using various modifications in order to achieve prolonged expression of transferred IVT-RNA.

Some IVT vectors are known in the literature which are utilized in a standardized manner as template for in vitro transcription and which have been genetically modified in such a way that stabilized RNA transcripts are produced. Currently protocols used in the art are based on a plasmid vector with the following structure: a 5' RNA polymerase promoter enabling RNA transcription, followed by a gene of interest which is flanked either 3' and/or 5' by untranslated regions (UTR), and a 3' polyadenyl cassette containing a chain of A nucleotides. Prior to in vitro transcription, the circular plasmid is linearized downstream of the polyadenyl cassette by type II restriction enzymes (recognition sequence corresponds to cleavage site). The polyadenyl cassette thus corresponds to the later poly(A) sequence in the transcript. As a result of this procedure, some nucleotides remain as part of the enzyme cleavage site after linearization and extend or mask the poly(A) sequence at the 3' end. It is not clear, whether this nonphysiological overhang affects the amount of protein produced intracellularly from such a construct.

RNA has several advantages over more traditional plasmid or viral approaches. Gene expression from an RNA source does not require transcription and the protein product is produced rapidly after the transfection. Further, the RNA needs only to gain access to the cytoplasm, rather than the nucleus, and therefore typical transfection methods result in an extremely high rate of transfection. In addition, plasmid based approaches require that the promoter driving the expression of the gene of interest be active in the cells under study.

In another embodiment, the RNAs of the invention can be delivered into the cells by electroporation. See, e.g., the formulations and methodology of electroporation of nucleic acid constructs into mammalian cells as taught in US 2004/0014645, US 2005/0052630A1, US 2005/0070841 A 1, US 2004/0059285A1, US 2004/0092907A1. The various parameters including electric field strength required for electroporation of any known cell type are generally known in the relevant research literature as well as numerous patents and applications in the field. See e.g., U.S. Pat. Nos. 6,678,556, 7,171,264, and 7,173,116. Apparatus for therapeutic application of electroporation are available commercially, e.g., the MedPulser™ DNA Electroporation Therapy System (Inovio/Genetronics, San Diego, Calif.), and are described in patents such as U.S. Pat. Nos. 6,567,694; 6,516,223, 5,993,434, 6,181,964, 6,241,701, and 6,233,482; electroporation may also be used for transfection of cells in vitro as described e.g. in US20070128708A1. Electroporation may also be utilized to deliver nucleic acids into cells in vitro. Accordingly, electroporation-mediated administration into cells of nucleic acids including expression constructs utilizing any of the many available devices and electroporation systems known to those of skill in the art presents an exciting new means for delivering an RNA of interest to a target cell.

In other embodiments, the RNAs can be delivered into the cells by calcium phosphate precipitation, lipofection, particle bombardment, microinjection, and the like. Methods for producing cells comprising vectors and/or exogenous nucleic acids are well-known in the art. See, for example, Sambrook et al., 2012, MOLECULAR CLONING: A LABORATORY MANUAL, volumes 1-4, Cold Spring Harbor Press, NY).

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). Other methods of state-of-the-art targeted delivery of nucleic acids are available, such as delivery of polynucleotides with targeted nanoparticles.

The use of lipid formulations is contemplated for the introduction of the RNAs into a host cell (in vitro, ex vivo or in vivo). In another aspect, the RNA may be associated with a lipid. The RNA associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid/RNA associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, NY); cholesterol ("Choi") can be obtained from Calbiochem-Behring; dimyristyl phosphatidylglycerol ("DMPG") and other lipids may be obtained from Avanti Polar Lipids, Inc. (Birmingham, AL.). Stock solutions of lipids in chloroform or chloroform/methanol can be stored at about −200 C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Sources of Cells

Prior to expansion and genetic modification or other modification, a source of cells, e.g., T cells, can be obtained from a subject. The term "subject" is intended to include living organisms in which an immune response can be elicited (e.g., mammals). Examples of subjects include humans, monkeys, chimpanzees, dogs, cats, mice, rats, and transgenic species thereof. T cells can be obtained from a number of sources, including peripheral blood mononuclear cells, bone marrow, lymph node tissue, cord blood, thymus tissue, tissue from a site of infection, ascites, pleural effusion, spleen tissue, and tumors.

In certain aspects of the present disclosure, immune effector cells, e.g., T cells, can be obtained from a unit of blood collected from a subject using any number of techniques known to the skilled artisan, such as Ficoll™ separation. In one preferred aspect, cells from the circulating blood of an individual are obtained by apheresis. The apheresis product typically contains lymphocytes, including T cells, monocytes, granulocytes, B cells, other nucleated white blood cells, red blood cells, and platelets. In one aspect, the cells collected by apheresis may be washed to remove the plasma fraction and, optionally, to place the cells in an appropriate buffer or media for subsequent processing steps. In one embodiment, the cells are washed with phosphate buffered saline (PBS). In an alternative embodiment, the wash solution lacks calcium and may lack magnesium or may lack many if not all divalent cations.

Initial activation steps in the absence of calcium can lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca-free, Mg-free PBS, PlasmaLyte A, or other saline solution with or without buffer. Alternatively, the undesirable components of the apheresis sample may be removed and the cells directly resuspended in culture media.

In one aspect, T cells are isolated from peripheral blood lymphocytes by lysing the red blood cells and depleting the monocytes, for example, by centrifugation through a PERCOLL™ gradient or by counterflow centrifugal elutriation.

The methods described herein can include, e.g., selection of a specific subpopulation of immune effector cells, e.g., T cells, that are a T regulatory cell-depleted population, CD25+ depleted cells, using, e.g., a negative selection technique, e.g., described herein. Preferably, the population of T regulatory depleted cells contains less than 30%, 25%, 20%, 15%, 10%, 5%, 4%, 3%, 2%, 1% of CD25+ cells.

In one embodiment, T regulatory cells, e.g., CD25+ T cells, are removed from the population using an anti-C25 antibody, or fragment thereof, or a CD25-binding ligand, IL-2. In one embodiment, the anti-CD25 antibody, or fragment thereof, or CD25-binding ligand is conjugated to a substrate, e.g., a bead, or is otherwise coated on a substrate, e.g., a bead. In one embodiment, the anti-CD25 antibody, or fragment thereof, is conjugated to a substrate as described herein.

In one embodiment, the T regulatory cells, e.g., CD25+ T cells, are removed from the population using CD25 depletion reagent from Militenyi™. In one embodiment, the ratio of cells to CD25 depletion reagent is 1e7 cells to 20 uL, or 1e7 cells to 15 uL, or 1e7 cells to 10 uL, or 1e7 cells to 5 uL, or 1e7 cells to 2.5 uL, or 1e7 cells to 1.25 uL.

In one embodiment, the population of immune effector cells to be depleted includes about $6\times10^9$ CD25+ T cells. In other aspects, the population of immune effector cells to be depleted include about $1\times10^9$ to $1\times10^{10}$ CD25+ T cell, and any integer value in between. In one embodiment, the resulting population T regulatory depleted cells has $2\times10^9$ T regulatory cells, e.g., CD25+ cells, or less (e.g., $1\times10^9$, $5\times10^8$, $1\times10^8$, $5\times10^7$, $1\times10^7$, or less CD25+ cells).

In one embodiment, the T regulatory cells, e.g., CD25+ cells, are removed from the population using the CliniMAC system with a depletion tubing set, such as, e.g., tubing 162-01. In one embodiment, the CliniMAC system is run on a depletion setting such as, e.g., DEPLETION2.1.

The methods described herein can include more than one selection step, e.g., more than one depletion step. Enrichment of a T cell population by negative selection can be accomplished, e.g., with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail can include antibodies to CD14, CD20, CD11b, CD16, HLA-DR, and CD8.

The methods described herein can further include removing cells from the population which express a tumor antigen, e.g., a tumor antigen that does not comprise CD25, e.g., CD19, CD30, CD38, CD123, CD20, CD14 or CD11b, to thereby provide a population of T regulatory depleted, e.g., CD25+ depleted, and tumor antigen depleted cells that are suitable for expression of a CAR, e.g., a CAR described herein. In one embodiment, tumor antigen expressing cells are removed simultaneously with the T regulatory, e.g., CD25+ cells. For example, an anti-C25 antibody, or fragment thereof, and an anti-tumor antigen antibody, or fragment thereof, can be attached to the same substrate, e.g., bead, which can be used to remove the cells or an anti-CD25 antibody, or fragment thereof, or the anti-tumor antigen antibody, or fragment thereof, can be attached to separate beads, a mixture of which can be used to remove the cells. In other embodiments, the removal of T regulatory cells, e.g., CD25+ cells, and the removal of the tumor antigen expressing cells is sequential, and can occur, e.g., in either order.

Also provided are methods that include removing cells from the population which express a check point inhibitor, e.g., a check point inhibitor described herein, e.g., one or more of PD1+ cells, LAG3+ cells, and TIM3+ cells, to thereby provide a population of T regulatory depleted, e.g., CD25+ depleted cells, and check point inhibitor depleted cells, e.g., PD1+, LAG3+ and/or TIM3+ depleted cells. Exemplary check point inhibitors include B7-H1, B&-1, CD160, P1H, 2B4, PD1, TIM3, CEACAM (e.g., CEACAM-1, CEACAM-3 and/or CEACAM-5), LAG3, TIGIT, CTLA-4, BTLA and LAIR1. In one embodiment, check point inhibitor expressing cells are removed simultaneously with the T regulatory, e.g., CD25+ cells. For example, an anti-C25 antibody, or fragment thereof, and an anti-check point inhibitor antibody, or fragment thereof, can be attached to the same bead which can be used to remove the cells, or an anti-CD25 antibody, or fragment thereof, and the anti-check point inhibitor antibody, or fragment there, can be attached to separate beads, a mixture of which can be used to remove the cells. In other embodiments, the removal of T regulatory cells, e.g., CD25+ cells, and the removal of the check point inhibitor expressing cells is sequential, and can occur, e.g., in either order.

Methods described herein can include a positive selection step. For example, T cells can isolated by incubation with anti-CD3/anti-CD28 (e.g., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another embodiment, the time period is 10 to 24 hours, e.g., 24 hours. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points.

In one embodiment, a T cell population can be selected that expresses one or more of IFN-γ, TNFα, IL-17A, IL-2, IL-3, IL-4, GM-CSF, IL-10, IL-13, granzyme B, and perforin, or other appropriate molecules, e.g., other cytokines. Methods for screening for cell expression can be determined, e.g., by the methods described in PCT Publication No.: WO 2013/126712.

For isolation of a desired population of cells by positive or negative selection, the concentration of cells and surface (e.g., particles such as beads) can be varied. In certain aspects, it may be desirable to significantly decrease the volume in which beads and cells are mixed together (e.g., increase the concentration of cells), to ensure maximum contact of cells and beads. For example, in one aspect, a concentration of 10 billion cells/ml, 9 billion/ml, 8 billion/ml, 7 billion/ml, 6 billion/ml, or 5 billion/ml is used. In one aspect, a concentration of 1 billion cells/ml is used. In yet one aspect, a concentration of cells from 75, 80, 85, 90, 95, or 100 million cells/ml is used. In further aspects, concentrations of 125 or 150 million cells/ml can be used.

Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (e.g., leukemic blood, tumor tissue, etc.). Such populations of cells may have therapeutic value and would be desirable to obtain. For example, using high concentration of cells allows more efficient selection of CD8+ T cells that normally have weaker CD28 expression.

In a related aspect, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In one aspect, the concentration of cells used is $5\times10^6$/ml. In other aspects, the concentration used can be from about $1\times10^5$/ml to $1\times10^6$/ml, and any integer value in between.

In other aspects, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain aspects, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in immune effector cell therapy for any number of diseases or conditions that would benefit from immune effector cell therapy, such as those described herein. In one aspect a blood sample or an apheresis is taken from a generally healthy subject. In certain aspects, a blood sample or an apheresis is taken from a generally healthy subject who is at risk of developing a disease, but who has not yet developed a disease, and the cells of interest are isolated and frozen for later use. In certain aspects, the T cells may be expanded, frozen, and used at a later time. In certain aspects, samples are collected from a patient shortly after diagnosis of a particular disease as described herein but prior to any treatments. In a further aspect, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation.

In a further aspect of the present invention, T cells are obtained from a patient directly following treatment that leaves the subject with functional T cells. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain aspects, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

In one embodiment, the immune effector cells expressing a CAR molecule, e.g., a CAR molecule described herein, are obtained from a subject that has received a low, immune enhancing dose of an mTOR inhibitor. In an embodiment, the population of immune effector cells, e.g., T cells, to be engineered to express a CAR, are harvested after a sufficient time, or after sufficient dosing of the low, immune enhancing, dose of an mTOR inhibitor, such that the level of PD1 negative immune effector cells, e.g., T cells, or the ratio of PD1 negative immune effector cells, e.g., T cells/PD1 positive immune effector cells, e.g., T cells, in the subject or harvested from the subject has been, at least transiently, increased.

In other embodiments, population of immune effector cells, e.g., T cells, which have, or will be engineered to express a CAR, can be treated ex vivo by contact with an amount of an mTOR inhibitor that increases the number of PD1 negative immune effector cells, e.g., T cells or increases the ratio of PD1 negative immune effector cells, e.g., T cells/PD1 positive immune effector cells, e.g., T cells.

In one embodiment, a T cell population is diaglycerol kinase (DGK)-deficient. DGK-deficient cells include cells that do not express DGK RNA or protein, or have reduced or inhibited DGK activity. DGK-deficient cells can be generated by genetic approaches, e.g., administering RNA-interfering agents, e.g., siRNA, shRNA, miRNA, to reduce or prevent DGK expression. Alternatively, DGK-deficient cells can be generated by treatment with DGK inhibitors described herein.

In one embodiment, a T cell population is Ikaros-deficient. Ikaros-deficient cells include cells that do not express Ikaros RNA or protein, or have reduced or inhibited Ikaros activity, Ikaros-deficient cells can be generated by genetic approaches, e.g., administering RNA-interfering agents, e.g., siRNA, shRNA, miRNA, to reduce or prevent Ikaros expression. Alternatively, Ikaros-deficient cells can be generated by treatment with Ikaros inhibitors, e.g., lenalidomide.

In embodiments, a T cell population is DGK-deficient and Ikaros-deficient, e.g., does not express DGK and Ikaros, or has reduced or inhibited DGK and Ikaros activity. Such DGK and Ikaros-deficient cells can be generated by any of the methods described herein.

In an embodiment, the NK cells are obtained from the subject. In another embodiment, the NK cells are an NK cell line, e.g., NK-92 cell line (Conkwest).

Activation and Expansion of T Cells

Immune effector cells such as T cells may be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, a population of immune effector cells may be expanded by contact with a surface having attached thereto an agent that stimulates a CD3/TCR complex associated signal and a ligand that stimulates a costimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For costimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody. Examples of an anti-CD28 antibody include 9.3, B-T3, XR-CD28 (Diaclone, Besançon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol Meth. 227(1-2):53-63, 1999).

In certain aspects, the primary stimulatory signal and the costimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one aspect, the agent providing the costimulatory signal is bound to a cell surface and the agent providing the primary activation signal is in solution or coupled to a surface. In certain aspects, both agents can be in solution. In one aspect, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one aspect, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the costimulatory signal is an anti-CD28 antibody or antigen-binding fragment thereof; and both agents are co-immobilized to the same bead in equivalent molecular amounts. In one aspect, a 1:1 ratio of each antibody bound to the beads for CD4+ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular aspect an increase of from about 1 to about 3 fold is observed as compared to the expansion observed using a ratio of 1:1. In one aspect, the ratio of CD3:CD28 antibody bound to the beads ranges from 100:1 to 1:100 and all integer values there between. In one aspect, more anti-CD28 antibody is bound to the particles than anti-CD3 antibody, i.e., the ratio of CD3:CD28 is less than one. In certain aspects, the ratio of anti CD28 antibody to anti CD3 antibody bound to the beads is greater than 2:1. In one particular aspect, a 1:100 CD3:CD28 ratio of antibody bound to beads is used. In one aspect, a 1:75 CD3:CD28 ratio of antibody bound to beads is used. In a further aspect, a 1:50 CD3:CD28 ratio of antibody bound to beads is used. In one aspect, a 1:30 CD3:CD28 ratio of antibody bound to beads is used. In one preferred aspect, a 1:10 CD3:CD28 ratio of antibody bound to beads is used. In one aspect, a 1:3 CD3:CD28 ratio of antibody bound to the beads is used. In yet one aspect, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain aspects the ratio of cells to particles ranges from 1:100 to 100:1 and any integer values in-between and in further aspects the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one aspect, a ratio of particles to cells of 1:1 or less is used. In one particular aspect, a preferred particle:cell ratio is 1:5. In further aspects, the ratio of particles to cells can be varied depending on the day of stimulation. For example, in one aspect, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular aspect, the ratio of particles to cells is 1:1 on the first day of stimulation and adjusted to 1:5 on the third and fifth days of stimulation. In one aspect, particles are added on a daily or every other day basis to a final ratio of 1:1 on the first day, and 1:5 on the third and fifth days of stimulation. In one aspect, the ratio of particles to cells is 2:1 on the first day of stimulation and adjusted to 1:10 on the third and fifth days of stimulation. In one aspect, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type. In one aspect, the most typical ratios for use are in the neighborhood of 1:1, 2:1 and 3:1 on the first day.

In further aspects, the cells, such as T cells, are combined with agent-coated beads, the beads and the cells are subsequently separated, and then the cells are cultured. In an alternative aspect, prior to culture, the agent-coated beads and cells are not separated but are cultured together. In a further aspect, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one aspect the cells (for example, $10^4$ to $10^9$ T cells) and beads (for example, DYNABEADS® M-450 CD3/CD28 T paramagnetic beads at a ratio of 1:1) are combined in a buffer, for example PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain aspects, it may be desirable to significantly decrease the volume in which particles and cells are mixed together (i.e., increase the concentration of cells), to ensure maximum contact of cells and particles. For example, in one aspect, a concentration of about 2 billion cells/ml is used. In one aspect, greater than 100 million cells/ml is used. In a further aspect, a concentration of cells of 10, 15, 20, 25, 30, 35, 40, 45, or 50 million cells/ml is used. In yet one aspect, a concentration of cells from 75, 80, 85, 90, 95, or 100 million cells/ml is used. In further aspects, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain aspects. For example, using high concentration of cells allows more efficient selection of CD8+ T cells that normally have weaker CD28 expression.

In one embodiment, cells transduced with a nucleic acid encoding a CAR, e.g., a CAR described herein, are expanded, e.g., by a method described herein. In one embodiment, the cells are expanded in culture for a period of several hours (e.g., about 2, 3, 4, 5, 6, 7, 8, 9, 10, 15, 18, 21 hours) to about 14 days (e.g., 1, 2, 3, 4, 5, 6, 7, 8, 9, 10, 11, 12, 13 or 14 days). In one embodiment, the cells are expanded for a period of 4 to 9 days. In one embodiment, the cells are expanded for a period of 8 days or less, e.g., 7, 6 or 5 days. In one embodiment, the cells, e.g., a CD19 CAR cell described herein, are expanded in culture for 5 days, and the resulting cells are more potent than the same cells expanded in culture for 9 days under the same culture conditions. Potency can be defined, e.g., by various T cell functions, e.g. proliferation, target cell killing, cytokine production, activation, migration, or combinations thereof. In one embodiment, the cells, e.g., a CD19 CAR cell described herein, expanded for 5 days show at least a one, two, three or four fold increase in cells doublings upon antigen stimulation as compared to the same cells expanded in culture for 9 days under the same culture conditions. In one embodiment, the cells, e.g., the cells expressing a CD19 CAR described herein, are expanded in culture for 5 days, and the resulting cells exhibit higher proinflammatory cytokine production, e.g., IFN-γ and/or GM-CSF levels, as compared to the same cells expanded in culture for 9 days under the same culture conditions. In one embodiment, the cells, e.g., a CD19 CAR cell described herein, expanded for 5 days show at least a one, two, three, four, five, ten fold or more increase in pg/ml of proinflammatory cytokine production, e.g., IFN-γ and/or GM-CSF levels, as compared to the same cells expanded in culture for 9 days under the same culture conditions.

Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

In one embodiment, the cells are expanded in an appropriate media (e.g., media described herein) that includes one or more interleukin that result in at least a 200-fold (e.g., 200-fold, 250-fold, 300-fold, 350-fold) increase in cells over a 14 day expansion period, e.g., as measured by a method described herein such as flow cytometry. In one embodiment, the cells are expanded in the presence IL-15 and/or IL-7 (e.g., IL-15 and IL-7).

T cells that have been exposed to varied stimulation times may exhibit different characteristics. For example, typical blood or apheresed peripheral blood mononuclear cell products have a helper T cell population (TH, CD4+) that is greater than the cytotoxic or suppressor T cell population (TC, CD8+). Ex vivo expansion of T cells by stimulating CD3 and CD28 receptors produces a population of T cells that prior to about days 8-9 consists predominately of TH cells, while after about days 8-9, the population of T cells comprises an increasingly greater population of TC cells. Accordingly, depending on the purpose of treatment, infusing a subject with a T cell population comprising predominately of TH cells may be advantageous. Similarly, if an antigen-specific subset of TC cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Assays

Once a CAR is constructed, various assays can be used to evaluate the activity of the molecule, such as but not limited to, the ability to expand T cells following antigen stimulation, sustain T cell expansion in the absence of re-stimulation, and anti-cancer activities in appropriate animal models. Assays to evaluate the effects of a CAR are described in further detail below.

Western blot analysis of CAR expression in primary T cells can be used to detect the presence of monomers and dimers. See, e.g., Milone et al., Molecular Therapy 17(8): 1453-1464 (2009). Very briefly, T cells (1:1 mixture of $CD4^+$ and $CD8^+$ T cells) expressing the CARs are expanded in vitro for more than 10 days followed by lysis and SDS-PAGE under reducing conditions. CARs containing the full length TCR-ζ cytoplasmic domain and the endogenous TCR-ζ chain are detected by western blotting using an antibody to the TCR-ζ chain. The same T cell subsets are used for SDS-PAGE analysis under non-reducing conditions to permit evaluation of covalent dimer formation.

In vitro expansion of $CAR^+$ T cells following antigen stimulation can be measured by flow cytometry. For example, a mixture of $CD4^+$ and $CD8^+$ T cells are stimulated with αCD3/αCD28 aAPCs followed by transduction with lentiviral vectors expressing GFP under the control of the promoters to be analyzed. Exemplary promoters include the CMV IE gene, EF-1α, ubiquitin C, or phosphoglycerokinase (PGK) promoters. GFP fluorescence is evaluated on day 6 of culture in the $CD4^+$ and/or $CD8^+$ T cell subsets by flow cytometry. See, e.g., Milone et al., Molecular Therapy 17(8): 1453-1464 (2009).

Sustained $CAR^+$ T cell expansion in the absence of re-stimulation can also be measured. See, e.g., Milone et al., Molecular Therapy 17(8): 1453-1464 (2009). Briefly, mean T cell volume (fl) is measured on day 8 of culture using a Coulter Multisizer III particle counter following stimulation with αCD3/αCD28 coated magnetic beads on day 0, and transduction with the indicated CAR on day 1.

Assessment of cell proliferation and cytokine production can be performed as previously described in, e.g., Milone et al., Molecular Therapy 17(8): 1453-1464 (2009).

Cytotoxicity can be assessed by a standard 51Cr-release assay. See, e.g., Milone et al., Molecular Therapy 17(8):

1453-1464 (2009), or by standard degranulation assays, as described in Example 5. For example, RNA CAR T cells co-expressing a CAR and one or more costimulatory molecules are incubated with target cells expressing the antigen targeted by the CAR. By way of example, a mesothelin-targeting CAR expressing T cells which also express one or more co-stimulatory molecules are incubated with mesothelin-expressing target cells (K-meso, SKOV3) and mesothelin-negative cells (K562) and evaluated for CD107a exposure in a degranulation assay.

Candidate ETPs can be tested for the ability to enhance T cell priming using the modified in vitro priming system described in Examples 2 and 3. Briefly, each candidate ETP is co-delivered with a CAR into T cells and exposed to one round of antigen stimulation with, e.g., a tumor antigen such as MART-1. An exemplary method is provided in the examples below.

Other assays, including those described in the Example section herein as well as those that are known in the art can also be used to evaluate the CAR constructs of the invention.

Therapeutic Applications

The present invention provides a variety of therapeutic methods using T cells which are genetically modified to express a chimeric antigen receptor (CAR) and one or more ETPs, e.g., ETP-CAR T cells. In an embodiment, the T cells are genetically modified to transiently express an RNA encoding CAR and an RNA encoding ETP, e.g., RNA ETP-CAR T cells. This is achieved by infusing the ETP-CAR T cells, e.g., RNA ETP-CAR T cells, in to a recipient in need thereof. The infused cell is able to kill cells which express the antigen to which the antigen-binding portion of the CAR binds. In certain embodiments, the antigen is a tumor antigen, and the T cell is administered to a recipient with cancer. The anti-tumor response elicited by the ETP-CAR T cell, e.g., RNA ETP-CAR T cell, involves both CAR-mediated cell killing, as well as ETP-enhanced cytotoxic T lymphocyte priming with tumor-specific antigenic peptides derived from, e.g., the tumor cells killed by CAR activity. Expression of RNA CAR and RNA ETP results in a transient therapy (due to transient expression of the CAR and ETPs) with permanent anti-tumor effects (due to persistence of RNA ETP-CAR T cell priming of tumor-reactive T cells). In particular embodiments, the CAR and ETP RNAs in the RNA ETP-CAR T cells administered to the patient, or their progeny, persist in the patient for 4, 5, 6, 7, 8, 9, 10, 11, 12, 13, 14, 15 days after transduction after administration of the RNA ETP-CAR T cell to the patient.

Accordingly, in one embodiment, the invention provides a method for inhibiting the proliferation or reducing a cell population expressing a disease-associated antigen by contacting a population of cells expressing the disease-associated antigen with an RNA ETP-CAR T cell of the invention that binds to the disease-associated antigen. In one embodiment, the cells are cancer cells. In other embodiments, the ETP-CAR T cell, e.g., RNA ETP-CAR T cell, reduces the quantity, number, amount or percentage of cells and/or cancer cells by at least 25%, at least 30%, at least 40%, at least 50%, at least 65%, at least 75%, at least 85%, at least 95%, or at least 99% in a subject with cancer or an animal model of cancer relative to a negative control. In another embodiment, the subject is a human.

The efficacy of the ETP-CAR T cells, e.g., RNA ETP-CAR T cells, of the invention can be tested using art-recognized animal models for the particular indication of interest. For example, in the context of cancer, established cancer mouse models are widely available for the particular cancer of interest.

In another embodiment, the invention provides methods for preventing, treating and/or managing a disorder associated with cells expressing a disease-associated antigen by administering to a subject in need an ETP-CAR T cell, e.g., RNA ETP-CAR T cell, of the invention that binds to the disease-associated antigen-expressing cell. In one embodiment, the subject is a human.

In another embodiment, the invention provides methods for preventing relapse of cancer associated with cells expressing a particular tumor antigen by administering to a subject in need thereof an ETP-CAR T cell, e.g., RNA ETP-CAR T cell, of the invention that binds to the tumor antigen-expressing cell. In another embodiment, the methods comprise administering to the subject in need thereof an effective amount of an ETP-CAR T cell, e.g., RNA ETP-CAR T cell, of the invention that binds to the disease-associated antigen-expressing cell in combination with an effective amount of another therapy.

In another embodiment, the invention provides a method of inhibiting growth of a cell expressing a tumor antigen by contacting the tumor cell with an ETP-CAR T cell, e.g., RNA ETP-CAR T cell, of the present invention such that the ETP-CAR T cell is activated in response to the antigen and targets the cancer cell, wherein the growth of the tumor is inhibited. In one embodiment, the activated ETP-CAR T cell, e.g., RNA ETP-CAR T cell, targets and kills the cancer cell and/or enhances epitope spreading.

In another embodiment, the invention provides a method of treating a proliferative disease (e.g., cancer) by administering to a subject an ETP-CAR T cell, e.g., RNA ETP-CAR T cell, of the present invention, such that the cancer is treated in the subject. Non-limiting examples of a cancer that can be treated by the present invention include brain cancer, bladder cancer, breast cancer, cervical cancer, colorectal cancer, liver cancer, kidney cancer, lymphoma, leukemia, lung cancer, melanoma, metastatic melanoma, mesothelioma, neuroblastoma, ovarian cancer, prostate cancer, pancreatic cancer, renal cancer, skin cancer, thymoma, sarcoma, non-Hodgkin's lymphoma, Hodgkin's lymphoma, uterine cancer, and combinations thereof.

In another embodiment, the invention provides a method of treating a precancerous condition by administering to a subject an ETP-CAR T cell, e.g., RNA ETP-CAR T cell, of the invention, such that the precancerous condition is treated in the subject.

In another embodiment, the invention provides a method of treating a non-cancer indication by administering to a subject an ETP-CAR T cell, e.g., RNA ETP-CAR T cell, of the present invention such that the non-cancer indication is treated in the subject. Non-limiting examples of non-cancer indications include inflammatory disorders, autoimmune disorders, parasitic, viral, bacterial, fungal or other infections.

In a particular embodiment, the fully-human ETP-CAR T cells of the invention are a vaccine for ex vivo immunization and/or in vivo therapy in a mammal (e.g., a human). For ex vivo immunization, at least one of the following preferably occurs in vitro prior to administering the cell into a mammal: i) expansion of the cells, ii) introducing a nucleic acid encoding a CAR and an ETP, as described herein, to the cells or iii) cryopreservation of the cells. In another embodiment, the invention provides a method for vaccinating a subject comprising administering to the subject an ETP-CAR T cell described herein, e.g., RNA ETP-CAR T cell, of the present invention. E.g., the subject is vaccinated for a cancer, a viral infection, or a bacterial infection. In an embodiment, the method further comprises administering to the subject an antigen, e.g., a tumor antigen, a viral antigen, or a bacterial antigen. Vaccination of a subject can be determined by detecting the capability of the subject to mount an immune response to the particular disease, e.g., by measuring antibody titer against a disease-associated antigen, e.g., a tumor antigen, a viral antigen, or a bacterial antigen.

Ex vivo procedures are well known in the art and are discussed more fully below. Briefly, cells are isolated from a mammal (e.g., a human) and genetically modified (i.e., transduced or transfected in vitro) with a vector expressing a CAR disclosed herein. The CAR-modified cell can be administered to a mammalian recipient to provide a therapeutic benefit. The mammalian recipient may be a human and the CAR-modified cell can be autologous with respect to the recipient. Alternatively, the cells can be allogeneic, syngeneic or xenogeneic with respect to the recipient.

Procedures for ex vivo expansion of hematopoietic stem and progenitor cells are described, for example, in U.S. Pat. No. 5,199,942, incorporated herein by reference, can be applied to the cells of the present invention. Other suitable methods are known in the art therefore the present invention is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to providing a cell-based vaccine for ex vivo immunization, the present invention also provides compositions and methods for in vivo immunization to elicit an immune response directed against an antigen in a patient.

Generally, the cells activated and expanded as described herein may be utilized in the treatment and prevention of diseases that arise in individuals who are immunocompromised. In certain aspects, the cells of the invention are used in the treatment of patients at risk for developing diseases, disorders and conditions associated with the expression of a disease-associated antigen. Thus, the present invention provides methods for the treatment or prevention of diseases, disorders and conditions associated with expression of a disease-associated antigen comprising administering to a subject in need thereof, a therapeutically effective amount of the ETP-CAR T cells of the invention, e.g., RNA ETP-CAR T cell, which bind cells expressing the disease-associated antigen.

The ETP-CAR T cells of the present invention, e.g., RNA ETP-CAR T cell, may be administered either alone, or as a pharmaceutical composition in combination with diluents and/or with other components such as IL-2 or other cytokines or cell populations.

Pharmaceutical Compositions

Pharmaceutical compositions of the present invention comprise an ETP-CAR T cell, e.g., RNA ETP-CAR T cell, as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are in one aspect formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount," "an anti-tumor effective amount," "a tumor-inhibiting effective amount," or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, in some instances $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain instances, it may be desired to administer activated T cells to a subject and then subsequently redraw blood (or have an apheresis performed), activate T cells therefrom according to the present invention, and reinfuse the patient with these activated and expanded T cells. This process can be carried out multiple times every few weeks. In certain aspects, T cells can be activated from blood draws of from 10 cc to 400 cc. In certain aspects, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocol, may select out certain populations of T cells.

Administration of the compositions may be carried out in any convenient manner, including by aerosol inhalation, injection, ingestion, transfusion, implantation or transplantation. The compositions may be administered to a patient trans arterially, subcutaneously, intradermally, intratumorally, intranodally, intramedullary, intramuscularly, by intravenous (i.v.) injection, or intraperitoneally. In one embodiment, the compositions are administered to a patient by intradermal or subcutaneous injection. In one embodiment, the compositions are administered by i.v. injection. In one embodiment, the compositions are injected directly into a tumor, lymph node, or site of infection.

In one embodiment, cells activated and expanded using the methods described herein, or other methods known in the art where T cells are expanded to therapeutic levels, are administered to a patient in conjunction with (e.g., before, simultaneously or following) any number of relevant treatment modalities including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further aspects, the T cells of the invention may be used in a treatment regimen in combination with chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludarabine, cyclosporin, FK506, rapamycin, mycophenolic acid, steroids, FR901228, cytokines, and irradiation. Drugs that inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993) can also be used. In a further aspect, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In one aspect, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

In a particular embodiment, subjects undergo leukapheresis, wherein leukocytes are collected, enriched, or depleted ex vivo to select and/or isolate the cells of interest, e.g., T cells. These T cell isolates may be expanded by methods known in the art and treated such that one or more CAR and ETP constructs of the invention may be introduced, thereby creating an ETP-CAR T cell of the invention, e.g., RNA ETP-CAR T cell. Subjects in need thereof may subsequently undergo standard treatment with high dose chemotherapy followed by peripheral blood stem cell transplantation. In certain aspects, following or concurrent with the transplant, subjects receive an infusion of the expanded ETP-CAR T cells of the present invention, e.g., RNA ETP-CAR T cell. In an additional aspect, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples specifically point out various aspects of the present invention, and are not to be construed as limiting in any way the remainder of the disclosure.

EXAMPLES

Example 1: General Materials and Methods

The following general materials and methods are used in the experiments and examples described herein.

Cell Culture

Primary PBMs, purified CD4+ T cells, and purified CD8+ T cells were from normal healthy HLA-A2+ donors and purchased from University of Pennsylvania Perelman School of Medicine Human Immunology Core, Philadelphia, PA. K562 and SKOV3 cells were from ATCC (Manassas, VA) and K-meso cells were from the Laboratory of C. June (Philadelphia, PA). K562 cells were derived from a chronic myeloid leukemia (NY-ESO-1-CD19−), SKOV3 from an adenocarcinoma, and K-meso cells were K562 cells transduced to express mesothelin. All cells were quantified and sized using a Multisizer 3 COULTER COUNTER (MS3; Beckman Coulter, Brea, CA).

DCs were cultured from PBMCs which were washed twice with Dulbecco's Phosphate Buffered Saline (PBS; Gibco® Life Technologies (LTI), Grand Island, NY), resuspended in AIM-V® Medium (AIM-V; LTI), and then incubated in a plastic tissue-culture treated flask (Corning, Tewksbury, MA) for 2 h at 37° C. in a 5% CO2 incubator. Non-adherent (PBLs) cells were separated from adherent (monocytes) cells by first swirling the medium in the flask until the non-adherent cells collected together, transferring the supernatant containing the non-adherent cells to a separate container, and then washing the adherent cells twice with PBS to remove remaining non-adherent cells. Non-adherent PBLs were then frozen for later use as effectors in the modified in vitro priming assay. Briefly, freshly isolated PBLs were washed twice with PBS, resuspended in AIM-V medium containing 40% Fetal Bovine Serum (FBS; HyClone® Thermo Fisher Scientific, Logan, UT) and 10% Dimehyl Sulphoxide (DMSO) Hybri-Max® (DMSO; Sigma-Aldrich, St. Louis, MO), frozen in a rate-controlled container to −80° C., and then transferred to liquid nitrogen for storage.

Immature DCs were cultured from adherent monocytes in AIM-V containing recombinant human IL-4 (500 U/ml) and GM-CSF (800 U/ml) for 7 days (R&D, Minneapolis, MN), including feedings on days 1, 3, and 5. On day 7, adherent immature DCs were washed with PBS and then harvested using incubation with Versene (EDTA) (Versene; BioWhittaker® Lonza, Walkersville, MD) for 15 min in a 37° C. incubator. Mature DCs were cultured AIM-V containing IL-4 (500 U/ml) and GM-CSF (800 U/ml) for 5 days, including feedings on days 1 and 3, followed by the addition of stimulation reagents on day 5 that included TNFα (10 ng/ml; R&D), IL-1β (2 ng/ml; R&D), IL-6 (1,000 U/ml; R&D), and Prostaglandin E2 (PGE2) (1,000 ng/ml; Sigma-Aldrich). On day 7, non-adherent mature DCs were harvested from the supernatant.

Purified primary human CD4+ and CD8+ T cells were stimulated by CD3/CD28 beads (Dynabeads® Human T-Expander CD3/CD28 (Invitrogen Dynal, Osol, Norway); immunomagnetic beads to which CD3-specific and CD28-specific monoclonal antibodies had been conjugated) as described (Carpenito, Milone et al. 2009). Briefly, purified CD4+ and CD8+ cells were washed twice in PBS, mixed together at a 1:1 ratio, and then resuspended at a final concentration of $0.6\text{-}0.8\times10^6$ cells/ml in fresh T cell culture medium (RPMI Medium 1640 (RPMI; LTI), containing 10% Human Serum AB (HABS; GemCell™ Gemini Bio-products, West Sacramento, CA), HEPES, GlutaMAX™

(L-glut), Pen Strep, Sodium Pyruvate, MEM non-essential Amino Acids (NEAA), and 2-Mercaptothanol (BME) LTI). Beads were gently mixed extensively, washed three times in PBS, and then combined with T cells at a ratio of 3:1, beads to T cells. The bead-T cell solution was transferred to a tissue culture-treated flask and incubated at 37° C. in a 5% CO2 incubator for 3 days, undisturbed. On day 3, fresh T cell culture medium was added to the culture at a volume of H the initial culture volume and then incubated for an additional 2 days. On day 5, the magnetic beads were removed from the culture using a DynaMag™ magnet (Invitrogen Dynal) and the cells were then resuspended with T cell culture medium to a concentration of ~0.7-0.8×$10^6$ cells/ml. Starting from Day 6, the culture was fed with fresh T cell culture medium down to a concentration of ~0.7-0.8×$10^6$ cells/ml every other day. T cells were frozen as described above when the culture average cell diameter decreased to ~250 $\mu m^3$.

In Vitro Transcription

CD19 and mesothelin (meso)-targeted CARs with 4-1BB and CD3 signaling domains (19-BBz and ss1-BBz, respectively) have been described previously (Carpenito, Milone et al. 2009, Milone, Fish et al. 2009). The PCR products were subcloned into a pGEM.64A-based vector by replacing GFP from pGEM-GFP.64A (Zhao, Zheng et al. 2006) with restriction-enzyme-digested PCR products with HindIII and NotI (New England Biolabs Inc. (NEB), Ipswich, MA) to produce pGEM-ss1.bbz.64A and pGEM-CD19bbz.64A. Similarly, third-generation versions of the CARs were constructed utilizing the CD28 signaling domain. The replaced CAR cDNAs were confirmed by direct sequencing and linearized by Spe I (NEB) digestion before RNA in vitro transcription. mScript RNA System (Epicentre, Madison, WI) or T7 mScript™ Standard mRNA Production System (CELLSCRIPT, Madison, WI) was utilized to generate capped IVT RNA. The IVT RNA was purified using an RNeasy Mini Kit (Qiagen, Valencia, CA) and purified RNA was eluted in RNase-free water at 1-2 mg/ml.

RNA Electroporation

Human T cells were stimulated by CD3/CD28 beads as described above. The stimulated T cells were washed three times with Opti-MEM® I Reduced Serum Medium (OPTI-MEM; LTI) and resuspended in OPTI-MEM at the final concentration of 25×106/ml before electroporation. Subsequently, the stimulated T cells were mixed with 8-10 μg/0.1 ml T cells of IVT RNA and electroporated for a single pulse at 500 V for 0.7 ms in a 2 mm cuvette (Harvard Apparatus BTX, Holliston, MA) using an ECM830 Electro Square Wave Porator (Harvard Apparatus BTX). Electroporated T cells were then cultured overnight in standard T cell culture medium and then stained for respective costimulatory molecule expression by flow cytometry. T cells were co-electroporated with 8 μg of Meso-CAR and 8 μg of RNA encoding each of the costimulatory molecules.

Flow Cytometry/FACS

Cells were stained with commercially available antibodies (BD Biosciences (BD), San Jose, CA; BioLegend, San Diego, CA; dBioscience, Inc., San Diego, CA; Jackson Immunoresearch, West Grove, PA) specific for the indicated markers and analyzed by flow cytometry (FACS). Cells were washed and suspended in FACS buffer (PBS with 1% FBS) containing the indicated Abs, incubated at 4° C. for 30 min, and then washed twice with FACS buffer. Tetramer staining was performed using APC-labeled MART-1 (iTAg Tetramer/APC-HLA-A*0201 Mart-1 (ELAGIGILTV)) or Flu-M1 tetramers (iTAg Tetramer/APC-HLA-A*0201 Influenza-M1 (GILGFVFTL)) at a 1:40 dilution (MBL International Co., Woburn, MA). Flow cytometry acquisition was performed with a BD LSR II (BD Biosciences), and analysis was performed with FlowJo (Treestar, Ashland, OR).

The results are shown in FIGS. 2, 3, 4B, 5A-B, and 6.

Modified In Vitro Priming Assay

A modified in vitro T cell priming assay was used to assess the capacity of RNA electroporated T cells to prime naïve MART-1 peptide-specific T cells. This assay has been described, in part, previously, and is modified herein (Li, Bleakley et al. 2005, Li and Yee 2008, Kaka, Shaffer et al. 2009, Wolfl, Merker et al. 2011, Ramos, Narala et al. 2013). All donor-derived cells were from normal healthy HLA-A2+ donors. Autologous stimulator cells (DCs or RNA-engineered T cells) and effector/responder cells (thawed PBLs), as acquired and cultured above, were washed three times with PBS before establishment of the coculture priming assay (FIG. 4A; Day 0). Stimulator (3.5×105/well) and effector (3.5×106/well) cells were cocultured at a ratio of 1:10 in 6-well plate, in 6 ml/well T cell culture medium containing recombinant human IL-2 (10 U/ml; R&D), IL-21 (30 ng/ml; LTI; IL-21 has been reported to suppress the activity of regulatory T cells that may be present in PBLs), and peptide (0.25 μg/ml). Peptides were either MART-126-35 (ELAGIGILTV (SEQ ID NO: 47)), Flu-M158-66 (GILGFVFTL (SEQ ID NO: 48); positive control) or h-CLIP103-117 (PVSKMRMATPLLMQA (SEQ ID NO: 49); negative control), and were purchased from GenScript USA Inc. (Piscataway, NJ). On days 3, 5, 7, 9 and 11, cocultures were fed by carefully replacing 3 ml of coculture medium (½ the total coculture volume per well) with 3 ml fresh T cell culture medium containing recombinant human IL-2 (20 U/ml), IL-21 (60 ng/ml), IL-7 (20 ng/ml; R&D) and IL15 (20 ng/ml; R&D), each at 2× final concentration. On Day 13, induction of peptide-specific T cell responses were assessed by FACS using tetramer staining, as described above.

Degranulation Assay

The CD107a mobilization assay was performed as described (Betts, Brenchley et al. 2003). One hundred microliters of effector and target cells was plated in 96-well round-bottom plates at a ratio of 1:1, 2:1, or 4:1 (1, 2, or 4×105 effectors+105 targets). Ten microliters of PE-Cy5-labeled anti-CD107a antibody (eBioscience) was added to each cell mixture and incubated at 37° C. for 1 hr before adding GolgiStop (BD). After an additional 2.5 hr of incubation, these cells were stained with anti-CD8-APC-Cy7 (BD) and levels of surface CD107 were determined by flow cytometry, as described above.

Example 2: Screening of Candidate Molecules Involved in Cytotoxic T Lymphocyte (CTL) Priming for Co-Delivery with CARs or TCRs into T Cells The following studies were performed to demonstrate that the anti-tumor activity of CAR/TCR-expressing T cells can be enhanced by co-delivery of costimulatory molecules, thereby increasing the ability of T cells to function as antigen presenting cells and prime T cells (i.e., T:T priming). As described herein, in addition to CAR T cell-directed tumor cell killing, this allowed T cell-mediated priming of non-engineered tumor-reactive T cells, which can persist as tumor suppressors once CAR expression by adoptive RNA CAR T cells has subsided, creating a transient therapy with permanent anti-tumor effects.

Given the many possible immune modulatory genes that can be used to enhance the antigen-presenting cell (APC)

function of RNA CAR T cells (e.g., surface-bound molecules that deliver primary and secondary costimulation, are associated with antigen presentation, determine trafficking and migration patterns, are ligands for DC, as well as cytokines that facilitate priming or suppress regulatory T cell (Treg) responses), the present example focused on evaluating genes regulated in dendritic cells (one of the most potent of the professional APCs) (Chen and Flies 2013).

Initially, proteins known to function as costimulatory molecules were examined. Immature DCs (iDCs) and mature DCs (mDCs) were cultured and assessed for costimulatory molecule expression (CD252, CD70, CD83, CD80, CD49a, CD40, HLA-ABC, CD86, HLA-DR, CD275, CD154, CD137L, and CD43). As shown in FIG. 2, a number of candidate markers were efficiently upregulated in mDCs. In particular, CD252, CD70, CD83, and CD80 showed substantially higher expression in mDCs compared to iDCs. Accordingly, CD252 and CD70 were chosen for further analysis as candidate costimulatory molecules for co-delivery with CARs into T cells. CD86 and CD137l also were included as candidate costimulatory molecules because they have been reported to provide important secondary costimulation signals for T cell priming. FIG. 2 is merely an example demonstrating that costimulatory molecules can be dramatically regulated during classical APC-T cell priming.

To confirm that the above candidates would be expressed upon electroporation of their mRNAs into T cells, CD70, CD83, CD80 (B7-1), CD86 (B7-2), CD275 (ICOS-L), CD43, CD137L (4-1BBL), CD252 (OX40L), CD58 (LFA-3), CD48, TL1A, CD270 (HVEM), CD40, CD154 (CD40L), CD150 (SLAM), and CD64 were cloned and used as templates for in vitro transcription to produce high quality mRNA. All candidates were highly expressed when their mRNAs were electroporated into T cells (FIG. 3), indicating that these candidates could be used to express in T cells for enhancing T cell priming capability.

Figure 4A:
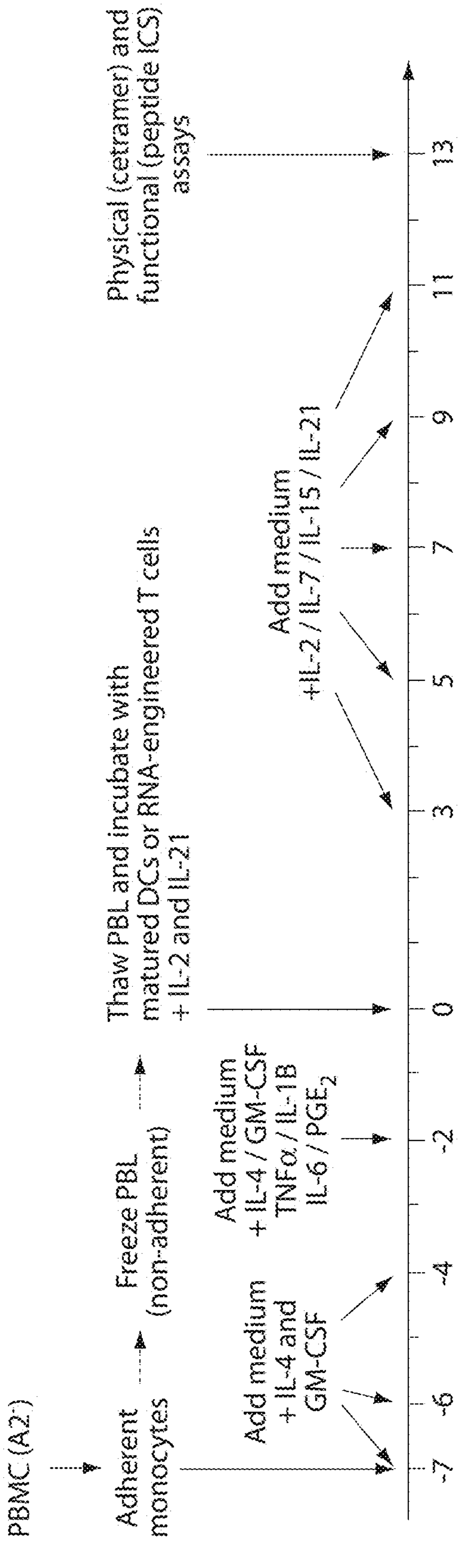
FIG. 4A describes the experimental flow for the modified in vitro priming system using DCs to prime MART-$1^+$ CTL. DCs were cultured (as described in FIG. 1) and then co-cultured in six-well plates with autologous PBMCs at a ratio of (1:10) in the presence of MART-1 peptide (0.25 μg/mL), IL-2, IL-7, IL-15, and IL21 for 13 days. After a single round of peptide stimulation for 13 days, CTL induction was measured by flow cytometry and MART-$1^+$ T cells were detected using an APC-conjugated MART-1 tetramer.

Example 3: Establishment of an In Vitro Priming System for the Identification of Candidate Costimulatory Molecules that Promote Priming of Tumor-Specific T Cells To test the ability of each candidate costimulatory molecule co-delivered into RNA CAR T cells to enhance priming, a modified in vitro priming system was established. This system was based on published studies describing autologous co-culture assays using DCs and T cells that have been used for in vitro T cell induction (Li, Bleakley et al. 2005, Han and Chang 2009, Ramos, Narala et al. 2013), but modified to include only one round of antigen stimulation, as opposed to up to 3 or 4 as described in previous studies, since detectable CTL responses were observed in multiple donors with one round of stimulation (FIG. 4A).

Figure 4B:
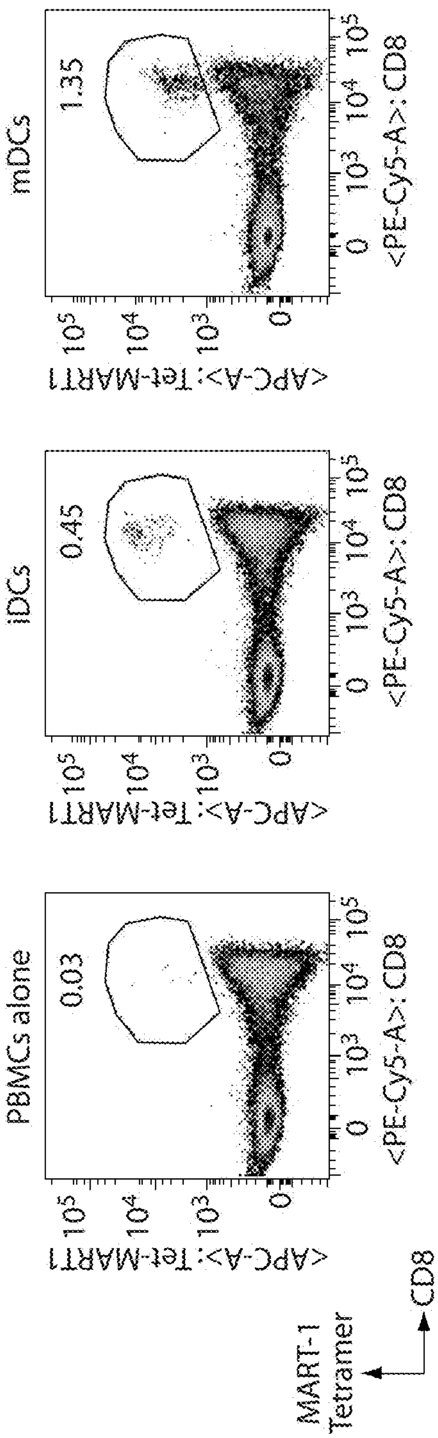
FIG. 4B depicts FACS plots showing the frequency of MART-$1^+$ T cells per well when immature or mature DCs were used as effector cells.

To validate the modified system, autologous DCs and PBLs were used as effectors, as described in published studies. The A2+ CD8+ T cell epitope MART-1, which is present at relatively high frequencies in healthy individuals (Pittet, Valmori et al. 1999), was used as the model tumor antigen. Consistent with previous reports with this peptide antigen (Li, Bleakley et al. 2005, Li and Yee 2008, Kaka, Shaffer et al. 2009, Wolfl, Merker et al. 2011, Ramos, Narala et al. 2013), cultured mature DCs (mDCs) in the modified system were capable of priming MART-1+ T cells to an expectedly greater extent than immature DCs (iDCs) (FIG. 4B).

This result suggests that the newly-developed modified in vitro priming system can be used to test T:T priming and effectively screen a panel of co-delivered RNAs encoding molecules associated with CTL priming.

Example 4: Enhanced Costimulatory Molecule-Mediated Priming of T Cells

Figure 5A:
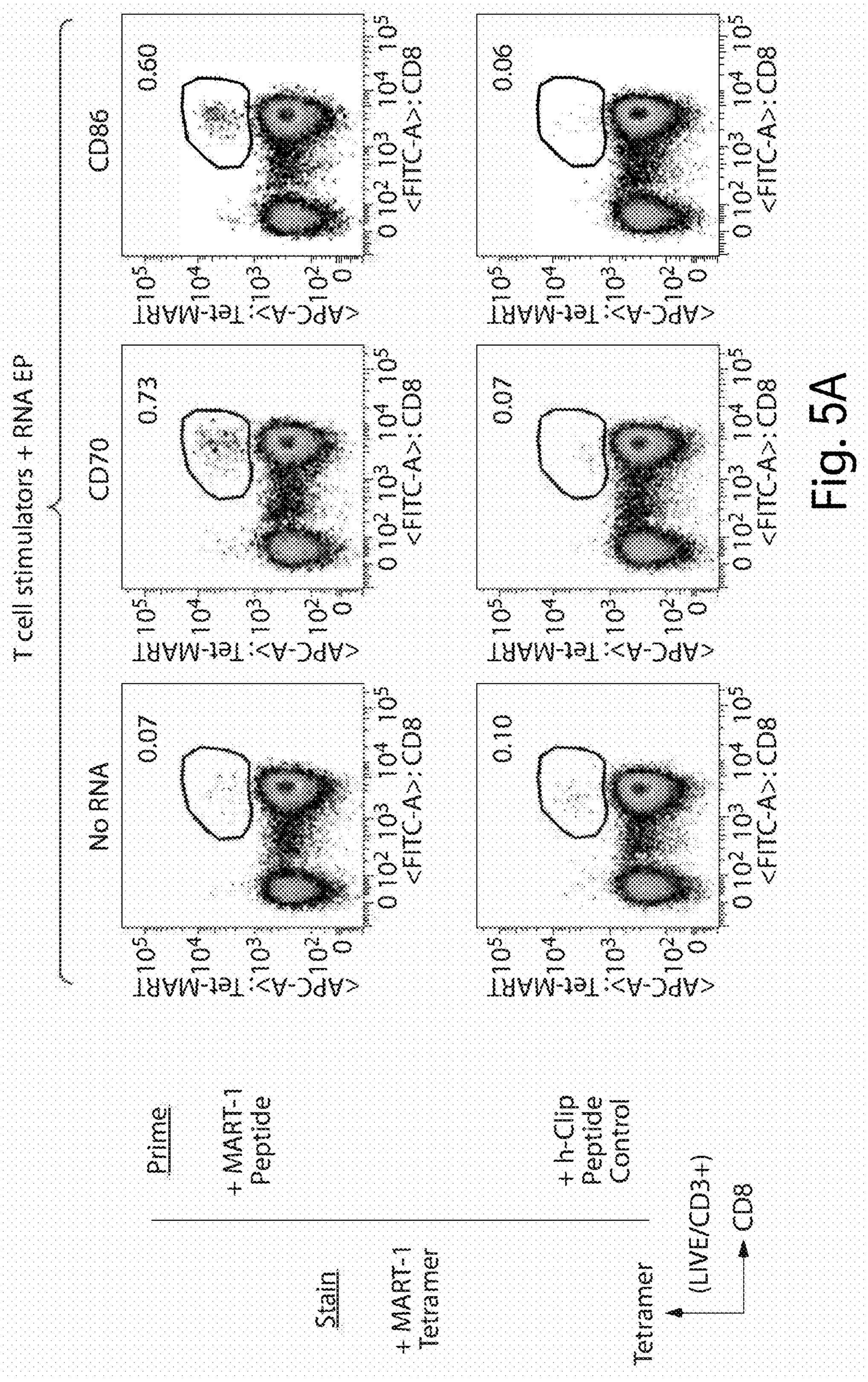
FIGS. 5A and 5B show FACs plots demonstrating that T cells which express costimulatory molecules via RNA electroporation are capable of enhancing T:T priming of MART-1+CTL. Similar to the co-culture assay described for FIG. 3, T cells electroporated with the indicated RNAs were co-cultured with autologous PBLs in six-well plates at a ratio of (1:10) in the presence of MART-1 or h-Clip (control) peptide (0.25 μg/mL), IL-2, IL-7, IL-15, and IL21 for a period of 13 days. After a single round of peptide stimulation for 13 days, CTL induction was measured by flow cytometry and MART-$1^+$ T cells were detected using an APC-conjugated MART-1 tetramer. Numbers in FACS plots indicate percentage of MART-$1^+$ T cells per well.
Figure 5B:
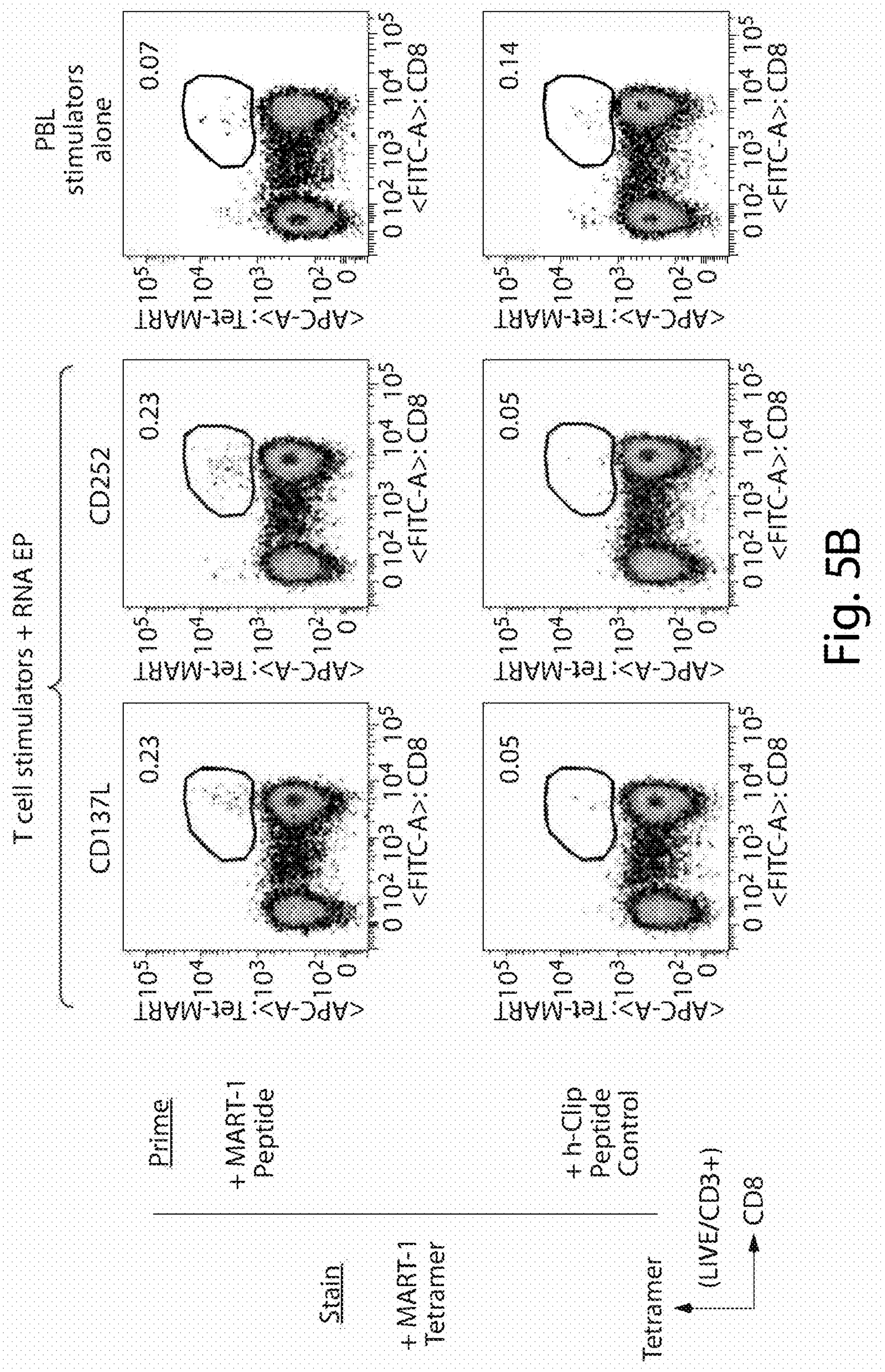

Using the modified in vitro co-culture priming assay, each of the four candidate costimulatory molecules were tested for the ability to enhance the capacity of T cells to directly prime MART-1+ CTLs. When their RNAs were electroporated into T cells, each costimulatory molecule was capable of enhancing MART-1+ CTL priming, as reflected in the increased number of CD8+MART-1+ T cells relative to controls (no electroporation, h-Clip peptide irrelevant antigen control (h-CLIP$_{103-117}$ (PVSKMRMATPLLMQA (SEQ ID NO: 50))), and PBL stimulators alone; FIGS. 5A-B).

Of the four tested candidate co-stimulatory molecules, CD70 provided the strongest enhancement of T:T-mediated MART-1+ CTL induction, increasing priming by over 10-fold when compared to control cells which were electroporated without RNA. T cells expressing CD86, CD137L, and CD252 were able to enhance priming by 8.5-fold, 3.2-fold, and 3.2-fold, respectively, relative to control cells. These results show that costimulatory molecules, such as the 4 candidates tested, can enhance priming capability.

Example 5: Co-Delivery of Costimulatory Molecule with CAR does not Affect the Expression of Either Construct An important goal of this co-delivery strategy is that expression of molecules associated with CTL priming does not interfere with, e.g., decrease or inhibit, CAR expression or function. To this end, the effect of costimulatory molecule expression on CAR expression in T cells was first assessed. To test this, an exemplary CAR, Mesothelin-CAR (Meso-CAR), which has been published by our group previously (Zhao, Moon et al. 2010), was introduced into T cells along with each of the four ETP costimulatory molecules, CD70, CD86, CD137L, and CD252, to assess how the expression of the ETP costimulatory molecules affected the expression of mesothelin-CAR, or vice versa. (MALPVTALLL-PLALLLHAARPGSQVQLQQSGPELEKPGASVKISCK-ASGYSFTGYTMN WVKQSHGKSLEWIGLITPYNGAS-SYNQKFRGKATLTVDKSSSTAYMDLLSLTSEDSAVY FCARG-GYDGRGFDYWGQGTTVTVSSGGGGSGGGGSSGGG SDIELTQSPAIMSASPGEK VTMTCSASSSVSYMHWYQQKSGTSPKRWIYDTSK-LASGVPGRFSGSGSGNSYSLTISSV EAED-DATYYCQQWSKHPLTYGAGTKLEIKASTTTPA-PRPPTPAPTIASQPLSLRPEACRP AAGGAVHTRGLDFACDIYIWAPLAGTCGVLLLSLVIT-LYCKRGRKKLLYIFKQPFMRPV QTTQEEDGCSCRFPEEEEGGCELRVKFSRSADAPA-YKQGQNQLYNELNLGRREEYDVL DKRR-GRDPEMGGKPRRKNPQEGLYNELQKDKMAEAYSEI-GMKGERRRGKGHDGLYQ GLSTATKDTYDALHMQALPPR (SEQ ID NO: 51)). Meso-CAR RNA and RNA for each of the four ETP costimulatory molecules were co-delivered into the same T cell and the expression of each on the surface of T cells was assessed the next day (FIGS. 5A-B).

Co-expression of Meso-CAR along with costimulatory molecules did not result in an adverse effect on either the CAR or the costimulatory molecule, e.g., did not result in decreased expression of the CAR or ETP, or inhibition of CAR or ETP expression. These data demonstrate that CARs may be effectively co-expressed with additional molecules, e.g., ETPs, with minimal interference on the surface expression of the CAR.

Example 6: Co-Expression of Costimulatory Molecules does not Affect CAR-Mediated Cell Killing A key consideration when co-expressing costimulatory molecules to improve the priming ability of CAR T cells is that co-expression has minimal effect on CAR-mediated cell killing, e.g., does not substantially reduce or inhibit CAR-mediated cell killing. Indeed, CAR-mediated tumor cell killing has important downstream effects such as the potential to disrupt the local tumor immunosuppressive environment by destroying tumor cells, releasing tumor antigens, recruiting pro-immune and antigen-presenting cells (APCs), secreting proinflammatory cytokines, and promoting inflammation in general. These immunomodulatory events may all work together to facilitate in vivo priming at the tumor site and/or local lymph nodes of non-engineered tumor-specific $CD8^+$ T cells that may recognize tumor antigens not only targeted by the CAR itself, but also others within the same tumor (i.e., epitope spreading).

Figure 6:
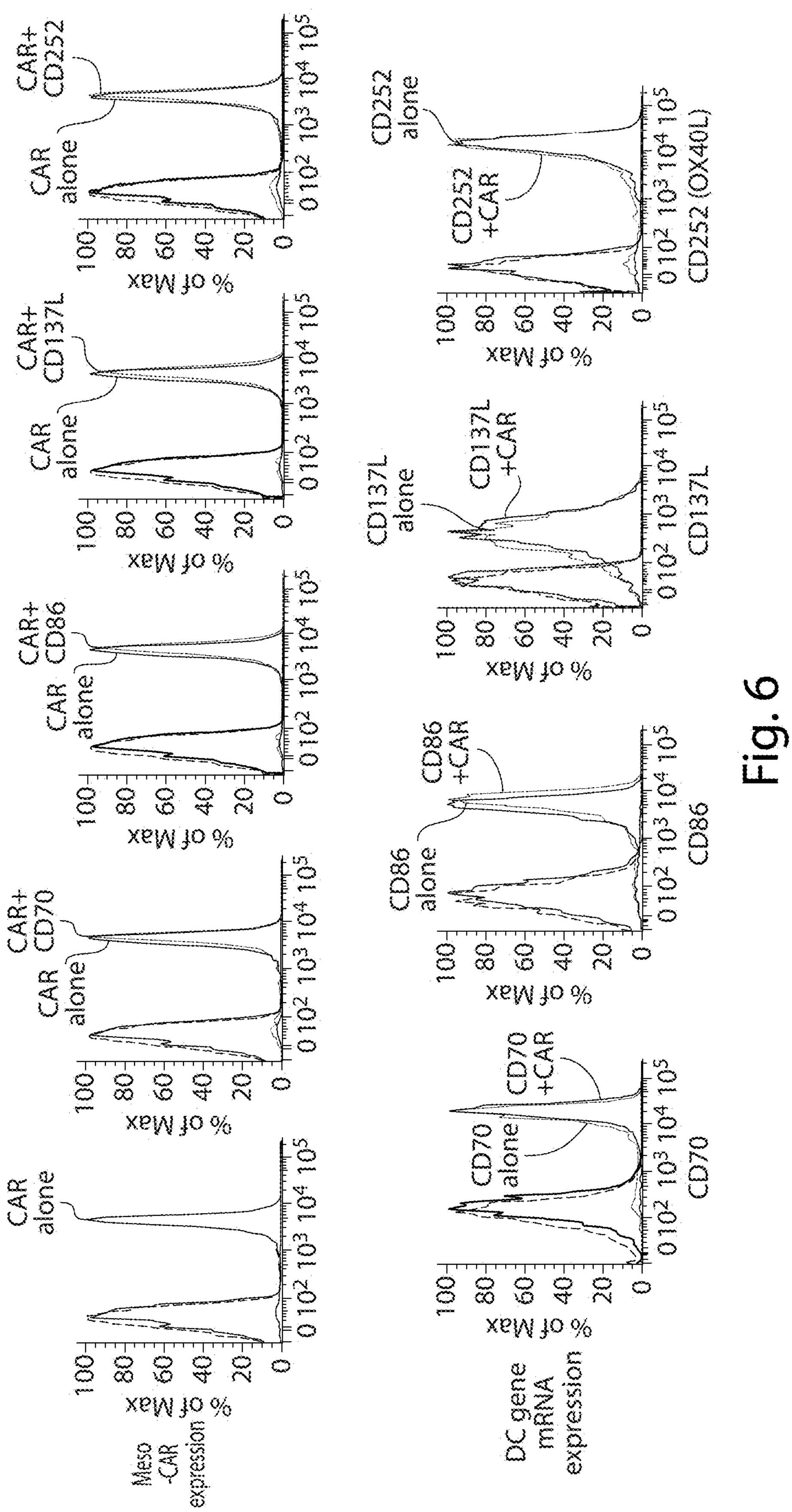
FIG. 6 shows the expression of meso-CAR, CD70, CD86 (B7-2), CD137L (4-1BBL), and CD252 (OX40L) after co-electroporation of RNAs for meso-CAR and the indicated costimulatory molecules into T cells. Co-expression of Meso-CAR along with costimulatory molecules had no remarkable effect on either the CAR or the costimulatory molecule. Electroporation was carried out as described for FIG. 3. T cells were co-electroporated with 8 μg of Meso-CAR and 8 μg of RNA encoding each of the costimulatory molecules. Dashed lines represent T cells that were not stained and thin gray lines are T cells that were electroporated but did not receive RNA. Thick gray lines on top row indicate CAR expression in the absence of costimulatory molecule RNA transfection while the black line designates CAR expression when the two are combined. In the bottom row, black lines indicate expression levels of costimulatory molecules transfected in the absence of CAR, while thick gray line display costimulatory marker expression in the presence of CAR.
Figure 7:
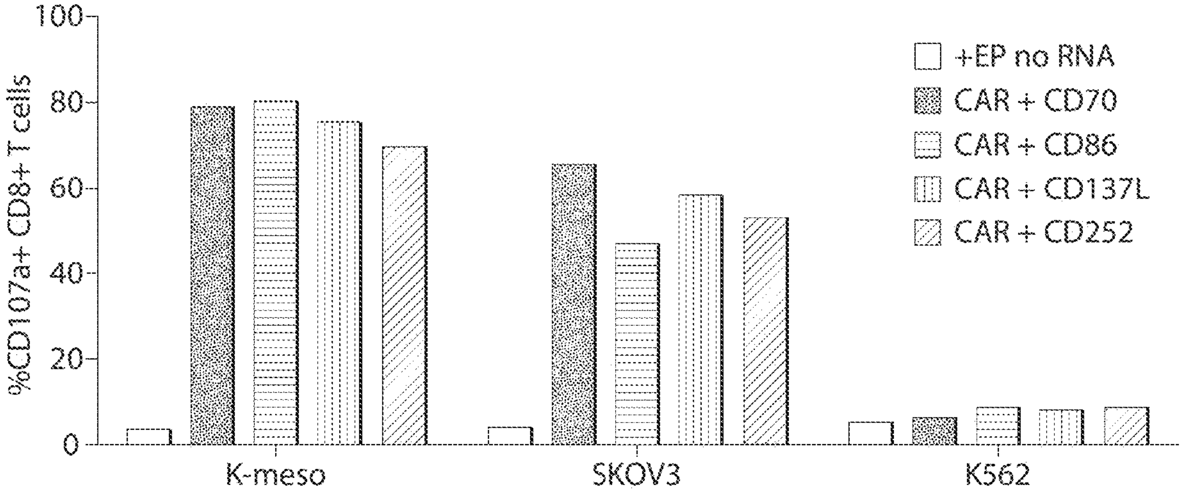
FIG. 7 is a bar graph showing that co-expression of CAR and costimulatory molecules did not affect CAR-mediated cell killing. Meso-CAR expressing T cells also expressing costimulatory molecules were incubated with two different meso-expressing tumor lines (K-meso and SKOV3) and one meso-negative line (K562) and evaluated for CD107a/LAMP-1 exposure on T cell surfaces in a 4 h degranulation assay. Co-expression of CAR and costimulatory molecules did not markedly decrease CAR-mediated cell killing.
Figure 8A:
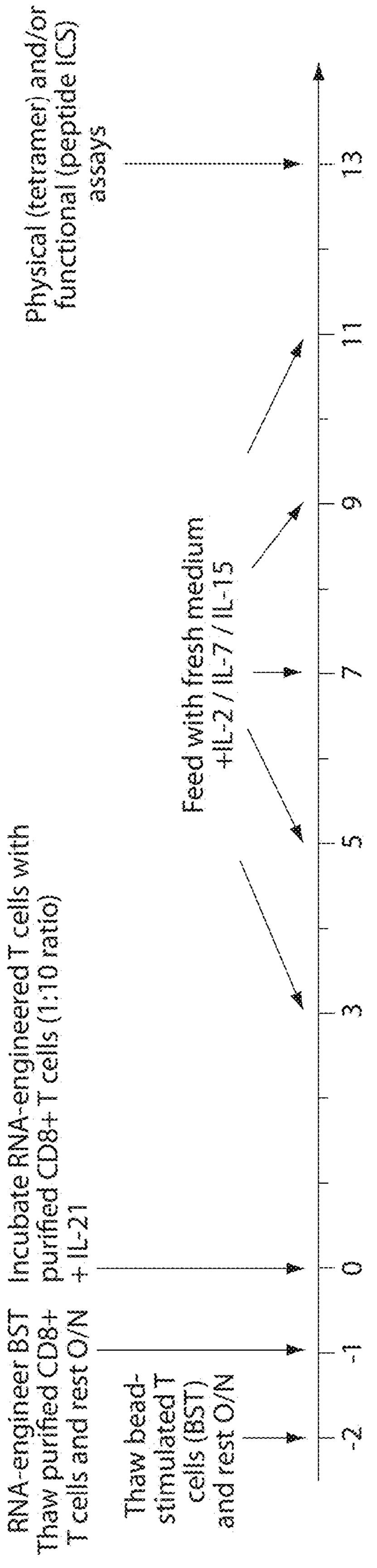
FIG. 8A describes the experimental flow for the modified in vitro priming system using RNA electroporated bead-stimulated T cells to prime MART-1$^+$ CTL. Bead-stimulated T cells were cultured, electroporated with the indicated RNAs, and then co-cultured in 24-well plates with autologous purified CD8+ T cells at a ratio of (1:10) in the presence of MART-1 peptide (0.25-1 μg/mL) and IL-21 for 3 days, followed by subsequent feedings with fresh medium containing IL-2, IL-7 and IL-15 for an additional 10 days. After a single round of peptide stimulation for 13 days, CTL induction was measured by flow cytometry and MART-1$^+$ T cells were detected using an APC-conjugated MART-1 tetramer.
Figure 8B:
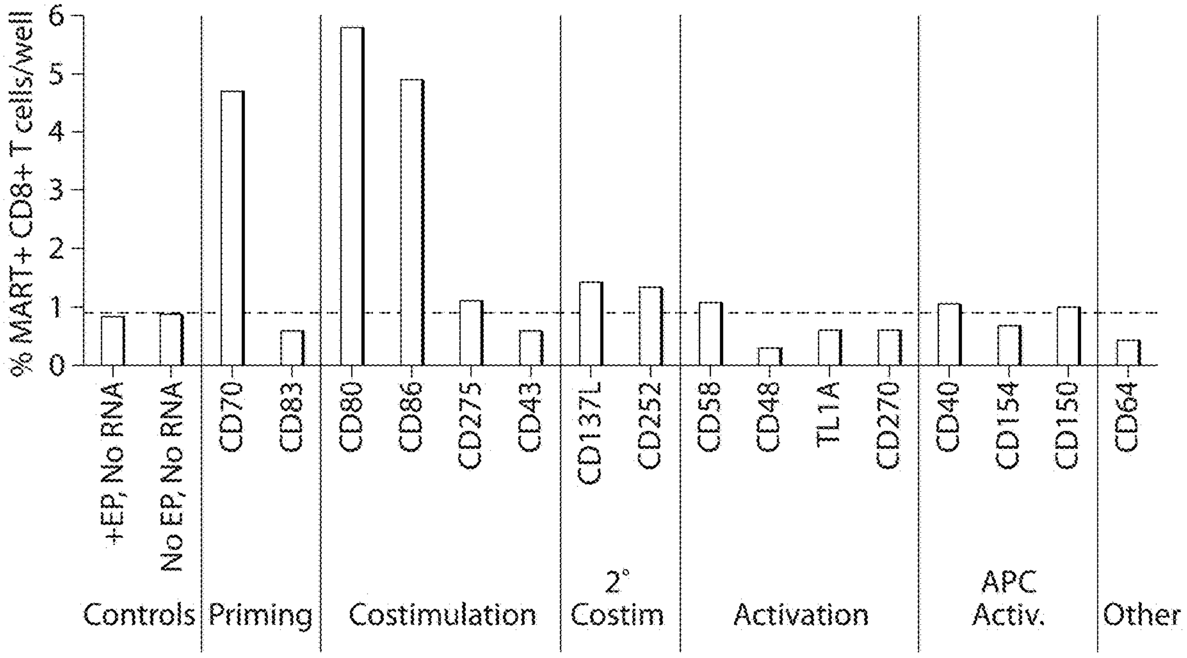
FIG. 8B shows the summarized results of the experiment demonstrating that bead-stimulated T cells which express costimulatory molecules via RNA electroporation are capable of enhancing T:T priming of MART-1+ CTL.
Figure 9A:
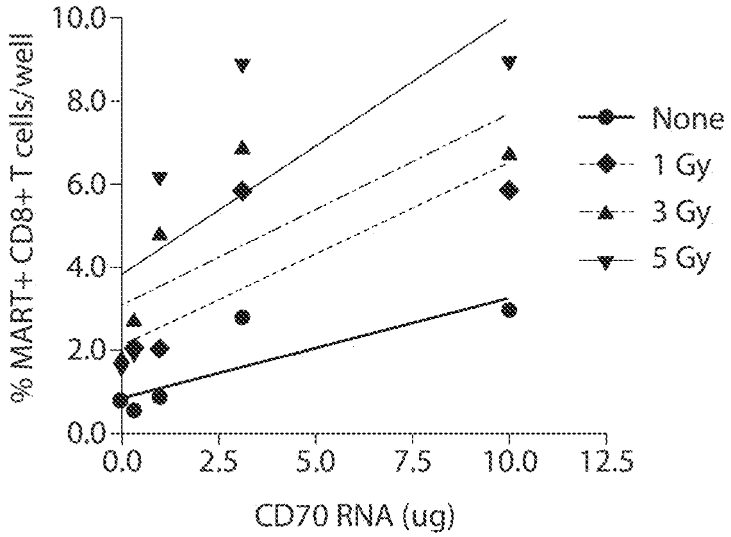
FIG. 9A demonstrates that T:T priming of MART-1+ CTL, as described in FIG. 8, can be further enhanced by the application of low-dose irradiation of RNA-engineered bead-stimulated T cells. Bead-stimulated T cells were cultured, electroporated with the indicated dose of CD70 RNA, subjected to low-dose irradiation at the indicated doses, and then co-cultured in 24-well plates with autologous purified CD8+ T cells at a ratio of (1:10) in the presence of MART-1 peptide (0.25-1 μg/mL) and IL-21 for 3 days, followed by subsequent feedings with fresh medium containing IL-2, IL-7 and IL-15 for an additional 10 days. After a single round of peptide stimulation for 13 days, CTL induction was measured by flow cytometry and MART-1$^+$ T cells were detected using an APC-conjugated MART-1 tetramer. Data are summarized in the scatterplot and linear trend lines for each dosage of irradiation is displayed. Also shown are data from bead-stimulated T cells that were not irradiated, data from those receiving 1 Gy, data from those receiving 3 Gy, and data from those receiving 5 Gy.
Figure 9B:
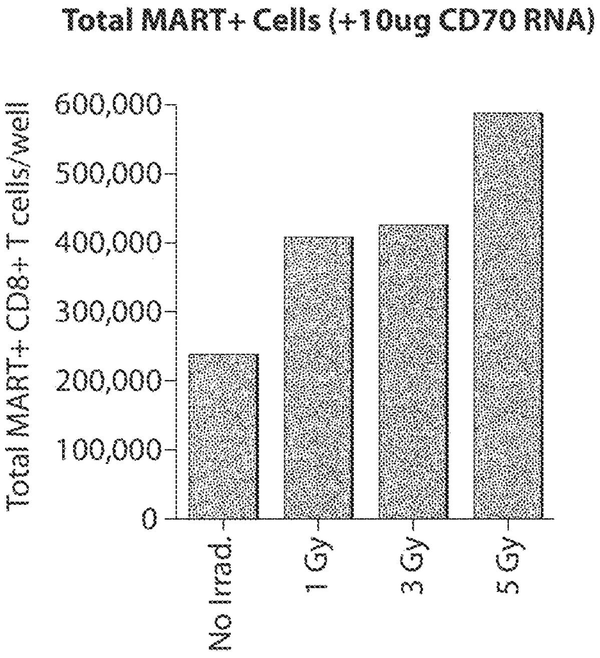
FIG. 9B shows the total number of MART+ CD8+ T cells per well as a function of increasing irradiation. These data demonstrate that low-dose irradiation treatment of RNA-engineered bead-stimulated T cells may enhance their capacity for T:T priming of MART+ CTL.

In this example, the CAR-mediated cell killing ability of T cells co-expressing Meso-CAR and ETP costimulatory molecules was assessed to determine whether co-expression of a CAR with costimulatory molecules would negatively affect CAR-mediated cell killing. Meso-CAR expressing T cells that also express costimulatory molecules were incubated with two different mesothelin-expressing tumor lines (K-meso and SKOV3) and one mesothelin-negative line (K562) and evaluated for CD107a exposure in a degranulation assay. The CD107a mobilization assay is widely used to measure the capacity of T cells to kill target cells, which has been directly correlated to their level of degranulation as quantified by the exposure of LAMP1 protein (CD107a) that normally resides in cytotoxic T cell lytic granules (Betts, Brenchley et al. 2003). Co-expression of CAR and costimulatory molecules did not markedly affect CAR function (FIG. 6). Data points for the Meso-CAR alone from another experiment for K-meso and K562 cells were added to the graph, from Zhao, Moon et al., 2010.

These results suggest that co-expression of costimulatory molecules with CAR has little impact on CAR function, e.g., does not substantially reduce or inhibit CAR-mediated cell killing ability.

Example 7: Effects of Different Molecules Involved in CTL Priming, Individually and in Combination, on RNA CAR T Cell Priming Ability The effects of different candidate molecules involved in pathways associated with CTL priming are tested for the ability to enhance RNA CAR T cell priming of CTLs, as described in the foregoing Examples. Candidate molecules that increase T:T cell priming will also be tested in different combinations for synergistic effects.

Example 8: Efficacy of RNA CAR T Cells Co-Expressing Molecules Involved in CTL Priming on Eradicating Tumor Cells The RNA CART cell co-expressing ETPs are tested in other in vitro priming systems. For example, human CAR T cells are cocultured with tumor cells (likely irradiated), in the presence of a pool of non-engineered T cells and possibly DCs. The readout of this assay includes the induction of tumor-specific T cell responses in the pool of non-engineered T cells, which may be the result of cross-priming of released tumor Ags by the CAR T cells engineered to be dual functional Ag presenters.

Sequences of some examples of various components of CARs of the instant invention is listed in Table 2, where an stands for amino acids, and na stands for nucleic acids that encode the corresponding peptide.

TABLE 2

Sequences of various components of CAR (aa-amino acids, na-nucleic acids that encodes the corresponding protein)

| SEQ ID NO | description | Sequence |
|---|---|---|
| 1 | EF-1 promoter | CGTGAGGCTCCGGTGCCCGTCAGTGGGCAGAGCGCACATCGCCCACAGTCCCCGAG<br>AAGTTGGGGGGAGGGGTCGGCAATTGAACCGGTGCCTAGAGAAGGTGGCGCGGG<br>GTAAACTGGGAAAGTGATGTCGTGTACTGGCTCCGCCTTTTTCCCGAGGGTGGGGG<br>AGAACCGTATATAAGTGCAGTAGTCGCCGTGAACGTTCTTTTTCGCAACGGGTTTGC<br>CGCCAGAACACAGGTAAGTGCCGTGTGTGGTTCCCGCGGGCCTGGCCTCTTTACGG<br>GTTATGGCCCTTGCGTGCCTTGAATTACTTCCACCTGGCTGCAGTACGTGATTCTTGA<br>TCCCGAGCTTCGGGTTGGAAGTGGGTGGGAGAGTTCGAGGCCTTGCGCTTAAGGAG<br>CCCCTTCGCCTCGTGCTTGAGTTGAGGCCTGGCCTGGGCGCTGGGGCCGCCGCGTGC<br>GAATCTGGTGGCACCTTCGCGCCTGTCTCGCTGCTTTCGATAAGTCTCTAGCCATTTA<br>AAATTTTTGATGACCTGCTGCGACGCTTTTTTTCTGGCAAGATAGTCTTGTAAATGCG<br>GGCCAAGATCTGCACACTGGTATTTCGGTTTTTGGGGCCGCGGGCGGCGACGGGGC<br>CCGTGCGTCCCAGCGCACATGTTCGGCGAGGCGGGGCCTGCGAGCGCGGCCACCGA<br>GAATCGGACGGGGGTAGTCTCAAGCTGGCCGGCCTGCTCTGGTGCCTGGCCTCGCG<br>CCGCCGTGTATCGCCCCGCCCTGGGCGGCAAGGCTGGCCCGGTCGGCACCAGTTGC<br>GTGAGCGGAAAGATGGCCGCTTCCCGGCCCTGCTGCAGGGAGCTCAAAATGGAGGA<br>CGCGGCGCTCGGGAGAGCGGGCGGGTGAGTCACCCACACAAAGGAAAAGGGCCTT<br>TCCGTCCTCAGCCGTCGCTTCATGTGACTCCACGGAGTACCGGGCGCCGTCCAGGCA<br>CCTCGATTAGTTCTCGAGCTTTTGGAGTACGTCGTCTTTAGGTTGGGGGGAGGGGTT<br>TTATGCGATGGAGTTTCCCCACACTGAGTGGGTGGAGACTGAAGTTAGGCCAGCTTG<br>GCACTTGATGTAATTCTCCTTGGAATTTGCCCTTTTTGAGTTTGGATCTTGGTTCATTC<br>TCAAGCCTCAGACAGTGGTTCAAAGTTTTTTTCTTCCATTTCAGGTGTCGTGA |

TABLE 2-continued

Sequences of various components of CAR (aa-amino acids, na-nucleic acids that encodes the corresponding protein)

| SEQ ID NO | description | Sequence |
|---|---|---|
| 2 | Leader (aa) | MALPVTALLLPLALLLHAARP |
| 3 | Leader (na) | ATGGCCCTGCCTGTGACAGCCCTGCTGCTGCCTCTGGCTCTGCTGCTGCATGCCGCTA GACCC |
| 4 | CD 8 hinge (aa) | TTTPAPRPPTPAPTIASQPLSLRPEACRPAAGGAVHTRGLDFACD |
| 5 | CD8 hinge (na) | ACCACGACGCCAGCGCCGCGACCACCAACACCGGCGCCCACCATCGCGTCGCAGCCC CTGTCCCTGCGCCCAGAGGCGTGCCGGCCAGCGGCGGGGGGCGCAGTGCACACGA GGGGGCTGGACTTCGCCTGTGAT |
| 6 | Ig4 hinge (aa) | ESKYGPPCPPCPAPEFLGGPSVFLFPPKPKDTLMISRTPEVTCVVVDVSQEDPEVQFNWY VDGVEVHNAKTKPREEQFNSTYRVVSVLTVLHQDWLNGKEYKCKVSNKGLPSSIEKTISK AKGQPREPQVYTLPPSQEEMTKNQVSLTCLVKGFYPSDIAVEWESNGQPENNYKTTPPV LDSDGSFFLYSRLTVDKSRWQEGNVFSCSVMHEALHNHYTQKSLSLSLGKM |
| 7 | Ig4 hinge (na) | GAGAGCAAGTACGGCCCTCCCTGCCCCCCTTGCCCTGCCCCCGAGTTCCTGGGCGGA CCCAGCGTGTTCCTGTTCCCCCCCAAGCCCAAGGACACCCTGATGATCAGCCGGACC CCCGAGGTGACCTGTGTGGTGGTGGACGTGTCCCAGGAGGACCCCGAGGTCCAGTT CAACTGGTACGTGGACGGCGTGGAGGTGCACAACGCCAAGACCAAGCCCCGGGAG GAGCAGTTCAATAGCACCTACCGGGTGGTGTCCGTGCTGACCGTGCTGCACCAGGAC TGGCTGAACGGCAAGGAATACAAGTGTAAGGTGTCCAACAAGGGCCTGCCCAGCAG CATCGAGAAAACCATCAGCAAGGCCAAGGGCCAGCCTCGGGAGCCCCAGGTGTACA CCCTGCCCCCTAGCCAAGAGGAGATGACCAAGAACCAGGTGTCCCTGACCTGCCTGG TGAAGGGCTTCTACCCCAGCGACATCGCCGTGGAGTGGGAGAGCAACGGCCAGCCC GAGAACAACTACAAGACCACCCCCCCTGTGCTGGACAGCGACGGCAGCTTCTTCCTG TACAGCCGGCTGACCGTGGACAAGAGCCGGTGGCAGGAGGGCAACGTCTTTAGCTG CTCCGTGATGCACGAGGCCCTGCACAACCACTACACCCAGAAGAGCCTGAGCCTGTC CCTGGGCAAGATG |
| 8 | IgD hinge (aa) | RWPESPKAQASSVPTAQPQAEGSLAKATTAPATTRNTGRGGEEKKKEKEKEEQEERETK TPECPSHTQPLGVYLLTPAVQDLWLRDKATFTCFVVGSDLKDAHLTWEVAGKVPTGGV EEGLLERHSNGSQSQHSRLTLPRSLWNAGTSVTCTLNHPSLPPQRLMALREPAAQAPVK LSLNLLASSDPPEAASWLLCEVSGFSPPNILLMWLEDQREVNTSGFAPARPPPQPGSTTF WAWSVLRVPAPPSPQPATYTCVVSHEDSRTLLNASRSLEVSYVTDH |
| 9 | IgD hinge (na) | AGGTGGCCCGAAAGTCCCAAGGCCCAGGCATCTAGTGTTCCTACTGCACAGCCCCAG GCAGAAGGCAGCCTAGCCAAAGCTACTACTGCACCTGCCACTACGCGCAATACTGGC CGTGGCGGGGAGGAGAAGAAAAAGGAGAAAGAGAAAGAAGAACAGGAAGAGAG GGAGACCAAGACCCCTGAATGTCCATCCCATACCCAGCCGCTGGGCGTCTATCTCTT GACTCCCGCAGTACAGGACTTGTGGCTTAGAGATAAGGCCACCTTTACATGTTTCGTC GTGGGCTCTGACCTGAAGGATGCCCATTTGACTTGGGAGGTTGCCGGAAAGGTACC CACAGGGGGGGTTGAGGAAGGGTTGCTGGAGCGCCATTCCAATGGCTCTCAGAGCC AGCACTCAAGACTCACCCTTCCGAGATCCCTGTGGAACGCCGGGACCTCTGTCACAT GTACTCTAAATCATCCTAGCCTGCCCCCACAGCGTCTGATGGCCCTTAGAGAGCCAGC CGCCCAGGCACCAGTTAAGCTTAGCCTGAATCTGCTCGCCAGTAGTGATCCCCCAGA GGCCGCCAGCTGGCTCTTATGCGAAGTGTCCGGCTTTAGCCCGCCCAACATCTTGCTC ATGTGGCTGGAGGACCAGCGAGAAGTGAACACCAGCGGCTTCGCTCCAGCCCGGCC CCCACCCCAGCCGGGTTCTACCACATTCTGGGCCTGGAGTGTCTTAAGGGTCCCAGC ACCACCTAGCCCCCAGCCAGCCACATACACCTGTGTTGTGTCCCATGAAGATAGCAG GACCCTGCTAAATGCTTCTAGGAGTCTGGAGGTTTCCTACGTGACTGACCATT |
| 10 | GS hinge/linker (aa) | GGGGSGGGGS |
| 11 | GS hinge/linker (na) | GGTGGCGGAGGTTCTGGAGGTGGAGGTTCC |
| 12 | CD8TM (aa) | IYIWAPLAGTCGVLLLSLVITLYC |
| 13 | CD8 TM (na) | ATCTACATCTGGGCGCCCTTGGCCGGGACTTGTGGGGTCCTTCTCCTGTCACTGGTTA TCACCCTTTACTGC |
| 14 | 4-1BB intracellular domain (aa) | KRGRKKLLYIFKQPFMRPVQTTQEEDGCSCRFPEEEEGGCEL |

TABLE 2-continued

Sequences of various components of CAR (aa-amino acids, na-nucleic acids that encodes the corresponding protein)

| SEQ ID NO | description | Sequence |
|---|---|---|
| 15 | 4-1BB intracellular domain (na) | AAACGGGGCAGAAAGAAACTCCTGTATATATTCAAACAACCATTTATGAGACCAGTA<br>CAAACTACTCAAGAGGAAGATGGCTGTAGCTGCCGATTTCCAGAAGAAGAAGAAGG<br>AGGATGTGAACTG |
| 16 | CD27 (aa) | QRRKYRSNKGESPVEPAEPCRYSCPREEEGSTIPIQEDYRKPEPACSP |
| 17 | CD27 (na) | AGGAGTAAGAGGAGCAGGCTCCTGCACAGTGACTACATGAACATGACTCCCCGCCG<br>CCCCGGGCCCACCCGCAAGCATTACCAGCCCTATGCCCCACCACGCGACTTCGCAGC<br>CTATCGCTCC |
| 18 | CD3-zeta (aa) | RVKFSRSADAPAYKQGQNQLYNELNLGRREEYDVLDKRRGRDPEMGGKPRRKNPQEG<br>LYNELQKDKMAEAYSEIGMKGERRRGKGHDGLYQGLSTATKDTYDALHMQALPPR |
| 19 | CD3-zeta (na) | AGAGTGAAGTTCAGCAGGAGCGCAGACGCCCCCGCGTACAAGCAGGGCCAGAACC<br>AGCTCTATAACGAGCTCAATCTAGGACGAAGAGAGGAGTACGATGTTTTGGACAAG<br>AGACGTGGCCGGGACCCTGAGATGGGGGGAAAGCCGAGAAGGAAGAACCCTCAGG<br>AAGGCCTGTACAATGAACTGCAGAAAGATAAGATGGCGGAGGCCTACAGTGAGATT<br>GGGATGAAAGGCGAGCGCCGGAGGGGCAAGGGGCACGATGGCCTTTACCAGGGTC<br>TCAGTACAGCCACCAAGGACACCTACGACGCCCTTCACATGCAGGCCCTGCCCCCTC<br>GC |
| 20 | CD3-zeta (aa) | RVKFSRSADAPAYQQGQNQLYNELNLGRREEYDVLDKRRGRDPEMGGKPRRKNPQEG<br>LYNELQKDKMAEAYSEIGMKGERRRGKGHDGLYQGLSTATKDTYDALHMQALPPR |
| 21 | CD3-zeta (na) | AGAGTGAAGTTCAGCAGGAGCGCAGACGCCCCCGCGTACCAGCAGGGCCAG<br>AACCAGCTCTATAACGAGCTCAATCTAGGACGAAGAGAGGAGTACGATGTTT<br>TGGACAAGAGACGTGGCCGGGACCCTGAGATGGGGGGAAAGCCGAGAAGGA<br>AGAACCCTCAGGAAGGCCTGTACAATGAACTGCAGAAAGATAAGATGGCGG<br>AGGCCTACAGTGAGATTGGGATGAAAGGCGAGCGCCGGAGGGGCAAGGGGC<br>ACGATGGCCTTTACCAGGGTCTCAGTACAGCCACCAAGGACACCTACGACGC<br>CCTTCACATGCAGGCCCTGCCCCCTCGC |
| 22 | linker | GGGGS |
| 23 | linker | GGTGGCGGAGGTTCTGGAGGTGGAGGTTCC |
| 24 | linker | (Gly-Gly-Gly-Ser)$_n$, where n = 1-10 |
| 25 | linker | (Gly4 Ser)4 |
| 26 | linker | (Gly4 Ser)3 |
| 27 | linker | (Gly3Ser) |
| 28 | polyA | aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa |

TABLE 2-continued

Sequences of various components of CAR
(aa-amino acids, na-nucleic acids that encodes the corresponding protein)

<table>
<tr><th>SEQ ID NO</th><th>description</th><th>Sequence</th></tr>
<tr><td></td><td></td><td>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa</td></tr>
<tr><td>29</td><td>polyA</td><td>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa</td></tr>
<tr><td>30</td><td>polyA</td><td>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa</td></tr>
</table>

TABLE 2-continued

| Sequences of various components of CAR (aa-amino acids, na-nucleic acids that encodes the corresponding protein) | | |
|---|---|---|
| SEQ ID NO | description | Sequence |
| | | aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa |
| 31 | polyA | tttttttttt tttttttttt tttttttttt tttttttttt tttttttttt tttttttttt<br>tttttttttt tttttttttt tttttttttt tttttttttt |
| 32 | polyA | tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt |

TABLE 2-continued

Sequences of various components of CAR
(aa-amino acids, na-nucleic acids that encodes the corresponding protein)

| SEQ ID NO | description | Sequence |
|---|---|---|
| | | tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt tttttttttt tttttttttt tttttttttt tttttttttt<br>tttttttttt tttttttttt |
| 33 | polyA | aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa |

TABLE 2-continued

Sequences of various components of CAR (aa-amino acids, na-nucleic acids that encodes the corresponding protein)

| SEQ ID NO | description | Sequence |
|---|---|---|
| | | aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa |
| 34 | polyA | aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaaaa aaaaaaaaaa<br>aaaaaaaaaa aaaaaaaaaa aaaaaaaaaa aaaaaaaaaa |

EQUIVALENTS

The disclosures of each and every patent, patent application, and publication cited herein are hereby incorporated herein by reference in their entirety. While this invention has been disclosed with reference to specific aspects, it is apparent that other aspects and variations of this invention may be devised by others skilled in the art without departing from the true spirit and scope of the invention. The appended claims are intended to be construed to include all such aspects and equivalent variations.

REFERENCES

Barrett, D. M., Y. Zhao, X. Liu, S. Jiang, C. Carpenito, M. Kalos, R. G. Carroll, C. H. June and S. A. Grupp (2011). "Treatment of advanced leukemia in mice with mRNA engineered T cells." *Hum Gene Ther* 22(12): 1575-1586.

Butterfield, L. H., A. Ribas, V. B. Dissette, S. N. Amarnani, H. T. Vu, D. Oseguera, H. J. Wang, R. M. Elashoff, W. H. McBride, B. Mukherji, A. J. Cochran, J. A. Glaspy and J. S. Economou (2003). "Determinant spreading associated with clinical response in dendritic cell-based immunotherapy for malignant melanoma." *Clin Cancer Res* 9(3): 998-1008.

Chen, L. and D. B. Flies (2013). "Molecular mechanisms of T cell co-stimulation and co-inhibition." *Nat Rev Immunol* 13(4): 227-242.

Corbiere, V., J. Chapiro, V. Stroobant, W. Ma, C. Lurquin, B. Lethe, N. van Baren, B. J. Van den Eynde, T. Boon and P. G. Coulie (2011). "Antigen spreading contributes to MAGE vaccination-induced regression of melanoma metastases." *Cancer Res* 71(4): 1253-1262.

Disis, M. L., V. Goodell, K. Schiffman and K. L. Knutson (2004). "Humoral epitope-spreading following immunization with a HER-2/neu peptide based vaccine in cancer patients." *J Clin Immunol* 24(5): 571-578.

el-Shami, K., B. Tirosh, E. Bar-Haim, L. Carmon, E. Vadai, M. Fridkin, M. Feldman and L. Eisenbach (1999). "MHC class I-restricted epitope spreading in the context of tumor rejection following vaccination with a single immunodominant CTL epitope." *Eur J Immunol* 29(10): 3295-3301.

Fontana, R., M. Bregni, A. Cipponi, L. Raccosta, C. Rainelli, D. Maggioni, F. Lunghi, F. Ciceri, S. Mukenge, C. Doglioni, D. Colau, P. G. Coulie, C. Bordignon, C. Traversari and V. Russo (2009). "Peripheral blood lymphocytes genetically modified to express the self/tumor antigen MAGE-A3 induce antitumor immune responses in cancer patients." *Blood* 113(8): 1651-1660.

Foster, A. E., A. M. Leen, T. Lee, T. Okamura, A. Lu, J. Vera, R. Atkinson, C. M. Bollard, G. Dotti and C. M. Rooney (2007). "Autologous designer antigen-presenting cells by gene modification of T lymphocyte blasts with IL-7 and IL-12." *J Immunother* 30(5): 506-516.

Grewal, I. S., H. G. Foellmer, K. D. Grewal, J. Xu, F. Hardardottir, J. L. Baron, C. A. Janeway, Jr. and R. A. Flavell (1996). "Requirement for CD40 ligand in costimulation induction, T cell activation, and experimental allergic encephalomyelitis." *Science* 273(5283): 1864-1867.

Grupp, S. A. and C. H. June (2011). "Adoptive cellular therapy." *Curr Top Microbiol Immunol* 344: 149-172.

Han, S. and L. J. Chang (2009). "Immunity of lentiviral vector-modified dendritic cells." *Methods Mol Biol* 542: 245-259.

Jonuleit, H., E. Schmitt, G. Schuler, J. Knop and A. H. Enk (2000). "Induction of interleukin 10-producing, nonproliferating CD4(+) T cells with regulatory properties by repetitive stimulation with allogeneic immature human dendritic cells." *J Exp Med* 192(9): 1213-1222.

Kaka, A. S., D. R. Shaffer, R. Hartmaier, A. M. Leen, A. Lu, A. Bear, C. M. Rooney and A. E. Foster (2009). "Genetic modification of T cells with IL-21 enhances antigen presentation and generation of central memory tumor-specific cytotoxic T-lymphocytes." *J Immunother* 32(7): 726-736.

Kaufman, D. L., M. Clare-Salzler, J. Tian, T. Forsthuber, G. S. Ting, P. Robinson, M. A. Atkinson, E. E. Sercarz, A. J. Tobin and P. V. Lehmann (1993). "Spontaneous loss of T-cell tolerance to glutamic acid decarboxylase in murine insulin-dependent diabetes." *Nature* 366(6450): 69-72.

Lehmann, P. V., T. Forsthuber, A. Miller and E. E. Sercarz (1992). "Spreading of T-cell autoimmunity to cryptic determinants of an autoantigen." *Nature* 358(6382): 155-157.

Li, Y., M. Bleakley and C. Yee (2005). "IL-21 influences the frequency, phenotype, and affinity of the antigen-specific CD8 T cell response." *J Immunol* 175(4): 2261-2269.

Li, Y. and C. Yee (2008). "IL-21 mediated Foxp3 suppression leads to enhanced generation of antigen-specific CD8+ cytotoxic T lymphocytes." *Blood* 111(1): 229-235.

Lutz, M. B. and G. Schuler (2002). "Immature, semi-mature and fully mature dendritic cells: which signals induce tolerance or immunity?" *Trends Immunol* 23(9): 445-449.

Markiewicz, M. A., F. Fallarino, A. Ashikari and T. F. Gajewski (2001). "Epitope spreading upon P815 tumor rejection triggered by vaccination with the single class I MHC-restricted peptide P1A." *Int Immunol* 13(5): 625-632.

McRae, B. L., C. L. Vanderlugt, M. C. Dal Canto and S. D. Miller (1995). "Functional evidence for epitope spreading in the relapsing pathology of experimental autoimmune encephalomyelitis." *J Exp Med* 182(1): 75-85.

Melenhorst, J. J., S. R. Solomon, A. Shenoy, N. F. Hensel, J. P. McCoy, Jr., K. Keyvanfar and A. J. Barrett (2006). "Robust expansion of viral antigen-specific CD4+ and CD8+ T cells for adoptive T cell therapy using gene-modified activated T cells as antigen presenting cells." *J Immunother* 29(4): 436-443; discussion 365-436.

Pilon, S. A., C. Kelly and W. Z. Wei (2003). "Broadening of epitope recognition during immune rejection of ErbB-2-positive tumor prevents growth of ErbB-2-negative tumor." *J Immunol* 170(3): 1202-1208.

Pittet, M. J., D. Valmori, P. R. Dunbar, D. E. Speiser, D. Lienard, F. Lejeune, K. Fleischhauer, V. Cerundolo, J. C. Cerottini and P. Romero (1999). "High frequencies of naive Melan-A/MART-1-specific CD8(+) T cells in a large proportion of human histocompatibility leukocyte antigen (HLA)-A2 individuals." *J Exp Med* 190(5): 705-715.

Ramos, C. A., N. Narala, G. M. Vyas, A. M. Leen, U. Gerdemann, E. M. Sturgis, M. L. Anderson, B. Savoldo, H. E. Heslop, M. K. Brenner and C. M. Rooney (2013). "Human papillomavirus type 16 E6/E7-specific cytotoxic T lymphocytes for adoptive immunotherapy of HPV-associated malignancies." *J Immunother* 36(1): 66-76.

Russo, V., A. Cipponi, L. Raccosta, C. Rainelli, R. Fontana, D. Maggioni, F. Lunghi, S. Mukenge, F. Ciceri, M. Bregni, C. Bordignon and C. Traversari (2007). "Lymphocytes genetically modified to express tumor antigens target DCs in vivo and induce antitumor immunity." *J Clin Invest* 117(10): 3087-3096.

Shurin, M. R. (2003). "Preparation of human dendritic cells for tumor vaccination." *Methods Mol Biol* 215: 437-462.

Spear, P., A. Barber and C. L. Sentman (2013). "Collaboration of chimeric antigen receptor (CAR)-expressing T cells and host T cells for optimal elimination of established ovarian tumors." *Oncoimmunology* 2(4): e23564.

Taams, L. S., W. van Eden and M. H. Wauben (1999). "Antigen presentation by T cells versus professional antigen-presenting cells (APC): differential consequences for T cell activation and subsequent T cell-APC interactions." *Eur J Immunol* 29(5): 1543-1550.

Tisch, R., X. D. Yang, S. M. Singer, R. S. Liblau, L. Fugger and H. O. McDevitt (1993). "Immune response to glutamic acid decarboxylase correlates with insulitis in non-obese diabetic mice." *Nature* 366(6450): 72-75.

Vanderlugt, C. L. and S. D. Miller (2002). "Epitope spreading in immune-mediated diseases: implications for immunotherapy." *Nat Rev Immunol* 2(2): 85-95.

Wolfl, M., K. Merker, H. Morbach, S. W. Van Gool, M. Eyrich, P. D. Greenberg and P. G. Schlegel (2011). "Primed tumor-reactive multifunctional CD62L+ human CD8+ T cells for immunotherapy." *Cancer Immunol Immunother* 60(2): 173-186.

Zhao, Y., E. Moon, C. Carpenito, C. M. Paulos, X. Liu, A. L. Brennan, A. Chew, R. G. Carroll, J. Scholler, B. L. Levine, S. M. Albelda and C. H. June (2010). "Multiple injections of electroporated autologous T cells expressing a chimeric antigen receptor mediate regression of human disseminated tumor." *Cancer Res* 70(22): 9053-9061.

Zhao, Y., Z. Zheng, C. J. Cohen, L. Gattinoni, D. C. Palmer, N. P. Restifo, S. A. Rosenberg and R. A. Morgan (2006). "High-efficiency transfection of primary human and mouse T lymphocytes using RNA electroporation." *Mol Ther* 13(1): 151-159.

The invention claimed is:

1. A method of providing anti-tumor immunity in a subject comprising administering to the subject an effective amount of a T cell comprising an exogenous nucleic acid, wherein:

(a) the nucleic acid comprises a first nucleic acid sequence encoding a chimeric antigen receptor (CAR) comprising an extracellular domain, a transmembrane domain, and an intracellular signaling domain, wherein the intracellular signaling domain comprises a costimulatory signaling domain that is a functional signaling domain from a protein selected from the group consisting of OX40, CD27, CD28, CD30, CD40, PD-1, CD2, CD7, CD258, NKG2C, B7-H3, ICAM-1, LFA-1 (CD11a/CD18), ICOS and 4-1BB (CD137), or any combination thereof, and (b) the nucleic acid comprises a second nucleic acid sequence encoding a polypeptide which enhances T cell priming, or a functional fragment or variant thereof, wherein the polypeptide is selected from the group consisting of CD70, CD86, and CD252, and wherein the polypeptide is expressed at a level that: (1) the T cell enhances the priming of another T cell that does not comprise the exogenous nucleic acid, and (2) expression of the polypeptide does not inhibit the cell-killing function of the CAR by more than 40%, provided that:

(i) the first and/or second nucleic acid sequence comprises an RNA; or (ii) the CAR further comprises a second intracellular signaling domain.

2. A method of treating a subject having a disease associated with the expression of a disease-associated antigen, comprising administering to the subject an effective amount of a T cell comprising an exogenous nucleic acid, wherein:

(a) the nucleic acid comprises a first nucleic acid sequence encoding a chimeric antigen receptor (CAR) comprising an extracellular domain, a transmembrane domain, and an intracellular signaling domain, wherein the intracellular signaling domain comprises a costimulatory signaling domain that is a functional signaling domain from a protein selected from the group consisting of OX40, CD27, CD28, CD30, CD40, PD-1, CD2, CD7, CD258, NKG2C, B7-H3, ICAM-1, LFA-1 (CD11a/CD18), ICOS and 4-1BB (CD137), or any combination thereof, and (b) the nucleic acid comprises a second nucleic acid sequence encoding a polypeptide which enhances T cell priming, or a functional fragment or variant thereof, wherein the polypeptide is selected from the group consisting of CD70, CD86, and CD252, and wherein the polypeptide is expressed at a level that: (1) the T cell enhances the priming of another T cell that does not comprise the exogenous nucleic acid, and (2) expression of the polypeptide does not inhibit the cell-killing function of the CAR by more than 40%, provided that:

(i) the first and/or second nucleic acid sequence comprises an RNA; or (ii) the CAR further comprises a second intracellular signaling domain.

3. The method of claim 2, wherein the disease is selected from the group consisting of a proliferative disease, a precancerous condition, a non-cancer related indication, a viral infection, and a bacterial infection.

4. A method of enhancing epitope spreading in a subject with cancer comprising administering to the subject a T cell comprising an exogenous nucleic acid, wherein:

(a) the nucleic acid comprises a first nucleic acid sequence encoding a chimeric antigen receptor (CAR) comprising an extracellular domain, a transmembrane domain, and an intracellular signaling domain, wherein the intracellular signaling domain comprises a costimulatory signaling domain that is a functional signaling domain from a protein selected from the group consisting of OX40, CD27, CD28, CD30, CD40, PD-1, CD2, CD7, CD258, NKG2C, B7-H3, ICAM-1, LFA-1 (CD11a/CD18), ICOS and 4-1BB (CD137), or any combination thereof, and (b) the nucleic acid comprises a second nucleic acid sequence encoding a polypeptide which enhances T cell priming, or a functional fragment or variant thereof, wherein the polypeptide is selected from the group consisting of CD70, CD86, and CD252, and wherein the polypeptide is expressed at a level that: (1) the T cell enhances the priming of another T cell that does not comprise the exogenous nucleic acid, and (2) expression of the polypeptide does not inhibit the cell-killing function of the CAR by more than 40%, provided that:

(i) the first and/or second nucleic acid sequence comprises an RNA; or (ii) the CAR further comprises a second intracellular signaling domain.

5. A method of vaccinating a subject comprising administering to the subject a T cell comprising an exogenous nucleic acid, wherein:

(a) the nucleic acid comprises a first nucleic acid sequence encoding a chimeric antigen receptor (CAR) comprising an extracellular domain, a transmembrane domain, and an intracellular signaling domain, wherein the intracellular signaling domain comprises a costimulatory signaling domain that is a functional signaling domain from a protein selected from the group consisting of OX40, CD27, CD28, CD30, CD40, PD-1, CD2, CD7, CD258, NKG2C, B7-H3, ICAM-1, LFA-1 (CD11a/CD18), ICOS and 4-1BB (CD137), or any combination thereof, and (b) the nucleic acid comprises a second nucleic acid sequence encoding a polypeptide which enhances T cell priming, or a functional fragment or variant thereof, wherein the polypeptide is selected from the group consisting of CD70, CD86, and CD252, and wherein the polypeptide is expressed at a level that: (1) the T cell enhances the priming of another T cell that does not comprise the exogenous nucleic acid, and (2) expression of the polypeptide does not inhibit the cell-killing function of the CAR by more than 40%, provided that:

(i) the first and/or second nucleic acid sequence comprises an RNA; or (ii) the CAR further comprises a second intracellular signaling domain.

6. The method of claim 5, further comprising administering to the subject an antigen, wherein the antigen is a tumor antigen, a viral antigen, or a bacterial antigen.

7. The method of claim 2, wherein the first and second nucleic acid sequences are disposed on a single nucleic acid molecule.

8. The method of claim 2, wherein:

(i) the second intracellular signaling domain comprises a costimulatory signaling domain, (ii) the intracellular signaling domain comprises a functional signaling domain of CD3 zeta, common FcR gamma (FCER1G), Fc gamma RIIa, FcR beta (Fc Epsilon R1b), CD3 gamma, CD3 delta, CD3 epsilon, CD79a, CD79b, DAP10, and DAP12, (iii) the intracellular signaling domain comprises a CD3zeta domain and the second intracellular signaling domain comprises a 4-1BB domain, (iv) the transmembrane domain comprises a transmembrane protein of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154, or (v) the extracellular domain is connected to the transmembrane domain by a hinge region.

9. The method of claim 2, wherein:

(i) the first nucleic acid sequence comprises an RNA, (ii) the second nucleic acid sequence comprises an RNA, or (iii) the first and the second nucleic acid sequence each comprise RNA.

10. The method of claim 9, wherein:

(i) the T cell is transfected to transiently express the first and/or second RNAs, (ii) the T cell does not comprise an exogenous DNA encoding the first or second RNA, (iii) the first and/or second RNAs are generated by in vitro transcription, (iv) the first and/or second RNAs are synthetic RNAs, or (v) the first and/or second RNAs are introduced into the T cell by electroporation.

11. The method of claim 2, wherein the first and/or second nucleic acid sequence comprises DNA or cDNA.

12. The method of claim 2, wherein:

(i) the first and/or second nucleic acid sequence comprises a vector, (ii) the first and/or second nucleic acid sequence comprises a viral vector, (iii) the first and/or second nucleic acid sequence comprises a retroviral vector or a lentiviral vector, or (iv) the T cell is virally transduced to express the first and/or second nucleic acid sequence.

13. The method of claim 2, wherein the extracellular domain of the CAR comprises an antigen-binding domain, wherein:

(i) the antigen-binding domain is an scFv domain, (ii) the antigen-binding domain binds to an antigen associated with a disease state, wherein the disease state is selected from the group consisting of a proliferative disease, a precancerous condition, a non-cancer indication, a viral infection, and a bacterial infection, (iii) the antigen-binding domain binds to a tumor antigen, a viral antigen, or a bacterial antigen, or (iv) the antigen-binding domain binds to a tumor antigen, wherein the tumor antigen is an antigen associated with a cancer selected from the group consisting of brain cancer, bladder cancer, breast cancer, cervical cancer, colorectal cancer, liver cancer, kidney cancer, lymphoma, leukemia, lung cancer, melanoma, metastatic melanoma, mesothelioma, neuroblastoma, ovarian cancer, prostate cancer, pancreatic cancer, renal cancer, skin cancer, thymoma, sarcoma, non-Hodgkin's lymphoma, Hodgkin's lymphoma, uterine cancer, and combinations thereof.

14. The method of claim 2, wherein:

(i) the T cell has enhanced antigen presentation ability relative to a T cell which lacks the second nucleic acid sequence, (ii) the T cell has enhanced T cell priming ability relative to a T cell which lacks the second nucleic acid sequence, (iii) the T cell has increased efficacy in killing tumor cells or reducing tumor size in a subject with a tumor relative to a T cell comprising only the first nucleic acid sequence, or (iv) the T cell enhances the priming of T cells with a tumor antigen, a viral antigen, or a bacterial antigen.

15. The method of claim 2, wherein the T cell is transfected to transiently express a nucleic acid comprising a third nucleic acid sequence encoding a polypeptide which enhances T cell priming, or a functional fragment or variant thereof, which differs from the polypeptide encoded by the second nucleic acid sequence.

16. The method of claim 15, wherein:

(i) the T cell has increased T cell priming ability relative to a T cell comprising the first nucleic acid sequence and second nucleic acid sequence, but not the third nucleic acid sequence, (ii) the third nucleic acid sequence comprises an RNA, (iii) the third nucleic acid sequence comprises an RNA, wherein the T cell is transfected to transiently express the third RNA, (iv) the third nucleic acid sequence comprises an RNA, wherein the cell does not comprise an exogenous DNA encoding the third RNA, or (v) the third nucleic acid sequence comprises DNA.

17. The method of claim 15, wherein the T cell further comprises one or more additional distinct nucleic acid sequences encoding a polypeptide which enhances T cell priming, or a functional fragment or variant thereof, which differ from the polypeptides encoded by the second and third nucleic acid sequences.

18. The method of claim 17, wherein:

(i) the one or more additional nucleic acid sequences comprises RNA, or (ii) the one or more additional nucleic acid sequences comprise DNA.

19. The method of claim 17, wherein the first, second, third, and/or additional nucleic acid sequences are transcribed from an in vitro transcription vector.

20. The method of claim 7, wherein:

(i) the single nucleic acid molecule comprises an RNA, or (ii) the single nucleic acid molecule comprises a DNA.

21. The method of claim 2, wherein the first and second nucleic acid sequences are disposed on two or more distinct nucleic acid molecules.

22. The method of claim 2, wherein the first and second nucleic acid sequences are disposed on two distinct nucleic acid molecules, and wherein:

(i) one or both nucleic acid molecules comprise RNA, (ii) one or both nucleic acid molecules comprise DNA, or (iii) one nucleic acid molecule comprises an RNA and the other nucleic acid molecule comprises a DNA.

* * * * *